(12) United States Patent
Haque et al.

(10) Patent No.: US 11,504,093 B2
(45) Date of Patent: Nov. 22, 2022

(54) EQUALIZATION FOR MATRIX BASED LINE IMAGERS FOR ULTRASOUND IMAGING SYSTEMS

(71) Applicant: eXo Imaging, Inc., Redwood City, CA (US)

(72) Inventors: Yusuf Haque, Woodside, CA (US); Sandeep Akkaraju, Wellesley, MA (US); Janusz Bryzek, Oakland, CA (US); Andalib Chowdhury, San Jose, CA (US)

(73) Assignee: EXO IMAGING, INC., Redwood City, CA (US)

( * ) Notice: Subject to any disclaimer, the term of this patent is extended or adjusted under 35 U.S.C. 154(b) by 0 days.

(21) Appl. No.: 17/156,058

(22) Filed: Jan. 22, 2021

(65) Prior Publication Data
US 2022/0233168 A1   Jul. 28, 2022

(51) Int. Cl.
*H04B 1/02* (2006.01)
*A61B 8/00* (2006.01)
(Continued)

(52) U.S. Cl.
CPC .......... *A61B 8/4494* (2013.01); *A61B 8/4488* (2013.01); *A61B 8/469* (2013.01);
(Continued)

(58) Field of Classification Search
None
See application file for complete search history.

(56) References Cited

U.S. PATENT DOCUMENTS 2,710,388 A * 6/1955 Chun ............... G01S 7/524
367/115
3,100,886 A * 8/1963 Marks ............... B06B 1/0269
367/137
(Continued)

FOREIGN PATENT DOCUMENTS

CA      2628100 C  *  8/2016  ......... G01S 7/52095
WO  WO-2013046087 A1    4/2013
(Continued)

OTHER PUBLICATIONS

Tan, Mingliang, et al. "A front-end ASIC with high-voltage transmit switching and receive digitization for forward-looking intravascular ultrasound." 2017 IEEE Custom Integrated Circuits Conference (CICC). IEEE, 2017. (Year: 2017).*
(Continued)

*Primary Examiner* — Isam A Alsomiri
*Assistant Examiner* — Jonathan D Armstrong
(74) *Attorney, Agent, or Firm* — Wilson Sonsini Goodrich & Rosati

(57) ABSTRACT

Disclosed herein are ultrasonic transducer systems comprising: an ultrasonic imager comprising a plurality of pMUT transducer elements; and one or more circuitries connected electronically to the plurality of transducer element, the one or more circuitries configured to enable: pulse transmission and reception of reflected signal for the ultrasonic transducer, where inductors are used to equalize impedance to obtain greater pressure output. Also disclosed are methods of altering a pressure of an ultrasonic wave emitted by an ultrasonic transducer.

26 Claims, 43 Drawing Sheets

(51) Int. Cl.
  *G01S 15/89*    (2006.01)
  *B06B 1/02*    (2006.01)
  *B06B 1/06*    (2006.01)

(52) U.S. Cl.
  CPC .............. *A61B 8/54* (2013.01); *B06B 1/0215* (2013.01); *G01S 15/8925* (2013.01); *B06B 1/0292* (2013.01); *B06B 1/06* (2013.01)

(56) References Cited

U.S. PATENT DOCUMENTS

| | | | |
|---|---|---|---|
| 3,251,026 A * | 5/1966 | May, Jr. | B06B 1/02 367/138 |
| 3,980,905 A * | 9/1976 | Miller | B06B 1/0223 310/317 |
| 4,081,706 A * | 3/1978 | Edelson | B06B 1/0253 310/316.01 |
| 5,542,426 A * | 8/1996 | Watanabe | B06B 1/0607 29/25.35 |
| 5,555,534 A | 9/1996 | Maslak et al. | |
| 5,675,554 A | 10/1997 | Cole et al. | |
| 5,685,308 A | 11/1997 | Wright et al. | |
| 5,928,152 A | 7/1999 | Wright et al. | |
| 5,970,025 A | 10/1999 | Cole et al. | |
| 6,359,367 B1 | 3/2002 | Sumanaweera et al. | |
| 6,645,145 B1 * | 11/2003 | Dreschel | B06B 1/00 600/443 |
| 6,726,626 B1 * | 4/2004 | Hossack | B06B 1/0292 331/116 R |
| 6,937,176 B2 | 8/2005 | Freeman et al. | |
| 7,508,737 B1 | 3/2009 | Alexandru | |
| 7,824,335 B2 | 11/2010 | Wodnicki | |
| 7,901,358 B2 | 3/2011 | Mehi et al. | |
| 8,019,016 B1 | 9/2011 | Lee et al. | |
| 8,137,280 B2 | 3/2012 | Angelsen et al. | |
| 8,416,643 B2 | 4/2013 | Magee | |
| 8,545,406 B2 | 10/2013 | Magee | |
| 8,834,369 B2 | 9/2014 | Magee | |
| 8,836,792 B1 * | 9/2014 | Butler | H04R 17/00 348/163 |
| 8,926,514 B2 | 1/2015 | Magee | |
| 9,439,625 B2 | 9/2016 | Cogan et al. | |
| 9,521,991 B2 | 12/2016 | Rothberg et al. | |
| 9,592,032 B2 | 3/2017 | Rothberg et al. | |
| 10,405,829 B2 | 9/2019 | Pelissier et al. | |
| 10,641,879 B2 | 5/2020 | Pellegretti et al. | |
| 10,755,692 B2 | 8/2020 | Ralston et al. | |
| 10,857,567 B2 | 12/2020 | Singh et al. | |
| 11,154,276 B2 | 10/2021 | Koptenko | |
| 2001/0020130 A1 | 9/2001 | Gee et al. | |
| 2002/0046320 A1 | 4/2002 | Shaath | |
| 2003/0036704 A1 * | 2/2003 | Cerofolini | G01S 15/895 600/437 |
| 2003/0149363 A1 * | 8/2003 | Dreschel | A61B 8/4483 600/437 |
| 2004/0267134 A1 * | 12/2004 | Hossack | B06B 1/0292 600/459 |
| 2005/0068221 A1 | 3/2005 | Freeman et al. | |
| 2005/0075572 A1 | 4/2005 | Mills et al. | |
| 2007/0016023 A1 | 1/2007 | Phelps et al. | |
| 2007/0242567 A1 | 10/2007 | Daft et al. | |
| 2008/0242969 A1 | 10/2008 | Sayeh et al. | |
| 2008/0255451 A1 | 10/2008 | Cohen et al. | |
| 2008/0262357 A1 | 10/2008 | Wodnicki | |
| 2008/0269614 A1 | 10/2008 | Adachi et al. | |
| 2009/0007414 A1 | 1/2009 | Phelps et al. | |
| 2009/0048522 A1 * | 2/2009 | Huang | B06B 1/0292 600/459 |
| 2009/0141592 A1 * | 6/2009 | Huang | A61B 8/00 367/181 |
| 2009/0228229 A1 * | 9/2009 | Trandafir | B06B 1/0238 702/106 |
| 2009/0240152 A1 | 9/2009 | Angelsen et al. | |
| 2009/0326375 A1 | 12/2009 | Magee | |
| 2009/0326609 A1 * | 12/2009 | Doron | A61B 5/6843 607/60 |
| 2010/0020645 A1 | 1/2010 | Wodnicki et al. | |
| 2010/0198070 A1 * | 8/2010 | Asafusa | A61B 8/4444 600/443 |
| 2010/0240992 A1 | 9/2010 | Hao | |
| 2010/0242611 A1 * | 9/2010 | Terazawa | G01S 15/931 73/629 |
| 2010/0244623 A1 * | 9/2010 | Huang | B06B 1/0207 310/300 |
| 2010/0249596 A1 | 9/2010 | Magee | |
| 2010/0312119 A1 * | 12/2010 | Hashiba | B06B 1/0292 600/459 |
| 2011/0125022 A1 | 5/2011 | Lazebnik | |
| 2011/0225222 A1 | 9/2011 | Gunwani et al. | |
| 2012/0068574 A1 * | 3/2012 | Wu | G10K 11/002 310/314 |
| 2012/0143059 A1 | 6/2012 | Magee | |
| 2012/0245457 A1 * | 9/2012 | Crowley | A61B 8/445 600/424 |
| 2013/0206962 A1 | 8/2013 | Barr et al. | |
| 2013/0334987 A1 * | 12/2013 | Garg | H01L 41/042 318/116 |
| 2013/0336095 A1 * | 12/2013 | Seppa | G01D 21/00 367/137 |
| 2014/0128740 A1 | 5/2014 | Chiang et al. | |
| 2014/0155747 A1 | 6/2014 | Bennett et al. | |
| 2014/0243676 A1 | 8/2014 | Cogan et al. | |
| 2014/0249414 A1 | 9/2014 | Herzog et al. | |
| 2015/0015515 A1 | 1/2015 | Dickinson et al. | |
| 2015/0087991 A1 * | 3/2015 | Chen | G01S 7/52033 600/459 |
| 2015/0265245 A1 | 9/2015 | Von Ramm et al. | |
| 2015/0297193 A1 | 10/2015 | Rothberg et al. | |
| 2015/0374341 A1 | 12/2015 | Chen et al. | |
| 2016/0151045 A1 | 6/2016 | Pelissier et al. | |
| 2016/0202349 A1 | 7/2016 | Rothberg et al. | |
| 2016/0242739 A1 | 8/2016 | Rothberg et al. | |
| 2016/0245894 A1 * | 8/2016 | Deng | A61B 5/1112 |
| 2016/0350963 A1 | 12/2016 | Petkov et al. | |
| 2017/0100096 A1 | 4/2017 | Min | |
| 2017/0117753 A1 * | 4/2017 | Charthad | A61B 5/036 |
| 2017/0135676 A1 | 5/2017 | Rothberg et al. | |
| 2017/0209122 A1 | 7/2017 | Lee et al. | |
| 2017/0296144 A1 | 10/2017 | Rothberg et al. | |
| 2017/0296145 A1 | 10/2017 | Rothberg et al. | |
| 2017/0328870 A1 | 11/2017 | Garlepp et al. | |
| 2018/0028154 A1 | 2/2018 | Zhai | |
| 2018/0071775 A1 * | 3/2018 | Zhuang | B06B 1/0292 |
| 2018/0103925 A1 * | 4/2018 | Kim | A61B 8/4483 |
| 2018/0140270 A1 | 5/2018 | Profio et al. | |
| 2018/0153510 A1 | 6/2018 | Haque et al. | |
| 2018/0192999 A1 | 7/2018 | Song et al. | |
| 2018/0225824 A1 | 8/2018 | Fram et al. | |
| 2018/0321381 A1 | 11/2018 | Cohen et al. | |
| 2018/0361431 A1 | 12/2018 | Singh et al. | |
| 2018/0366102 A1 | 12/2018 | Ralston et al. | |
| 2019/0133556 A1 | 5/2019 | Koptenko | |
| 2019/0150881 A1 * | 5/2019 | Maharbiz | A61B 5/686 |
| 2019/0187278 A1 | 6/2019 | Ozawa et al. | |
| 2019/0196012 A1 | 6/2019 | Savord | |
| 2019/0212424 A1 | 7/2019 | Savord et al. | |
| 2019/0261954 A1 | 8/2019 | Chen et al. | |
| 2019/0261955 A1 | 8/2019 | Chen et al. | |
| 2019/0282834 A1 * | 9/2019 | Zawada | A61B 34/10 |
| 2019/0299251 A1 | 10/2019 | Chen et al. | |
| 2019/0361102 A1 | 11/2019 | Price et al. | |
| 2019/0381535 A1 * | 12/2019 | Zhuang | B06B 1/0292 |
| 2019/0388059 A1 | 12/2019 | Pelissier et al. | |
| 2020/0221233 A1 * | 7/2020 | Kent | B06B 1/0618 |
| 2020/0315586 A1 | 10/2020 | Sanchez | |
| 2020/0346248 A1 * | 11/2020 | van Rens | B06B 1/0292 |
| 2020/0405266 A1 | 12/2020 | Yang et al. | |
| 2020/0405267 A1 | 12/2020 | Yang et al. | |
| 2020/0405271 A1 | 12/2020 | Chiu et al. | |
| 2021/0028792 A1 | 1/2021 | Hwang et al. | |

(56) References Cited

U.S. PATENT DOCUMENTS

| 2021/0183832 A1 | 6/2021 | Chen et al. |
| 2021/0293952 A1 | 9/2021 | Haque et al. |
| 2021/0295816 A1 | 9/2021 | Kim et al. |

FOREIGN PATENT DOCUMENTS

| WO | WO-2018102621 A1 | 6/2018 |
| WO | WO-2019182771 A1 | 9/2019 |
| WO | WO-2020068473 A1 | 4/2020 |
| WO | WO-2020150253 A1 | 7/2020 |
| WO | WO-2021178057 A1 | 9/2021 |
| WO | WO-2022159327 A1 | 7/2022 |

OTHER PUBLICATIONS

Bjastad. High frame rate ultrasound imaging using parallel beamforming. Doctoral Thesis. Norwegian University of Science and Technology (136 pgs.) (Jan. 2009).

Lingall. Time-domain Reconstruction Methods for Ultrasonic Array Imaging: A Statistical Approach. Doctoral Thesis Uppsala University Signals and Systems (193 pgs.)(2004).

PCT/US2020/013530 International Search Report and Written Opinion dated May 20, 2020.

PCT/US2020/013530 Invitation to Pay Additional Fees dated Mar. 16, 2020.

Rathod. A Review of Electric Impedance Matching Techniques for Piezoelectric Sensors, Actuators and Transducers. Electronics 8(2):169 (2019).

PCT/US2019/051238 International Search Report and Written Opinion dated Dec. 19, 2019.

PCT/US2021/014141 International Search Report and Written Opinion dated Apr. 8, 2021.

PCT/US2022/011417 International Search Report and Written Opinion dated Mar. 28, 2022.

PCT/US2022/012315 International Search Report and Written Opinion dated Apr. 7, 2022.

PCT/US2022/020599 International Search Report and Written Opinion dated Jun. 9, 2022.

PCT/US2022/022810 International Search Report and Written Opinion dated Jul. 18, 2022.

* cited by examiner

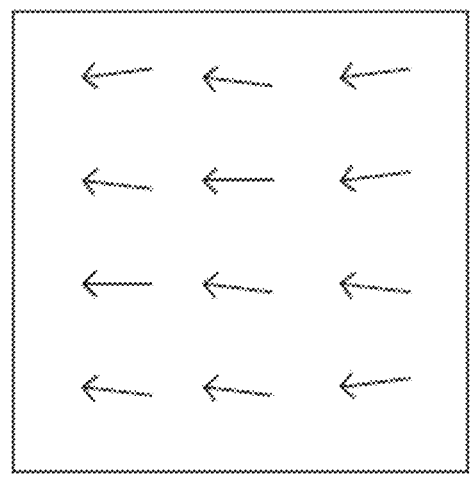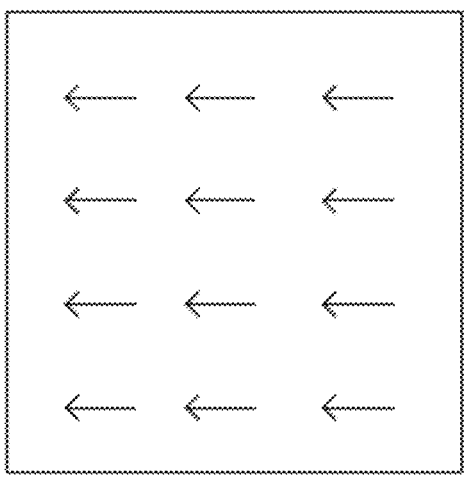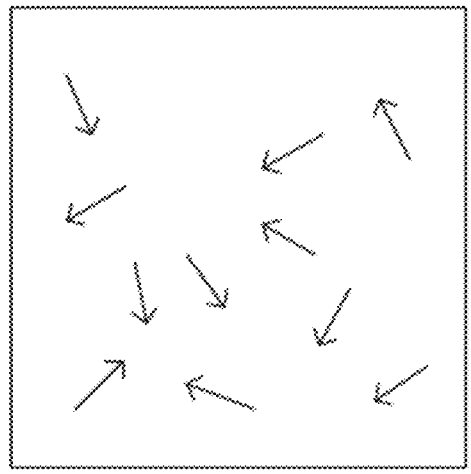
Fig. 6

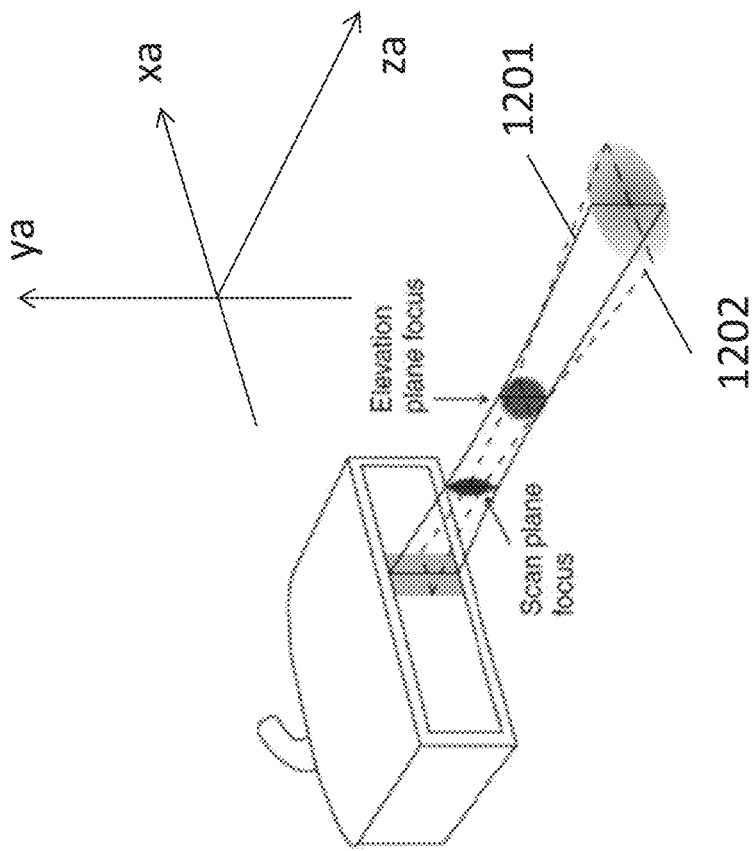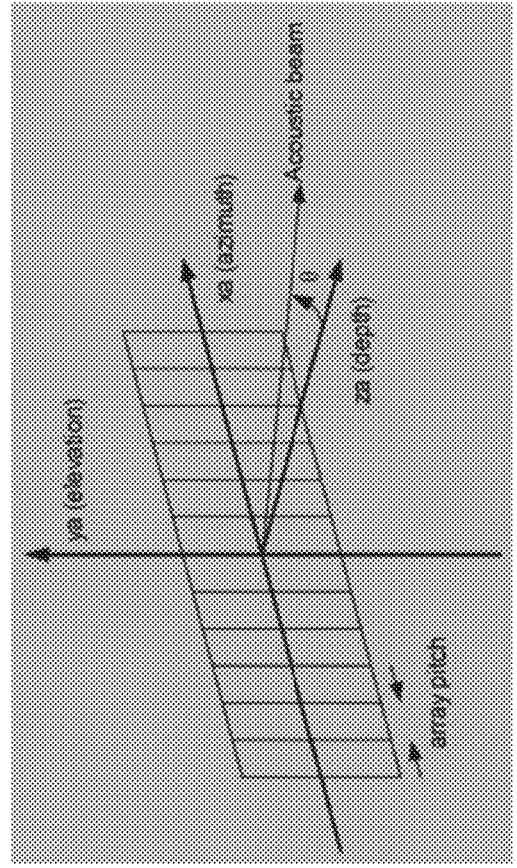
Fig. 10A

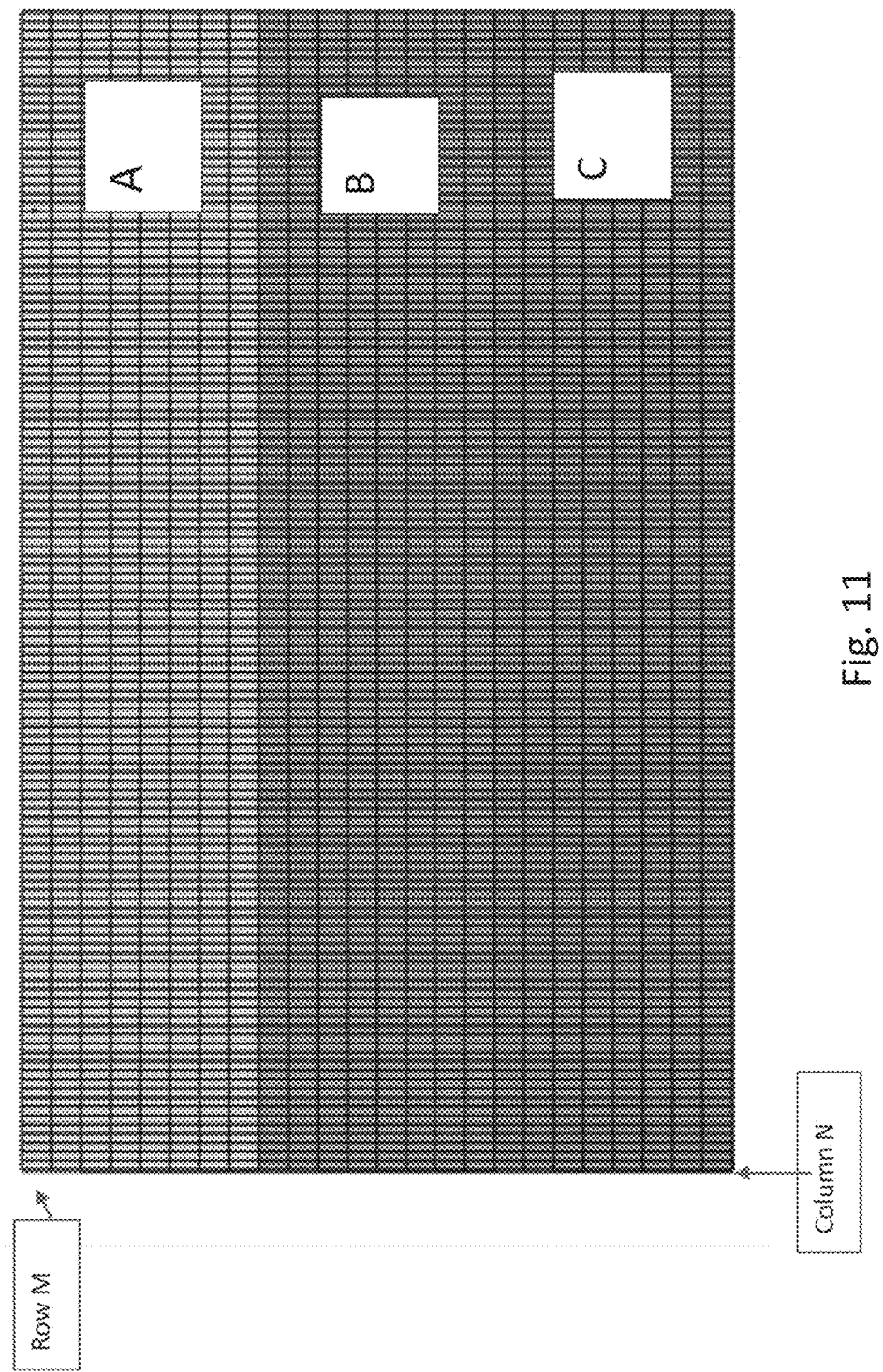

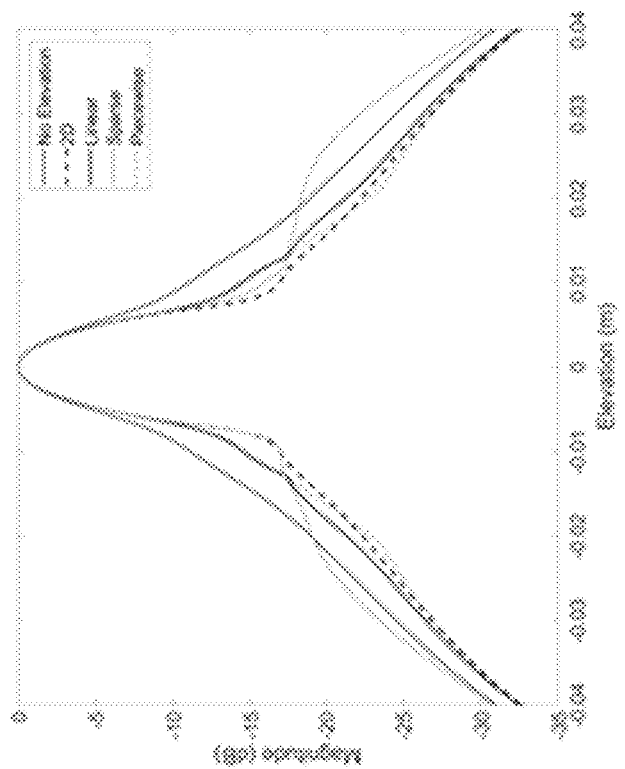
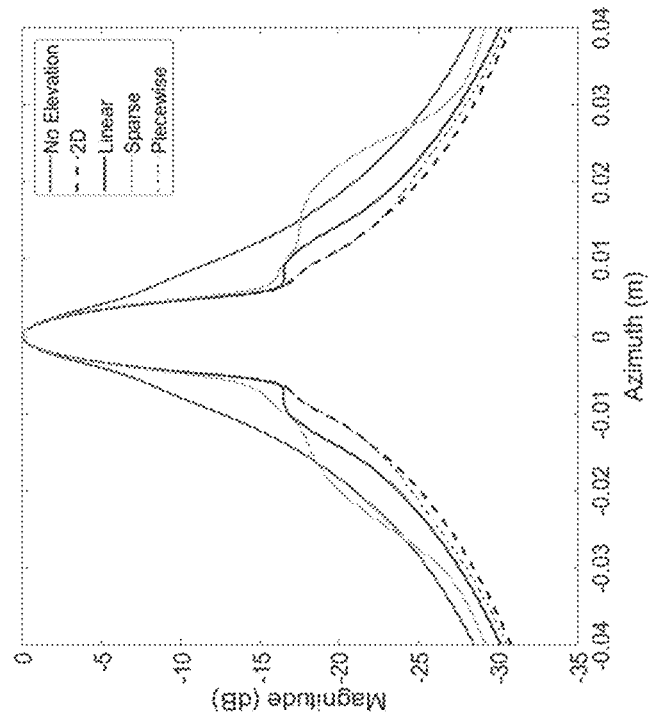
Fig. 21

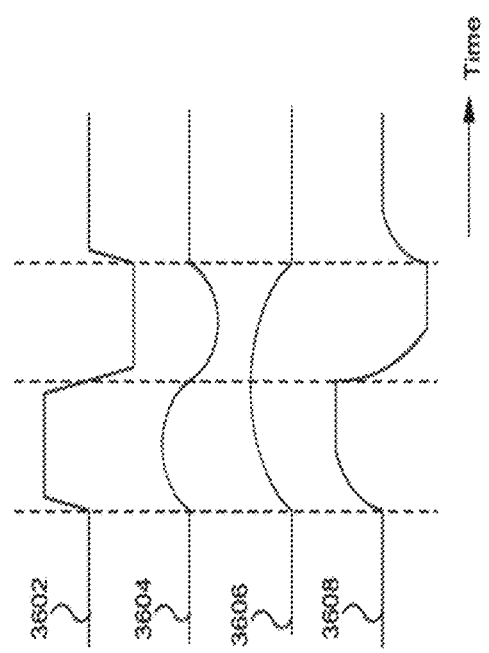
FIG. 30
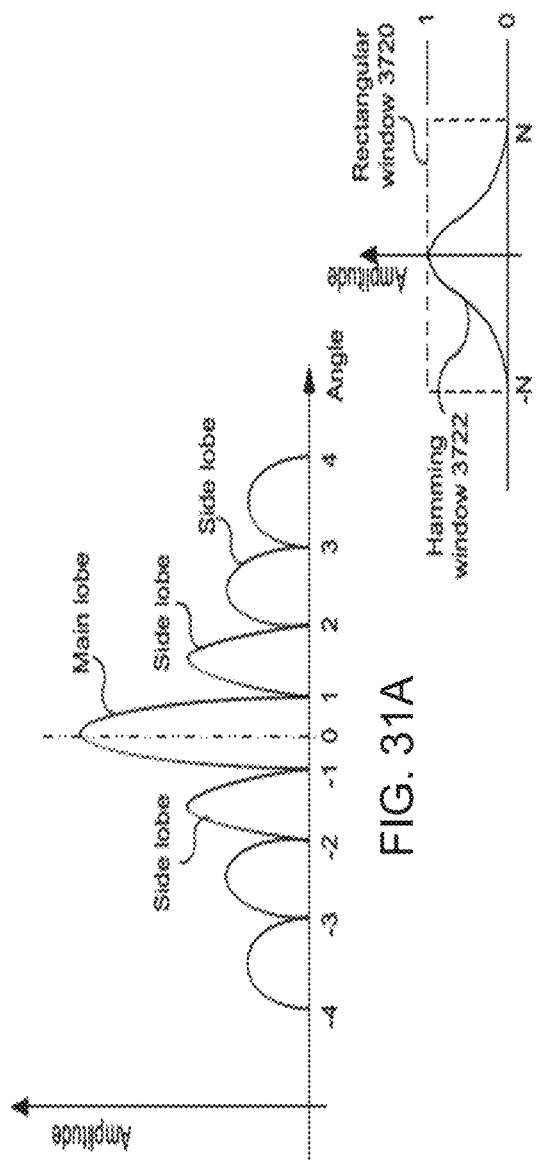
FIG. 31A
FIG. 31B

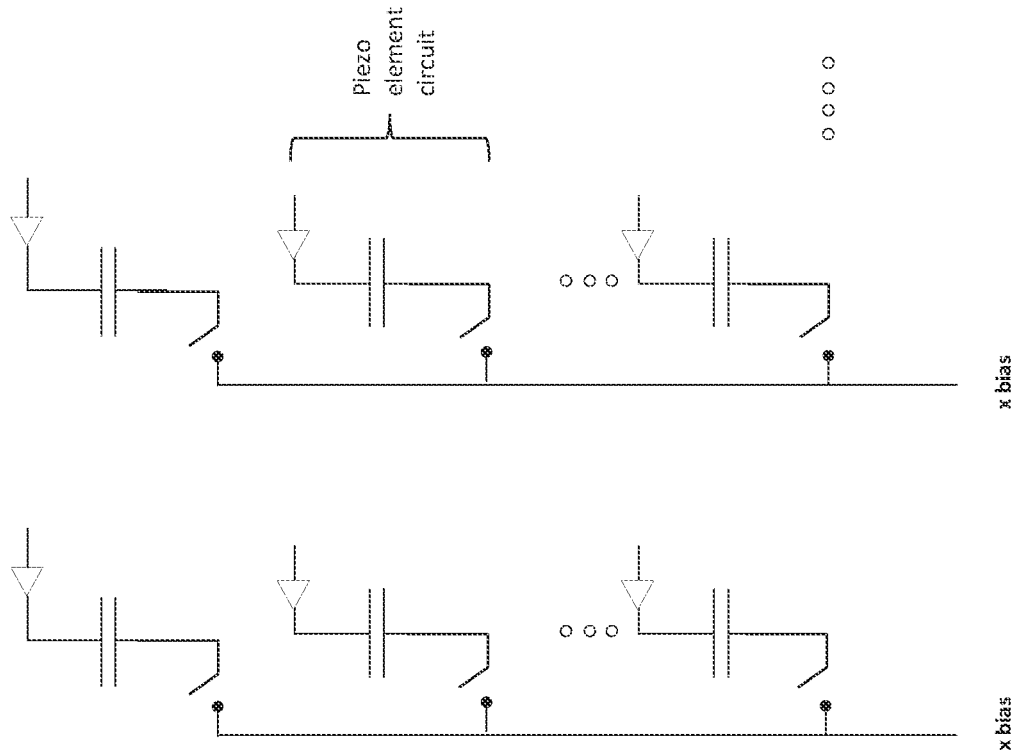

EQUALIZATION FOR MATRIX BASED LINE IMAGERS FOR ULTRASOUND IMAGING SYSTEMS

BACKGROUND

For ultrasound imaging, transducers are used to transmit an ultrasonic beam towards the target to be imaged and a reflected waveform is received by the transducer. The received waveform is converted to an electrical signal and with further signal processing an ultrasound image is created. Conventionally, for two-dimensional (2D) imaging, the ultrasonic transducer includes a one-dimensional (1D) transceiver array for emitting an ultrasonic beam. It is desirable to generate high pressure levels in the ultrasonic beam transmitted.

SUMMARY

Piezoelectric sensors have been used for medical imaging for more than two decades. These are typically built using bulk piezoelectric films. These films form piezoelectric elements which are arranged along columns in the azimuth direction. Each column can be driven by transmit drivers. By using different time delays on successive columns, it may be possible to focus transmitted beams in the azimuth direction.

The elevation disposition of the array of piezoelectric elements can permit the beam of the array to be electronically focused into a narrow beam in the elevation plane. The single row of piezoelectric elements of the transceiver array does not enable electronic focusing in the elevation or thickness dimension of the 2D ultrasound image. A traditional 2D ultrasound image is in the azimuth plane with some thickness in the elevation direction (i.e., the conventional technique for restricting the beam to a thin image slice is to mechanically focus the beam in this transverse or elevational dimension, either by contouring the piezoelectric elements in this dimension or lensing each element). A 2D array of transducers can be arranged such that elements in the elevation direction allow electronic focusing in the elevation direction while also allowing azimuth electronic focusing that is traditionally done in legacy systems.

For optimal transfer of power from an input source to another circuit, the output impedance of the source should be a complex conjugate of the input impedance of the circuit it is driving. In particular optimally, the real parts of both impedances should be equal and the complex parts should be complex conjugates of one another. Transducers using piezoelectric micromachined ultrasound transducer (pMUT) implementations are highly capacitive in nature. For a transmit driver trying to transmit ultrasonic signals into tissue, the driver's impedance needs to match the transducer's input impedance as described above. However, pMUT based transducers are highly capacitive and this requires inductors to be used in series with source drivers to maximize power transferred to the transducer.

In an aspect, an ultrasonic imaging system comprising a transducer is disclosed. The transducer comprises at least one transducer element. Each transducer element has two terminals. The at least one transducer element is in a transmit mode. The transducer also comprises at least one transmit driver. The each transmit driver is connected to each first terminal of the at least one transducer element. The transducer also comprises at least one inductor comprising two terminals. Each first terminal of each inductor is connected to each second terminal of each transducer element. Each second terminal of each inductor is connected to a bias voltage.

In some embodiments, the transducer is a piezoelectric micro machined transducer (pMUT) device.

In some embodiments, the transducer is a capacitive micromachined ultrasonic transducer (cMUT) device or a bulk piezo transducer.

In some embodiments, the at least one transducer element is a plurality of transducer elements organized in an array.

In some embodiments, the array is organized in rows and columns. A plurality of transducer elements in a column is electronically selected to define a column of transducer elements.

In some embodiments, a plurality of transducer elements in a row is selected electronically to define a row of transducer elements.

In some embodiments, delays of transducer elements in a first column are independent from delays of transducer elements in a second column and delays of transducer elements in a first row are independent from delays of transducer elements in a second row.

In some embodiments, transducer elements on a column have different delays.

In some embodiments, the bias voltage is selected from a group consisting of ground, negative, and positive voltages.

In some embodiments, a bandwidth of the transducer is increased in a region of interest.

In some embodiments, at least one value of the at least one inductor is selected to provide a pressure output increase in a frequency range of interest.

In some embodiments, at least one value of the at least one inductor is chosen to be large enough to offset changes in phase introduced by at least one capacitance of the at least one transducer element.

In some embodiments, a bandwidth of the transducer is controlled by selecting a number of transducer elements on a column.

In some embodiments, a pressure output for the selected transducer elements is adjusted by changing a plurality of voltage drive levels of a plurality of transmit drivers of the selected transducer elements.

In some embodiments, the voltage drive levels are changed using a multilevel transmit drive pulse and selecting a desired digital drive level.

In some embodiments, the voltage drive levels are further controlled using pulse width modulation on a transmit pulsar waveform.

In some embodiments, the transducer is configured to provide electronic control of elevation focus in an elevation direction along the column.

In some embodiments, a transducer element along the column is driven by a multilevel pulse.

In some embodiments, a transducer element on a column is driven by a sequence of multilevel pulses.

In some embodiments, pulse magnitude, width, shape, pulse frequency, and combinations thereof of a multilevel pulse of the sequence of multilevel pulses are electrically programmable.

In some embodiments, a delay of an onset of the multilevel pulse is electrically programmable.

In some embodiments, the delay for an element indexed by a row and a column is calculated by summing a delay for the column with a delay for the row.

In some embodiments, a delay may be a summation of a coarse delay and a fine delay.

In some embodiments, the delay of pulse onset is programmable in an X direction.

In some embodiments, the delay of pulse onset is programmable in a Y direction.

In some embodiments, a shape of the multilevel pulse is selected from a group consisting of sinusoidal and digital square.

In some embodiments, the transmit driver is configured to drive the one or more transducer elements along a column. The transmit driver is driven by signals from a transmit channel. The signals of the transmit channel are delayed electronically relative to delay applied to other transmit channels driving other transducer elements on different columns.

In some embodiments, the one or more transducer elements along the column operate with substantially identical delays.

In some embodiments, the transmit channel and additional transmit channels are configured to electrically control relative delays between adjacent columns. The control circuit is configured to set relative delays for a first number of transducer elements on the columns such that the first number of transducer elements in a same row share substantially identical relative delays with a second number of transducer elements of a starting row.

In some embodiments, a transducer element of the plurality of transducer elements comprises a top section, a central section, and a bottom section, each of which comprise a number of rows and a number of columns for pulse transmission and reception of the reflected ultrasonic signal. The pulse transmission and reception of the reflected ultrasonic signal from the top section, central section, and bottom section is used for focusing the reflected ultrasonic signal in an azimuth direction using a first beamformer. An elevation focus is achieved using a second beamformer.

In some embodiments, a focal distance in an elevation direction is electronically programmed.

In some embodiments, the pulse transmission and reception of the reflected signal of the top section and the bottom section are performed simultaneously.

In some embodiments, the transducer elements perform parallel beamforming to develop a plurality of scan lines.

In some embodiments, two adjacent transducer elements on a row of the one or more rows are addressed together and wherein a transducer of the plurality of transducer elements comprises a top section, a central section, and a bottom section, each of which comprise a first number of rows and a second number of columns for the ultrasonic pulse transmission and reception of the reflected ultrasonic signal. The ultrasonic pulse transmission and reception of the reflected ultrasonic signal from the sections are used for focusing the reflected ultrasonic signal in an azimuth direction using a first beamformer. The elevation focus is achieved using a second beamformer. For imaging using a B mode, a receive channel is assigned to two transducer elements on a same row, one of the two transducer elements from the top section and the other of the two elements from the bottom section, and another channel is assigned to two transducer elements of the central section.

In some embodiments, 2N receive channels are used to address N columns.

In some embodiments, all of the plurality of transducer elements selected electronically are operated on to generate pressure with elevation focus in a transmit operation. In a receive operation, all of the plurality of transducer elements separately electronically selected are used to reconstruct an image with focusing in the azimuth direction and an elevation plane.

In some embodiments, the ultrasonic imaging system further comprises a control circuit configured to electrically control relative delays along a column to be a summation of a linear delay and an arbitrary fine delay.

In some embodiments, the linear delay and arbitrary fine delays of the column are independent from other linear delay and arbitrary fine delays of other columns of the transducer, thereby allowing for arbitrary steering and focusing in three dimensions.

In some embodiments, each transducer element exhibits multiple modes of vibration, where only one mode of vibration is triggered when input stimulus is bandlimited to be less than frequencies of adjacent modes.

In some embodiments, each transducer element exhibits multiple modes of vibration, where frequencies generated from a first mode of vibration overlaps those from a second mode of vibration.

In some embodiments, each transducer element exhibits multiple modes of vibration simultaneously when driven by a wide band frequency input that includes center frequencies.

In an aspect, an ultrasonic imaging system comprising an ultrasonic transducer is disclosed. The transducer comprises a bias voltage. The transducer also comprises a column of transducer circuits. The transducer circuit comprises a transducer element, comprising a transducer for converting an electrical signal into an ultrasonic wave. The transducer element has a first terminal and a second terminal. The transducer also comprises a circuitry comprising an input drive device for supplying a potential to the transducer element, connected to the first terminal of the transducer element. The transducer also comprises an inductor connected to the second terminal of the transducer element. The transducer also comprises and a switch for connecting the transducer circuit to the bias voltage.

In some embodiments, the ultrasonic transducer is a pMUT device.

In some embodiments, the ultrasonic transducer is a cMUT device or a bulk piezo transducer.

In some embodiments, the ultrasonic imaging system further comprises a switch connected in parallel with the inductor, for the purpose of shorting the inductor.

In some embodiments, the ultrasonic imaging system comprises a plurality of columns.

In some embodiments, a column of the plurality of columns contains an inductor connected in series with the transducer element.

In some embodiments, the ultrasonic imaging system further comprises a switch connected in parallel with the inductor, for the purpose of shorting the inductor.

In some embodiments, the ultrasonic imaging system further comprises an inductor connected in series between the plurality of columns of transducer circuits and the bias voltage.

In some embodiments, the transducer element is configured to transmit a signal including a delay.

In some embodiments, the one or more transducer elements on the column operate with different delays.

In some embodiments, the delay for an element indexed by a row and a column is calculated by summing a delay for the column with a delay for the row.

In some embodiments, a delay profile comprising delays from one or more transducer elements with a common column index is symmetrical.

In some embodiments, the delay is a summation of a coarse delay and a fine delay.

In some embodiments, the coarse delay is linear between one or more adjacent transducer elements.

In some embodiments, the delay for a transducer element with a column index and a row index is a summation of a column delay, a linear coarse row delay, and a fine row delay.

In an aspect, a method for increasing a pressure of an ultrasonic wave emitted by a transducer comprising at least one transducer element. The method comprises using at least one transmit driver connected to the at least one transducer element, placing the at least one transducer element in a transmit mode. Each transducer element has a first terminal and a second terminal. The method also comprises for at least one inductor, connecting a first terminal of each of the at least one inductor to the second terminal of each transducer element. The second terminal of the at least one inductor is connected to a bias voltage. The at least one inductor is not integrated with the transducer element. The transducer also comprises connecting each of at least one transmit driver to each first terminal of each of the at least one transducer element.

In some embodiments, the at least one transducer element is a plurality of transducer elements organized in an array.

In some embodiments, the array is organized in rows and columns. The method further comprises electronically selecting a multiplicity of transducer elements in a column to define a column of transducer elements.

In some embodiments, a plurality of transducer elements in a row is selected electronically to define a row of transducer elements.

In some embodiments, a plurality of delays of transducer elements in a first column are independent from a plurality of delays of transducer elements in a second column and a plurality of delays of transducer elements in a first row are independent from a plurality of delays of pMUT transducer elements in a second row.

In some embodiments, transducer elements on a column have different delays.

In some embodiments, the method further comprises performing 3D imaging by applying a plurality of delays in an azimuth direction for a set to transmissions with a fixed steering angle in an elevation direction controlled by a plurality of delays applied to transducer elements on a column and repeating the sequence with different steering angles in an elevation plane and reconstructing an image using received echo from the transducer.

In some embodiments, the method further comprises performing volume imaging by focusing on an azimuth plane by varying a plurality of delays along an azimuth and also focusing or steering a beam in an elevation plane by varying a plurality of delays for a transducer on a column.

In some embodiments, the method further comprises selecting the bias voltage from a group consisting of ground, negative, and positive voltages.

INCORPORATION BY REFERENCE

All publications, patents, and patent applications mentioned in this specification are herein incorporated by reference to the same extent as if each individual publication, patent, or patent application was specifically and individually indicated to be incorporated by reference. Rathod, Vivek T. 2019. A Review of Electric Impedance Matching Techniques for Piezoelectric Sensors, Actuators, and Transducers. Lingvall, F., 2004. Time-domain Reconstruction Methods for Ultrasonic Array Imaging: A Statistical Approach.

BRIEF DESCRIPTION OF THE DRAWINGS

A better understanding of the features and advantages of the present subject matter will be obtained by reference to the following detailed description that sets forth illustrative embodiments and the accompanying drawings.

FIG. 6 shows dipole orientation in piezoelectric element herein on unpoled state and during poling and after poling.

FIGS. 10A and 10B show exemplary schematic diagrams of ultrasonic transducers that focuses in the elevation direction disclosed herein.

FIG. 11 shows an exemplary schematic diagram of an ultrasonic transducer with transducer elements that are organized on M rows and N columns, the transducer comprises of three strips that comprises of rows and/or columns, each of the strips can be selected to be driven separately and where columns in each strip share the same drive by transmit driver(s).

FIG. 21 shows elevation beamplots of a simulated 24×128 matrix array with 0° lateral steering (left) and 45° lateral steering.

FIG. 30 shows input/output signals of various circuits in an imaging assembly according to embodiments of the present disclosure.

FIG. 31A shows a plot of the amplitude of a transmit pressure wave in the frequency domain according to embodiments of the present disclosure.

FIG. 31B shows windows for apodization process according to embodiments of the present disclosure.

FIG. 35 illustrates multiple columns of piezo element circuits, of the type illustrated in FIG. 33A, without an inductor connected between the piezo elements and the X bias terminal.

DETAILED DESCRIPTION

Figure 1:
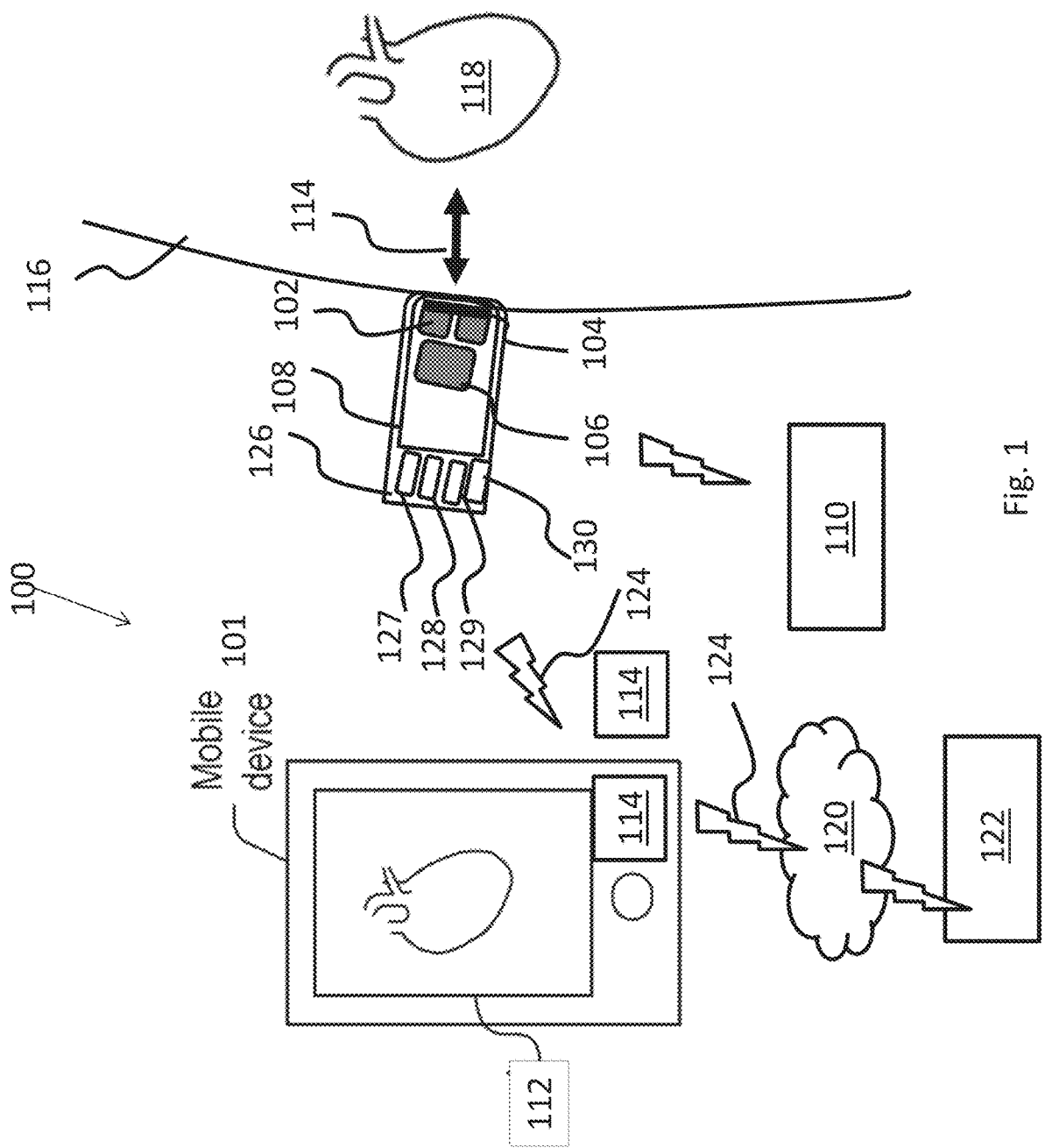
FIG. 1 shows an exemplary schematic diagram of an ultrasonic system herein including a transducer with a pMUT array used to transmit and receive ultrasonic beams, electronics to control pMUT array, other computational, control, and communication electronics, a display unit and a recording unit, with pMUT array directed at a target to be imaged.

Ultrasonic imaging traditionally has used bulk piezo electric films as a transducer. However, these tend to be expensive to use and also require high voltages to operate, typically in the 100 to 200V range. Recently, transducers capable of being mass produced on a silicon wafer using piezo films dispensed or sputtered on a silicon wafer substrate have become available. These have significant advantages with respect to their ability to integrate systems in a more compact or smaller form factor, with operating lower power requirements and cost compared to legacy systems. Additionally, other transducer technologies (such as cMUT) have emerged that may be manufactured on silicon wafers, to a significant manufacturing cost advantage. However, these transducers (as well as legacy transducers) may exhibit significant capacitive load to a transmit driver. For applications requiring significant pressure output, tuning the impedance of the circuit for maximum power transfer is employed. It is well known that power transfer is maximized when the impedance of the driver is a complex conjugate of the load. Legacy techniques have shown that use of an inductor between the driver and load has helped improve pressure outputs. However, this technique is not implementable for an integrated portable application or use case, due to size and parasitic impedance issues. A novel technique will be shown to achieve the integration needed at low cost and also to achieve pressure outputs desired. This technique is applicable to pMUTs and also other transducers with a significant capacitive load such as legacy bulk piezo and cMUTs (capacitive micromachined ultrasonic transducer). Further, a goal would be to implement this in a manner that enables the exceptional capabilities that are possible with use of 2D arrays of transducers and associated circuitry housed in or with ASICs. This enables both the generation of 3D images and electronic focusing in azimuth and elevation directions. Such capabilities have previously not been implemented successfully in handheld ultrasound imaging devices due to the cost, power and size constraints in legacy systems.

Traditionally, a 2D ultrasound image can be created by employing a variety of algorithms. One example of this is using relative delay for driving signals along the columns of piezoelectric elements in the azimuth direction. Beams can be focused in the azimuth direction electronically by altering electronically programmable delay applied to signal for different columns in the azimuth direction. However, focus in a direction orthogonal to the azimuth direction (e.g., the elevation direction) typically is achieved by using a mechanical lens. A mechanical lens may allow only one focus at a time, thus different elevation focus may require different design of the lens. Further, a fixed mechanical lens does not provide the focus required for 3D ultrasound imaging.

Disclosed herein in some embodiments are systems and methods configured for enabling low cost, low power, portable high resolution ultrasonic transducers and ultrasound imaging systems configured for ultrasonic imaging. Enabling these low cost, high performance systems can be dependent on using pMUTs that can be manufactured on a semiconductor wafer in high volume and low cost similar to high volume semiconductor processes. In exemplary embodiments, such pMUTs are arranged in a 2D array where each element in the array is connected to an electronic circuit, where the pMUT array and the circuit array are aligned together on different wafers and integrated together to form a tile, where each piezo element is connected to a controlling circuit element, where each piezo element may have 2 terminals as shown in FIG. 3. These pMUTs also may exhibit high bandwidth, making these transducers suitable for wideband imaging unlike prior art piezo bulk transducers. Additionally, existing transducers utilizing a mechanical lens for elevation focusing can also suffer attenuation losses in the lens, thereby reducing image quality. With the exemplary synthetic lenses herein, no mechanical lens is required. Sometimes, a slightly curved deep focus weak lens may be used or instead, a flat thin impedance matching layer can be used on top of the transducer. This may vastly improve attenuation losses.

The disclosed ultrasonic transducer may be a capacitive micromachined ultrasonic transducers (cMUT) device. Such a transducer may include a large array of cMUT elements. A cMUT array may provide larger bandwidth compared to other transducer technologies and may easily achieve high frequency operation.

Use of inductors is disclosed using fixed mechanical lenses. Additionally, imaging systems disclosed herein also use electronic lenses that advantageously eliminate the need to build a mechanical lens with a fixed focal length. Further, the electronic lenses disclosed herein allow great flexibility of being able to alter the focal length in the elevation plane and allow dynamic focus as a function of depth.

In an aspect, an ultrasonic imaging system comprising a transducer is disclosed. The transducer comprises at least one transducer element. Each transducer element has two terminals. The at least one transducer element is in a transmit mode. The transducer also comprises at least one transmit driver. The each transmit driver is connected to each first terminal of the at least one transducer element. The transducer also comprises at least one inductor comprising two terminals. Each first terminal of each inductor is connected to each second terminal of each transducer element. Each second terminal of each inductor is connected to a bias voltage.

In some embodiments, the transducer is a piezoelectric micro machined transducer (pMUT) device.

In some embodiments, the transducer is a capacitive micromachined ultrasonic transducer (cMUT) device or a bulk piezo transducer.

In some embodiments, the at least one transducer element is a plurality of transducer elements organized in an array.

In some embodiments, the array is organized in rows and columns. A plurality of transducer elements in a column is electronically selected to define a column of transducer elements.

In some embodiments, a plurality of transducer elements in a row is selected electronically to define a row of transducer elements.

In some embodiments, delays of transducer elements in a first column are independent from delays of transducer elements in a second column and delays of transducer elements in a first row are independent from delays of transducer elements in a second row.

In some embodiments, transducer elements on a column have different delays.

In some embodiments, the bias voltage is selected from a group consisting of ground, negative, and positive voltages.

In some embodiments, a bandwidth of the transducer is increased in a region of interest.

In some embodiments, at least one value of the at least one inductor is selected to provide a pressure output increase in a frequency range of interest.

In some embodiments, at least one value of the at least one inductor is chosen to be large enough to offset changes in phase introduced by at least one capacitance of the at least one transducer element.

In some embodiments, a bandwidth of the transducer is controlled by selecting a number of transducer elements on a column.

In some embodiments, a pressure output for the selected transducer elements is adjusted by changing a plurality of voltage drive levels of a plurality of transmit drivers of the selected transducer elements.

In some embodiments, the voltage drive levels are changed using a multilevel transmit drive pulse and selecting a desired digital drive level.

In some embodiments, the voltage drive levels are further controlled using pulse width modulation on a transmit pulsar waveform.

In some embodiments, the transducer is configured to provide electronic control of elevation focus in an elevation direction along the column.

In some embodiments, a transducer element along the column is driven by a multilevel pulse.

In some embodiments, a transducer element on a column is driven by a sequence of multilevel pulses.

In some embodiments, pulse magnitude, width, shape, pulse frequency, and combinations thereof of a multilevel pulse of the sequence of multilevel pulses are electrically programmable.

In some embodiments, a delay of an onset of the multilevel pulse is electrically programmable.

In some embodiments, the delay for an element indexed by a row and a column is calculated by summing a delay for the column with a delay for the row.

In some embodiments, a delay may be a summation of a coarse delay and a fine delay.

In some embodiments, the delay of pulse onset is programmable in an X direction.

In some embodiments, the delay of pulse onset is programmable in a Y direction.

In some embodiments, a shape of the multilevel pulse is selected from a group consisting of sinusoidal and digital square.

In some embodiments, the transmit driver is configured to drive the one or more transducer elements along a column. The transmit driver is driven by signals from a transmit channel. The signals of the transmit channel are delayed electronically relative to delay applied to other transmit channels driving other transducer elements on different columns.

In some embodiments, the one or more transducer elements along the column operate with substantially identical delays.

In some embodiments, the transmit channel and additional transmit channels are configured to electrically control relative delays between adjacent columns. The control circuit is configured to set relative delays for a first number of transducer elements on the columns such that the first number of transducer elements in a same row share substantially identical relative delays with a second number of transducer elements of a starting row.

In some embodiments, a transducer element of the plurality of transducer elements comprises a top section, a central section, and a bottom section, each of which comprise a number of rows and a number of columns for pulse transmission and reception of the reflected ultrasonic signal. The pulse transmission and reception of the reflected ultrasonic signal from the top section, central section, and bottom section is used for focusing the reflected ultrasonic signal in an azimuth direction using a first beamformer. An elevation focus is achieved using a second beamformer.

In some embodiments, a focal distance in an elevation direction is electronically programmed.

In some embodiments, the pulse transmission and reception of the reflected signal of the top section and the bottom section are performed simultaneously.

In some embodiments, the transducer elements perform parallel beamforming to develop a plurality of scan lines.

In some embodiments, two adjacent transducer elements on a row of the one or more rows are addressed together and wherein a transducer of the plurality of transducer elements comprises a top section, a central section, and a bottom section, each of which comprise a first number of rows and a second number of columns for the ultrasonic pulse transmission and reception of the reflected ultrasonic signal. The ultrasonic pulse transmission and reception of the reflected ultrasonic signal from the sections are used for focusing the reflected ultrasonic signal in an azimuth direction using a first beamformer. The elevation focus is achieved using a second beamformer. For imaging using a B mode, a receive channel is assigned to two transducer elements on a same row, one of the two transducer elements from the top section and the other of the two elements from the bottom section, and another channel is assigned to two transducer elements of the central section.

In some embodiments, 2N receive channels are used to address N columns.

In some embodiments, all of the plurality of transducer elements selected electronically are operated on to generate pressure with elevation focus in a transmit operation. In a receive operation, all of the plurality of transducer elements separately electronically selected are used to reconstruct an image with focusing in the azimuth direction and an elevation plane.

In some embodiments, the ultrasonic imaging system further comprises a control circuit configured to electrically control relative delays along a column to be a summation of a linear delay and an arbitrary fine delay.

In some embodiments, the linear delay and arbitrary fine delays of the column are independent from other linear delay and arbitrary fine delays of other columns of the transducer, thereby allowing for arbitrary steering and focusing in three dimensions.

In some embodiments, each transducer element exhibits multiple modes of vibration, where only one mode of vibration is triggered when input stimulus is bandlimited to be less than frequencies of adjacent modes.

In some embodiments, each transducer element exhibits multiple modes of vibration, where frequencies generated from a first mode of vibration overlaps those from a second mode of vibration.

In some embodiments, each transducer element exhibits multiple modes of vibration simultaneously when driven by a wide band frequency input that includes center frequencies.

In an aspect, an ultrasonic imaging system comprising an ultrasonic transducer is disclosed. The transducer comprises a bias voltage. The transducer also comprises a column of transducer circuits. The transducer circuit comprises a transducer element, comprising a transducer for converting an electrical signal into an ultrasonic wave. The transducer element has a first terminal and a second terminal. The transducer also comprises a circuitry comprising an input drive device for supplying a potential to the transducer element, connected to the first terminal of the transducer element. The transducer also comprises an inductor connected to the second terminal of the transducer element. The transducer also comprises and a switch for connecting the transducer circuit to the bias voltage.

In some embodiments, the ultrasonic transducer is a pMUT device.

In some embodiments, the ultrasonic transducer is a cMUT device or a bulk piezo transducer.

In some embodiments, the ultrasonic imaging system further comprises a switch connected in parallel with the inductor, for the purpose of shorting the inductor.

In some embodiments, the ultrasonic imaging system comprises a plurality of columns.

In some embodiments, a column of the plurality of columns contains an inductor connected in series with the transducer element.

In some embodiments, the ultrasonic imaging system further comprises a switch connected in parallel with the inductor, for the purpose of shorting the inductor.

In some embodiments, the ultrasonic imaging system further comprises an inductor connected in series between the plurality of columns of transducer circuits and the bias voltage.

In some embodiments, the transducer element is configured to transmit a signal including a delay.

In some embodiments, the one or more transducer elements on the column operate with different delays.

In some embodiments, the delay for an element indexed by a row and a column is calculated by summing a delay for the column with a delay for the row.

In some embodiments, a delay profile comprising delays from one or more transducer elements with a common column index is symmetrical.

In some embodiments, the delay is a summation of a coarse delay and a fine delay.

In some embodiments, the coarse delay is linear between one or more adjacent transducer elements.

In some embodiments, the delay for a transducer element with a column index and a row index is a summation of a column delay, a linear coarse row delay, and a fine row delay.

In an aspect, a method for increasing a pressure of an ultrasonic wave emitted by a transducer comprising at least one transducer element is disclosed. The method comprises using at least one transmit driver connected to the at least one transducer element, placing the at least one transducer element in a transmit mode. Each transducer element has a first terminal and a second terminal. The method also comprises for at least one inductor, connecting a first terminal of each of the at least one inductor to the second terminal of each transducer element. The second terminal of the at least one inductor is connected to a bias voltage. The at least one inductor is not integrated with the transducer element. The transducer also comprises connecting each of at least one transmit driver to each first terminal of each of the at least one transducer element.

In some embodiments, the at least one transducer element is a plurality of transducer elements organized in an array.

In some embodiments, the array is organized in rows and columns. The method further comprises electronically selecting a multiplicity of transducer elements in a column to define a column of transducer elements.

In some embodiments, a plurality of transducer elements in a row is selected electronically to define a row of transducer elements.

In some embodiments, a plurality of delays of transducer elements in a first column are independent from a plurality of delays of transducer elements in a second column and a plurality of delays of transducer elements in a first row are independent from a plurality of delays of pMUT transducer elements in a second row.

In some embodiments, transducer elements on a column have different delays.

In some embodiments, the method further comprises performing 3D imaging by applying a plurality of delays in an azimuth direction for a set to transmissions with a fixed steering angle in an elevation direction controlled by a plurality of delays applied to transducer elements on a column and repeating the sequence with different steering angles in an elevation plane and reconstructing an image using received echo from the transducer.

In some embodiments, the method further comprises performing volume imaging by focusing on an azimuth plane by varying a plurality of delays along an azimuth and also focusing or steering a beam in an elevation plane by varying a plurality of delays for a transducer on a column.

In some embodiments, the method further comprises selecting the bias voltage from a group consisting of ground, negative, and positive voltages.

Certain Definitions

Unless otherwise defined, all technical terms used herein have the same meaning as commonly understood by one of ordinary skill in the art to which the present subject matter belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by about 10%, 5%, or 1%, including increments therein.

In some embodiments, the imagers (interchangeably here as "transducers") herein can be used to perform but is not limited to perform: 1D imaging, also known as A-Scan, 2D imaging, also known as B scan, 1.5D imaging, 1.75D imaging, 3D and Doppler imaging. Also, the imager herein can be switched to various imaging modes which are pre-programmed. Also, biplane imaging mode may be implemented using transducers herein.

In some embodiments, transducer elements herein (e.g., pMUT elements, cMUT elements) are interchangeable with transceiver elements. Specifically, pMUT elements herein are interchangeable with piezoelectric elements and piezo elements. In some embodiments, the transducer element herein may include one or more of: a substrate, a membrane suspending from the substrate; a bottom electrode disposed on the membrane; a piezoelectric layer disposed on the bottom electrode; and one or more top electrodes disposed on the piezoelectric layer.

FIG. 1 shows an exemplary embodiment of the ultrasonic imaging system 100 disclosed herein. In this embodiment, the image system includes a portable device 101, the device 101 having a display unit 112, a data recording unit 114 with connection enabled by communication interface to a network 120 and external databases 122, such as electronic health records. Such connection to external data sources may facilitate medical billing, data exchange, inquiries or other medical related information communication. In this embodiment, the system 100 includes an ultrasonic imager (interchangeable as "probe" herein) probe 126 which includes ultrasonic imager assembly (interchangeably as "tile assembly" herein) 108, where the ultrasonic tile has one or more arrays of pMUTs 102 fabricated on a substrate. The array(s) of pMUTs 102 are configured to emit and receive ultrasonic waveforms under an electronic control unit, e.g., an application specific integrated circuit (ASIC), 106 located on the imager and another control unit 110.

In this particular embodiment, the display unit 112 and/or at least part of the electronic communication control unit in 110 may be located on the assembly 108. In some embodiments, the display unit 112 or part of the control unit 110 could be external to the imager but connected to the ultrasonic imager assembly 108 and its elements therewithin with a communication interface 124, which can be a wired communication interface and/or a wireless communication interface. For wired connections, many protocols for data interchange such as USB2, Lightning and others can be used. Similarly, for wireless communications, a commonly used protocol such IEEE 802.11 (Wi-Fi) or other wireless communication protocols can be used. Similarly, the data recording unit 114 can also be external to the probe and can also communicate with probe 126 using wireless communication interface or wired communication interface. In some embodiments, the display 112 may have an input device, e.g., touch screen, a user-friendly interface, e.g., graphical user interface (GUI), to simplify user interaction.

In the same embodiment, the pMUT array 102 is coupled to an application specific integrated circuit (ASIC) 106 located on another substrate and in close proximity to the pMUT array 102. The array may also be coupled to impedance lowering and/or impedance matching material 104 which can be placed on top of the pMUT array. In some embodiments, the imager 126 includes a rechargeable power source 127 and/or a connection interface 128 to an external power source, e.g., a USB interface. In some embodiments, the imager 126 includes an input interface 129 for an ECG signal for synchronizing scans to ECG pulses. In some embodiments, the imager 126 has an inertial sensor 130 to assist with user guidance.

Conventional transducer arrays use piezoelectric material, e.g., lead zirconate titanate (PZT) formed by dicing a block of bulk PZT to form individual piezo elements. These tend to be expensive. In contrast, pMUT arrays disclosed herein are disposed on a substrate (e.g., wafer). The wafer can be in various shapes and/or sizes. As an example, the wafer herein can be of sizes and shapes of wafers in semiconductors processes used for building integrated circuits. Such wafers can be produced in high volume and with low cost. Exemplary wafer sizes are: 6, 8 and 12 inches in diameter.

In some embodiments, many pMUT arrays can be batch manufactured at low cost. Further, integrated circuits can also be designed to have dimensions such that connections needed to communicate with pMUTs are aligned with each other and pMUT array (102 of FIG. 1) can be connected to a matching integrated circuit (106) in close proximity, typically vertically below or proximal to the array by a distance, e.g., around 25 µm to 100 µm. In some embodiments, the combination of 102, 104, and 106 is referred to as an imaging assembly 108 or a tile, as shown in FIG. 1. For example, one exemplary embodiment of the assembly 108 can have 1024 pMUT elements, connected to a matching ASIC that have the appropriate number of transmit and receive functionality for 1024 piezoelectric elements. The array size is not limited to 1024. It can be smaller or larger. Larger sizes of pMUT elements can also be achieved by using multiple pMUT arrays 102, along with multiple matching ASICs, 106 and assembling them adjacent to each other and covering them with appropriate amounts of impedance matching material 104. Alternately, a single array can have large number of pMUT elements arranged in rectangular arrays or other shapes with a number of pMUT elements ranging from less than 1000 to 10,000. The pMUT array and the plurality of pMUT elements can be connected to matching ASICs.

The arrow 114 shows ultrasonic transmit beams from the imager assembly 108 targeting a body part 116 and imaging a target 118. The transmit beams are reflected by the target being imaged and enters the imager assembly 108 as indicated by arrow 114. In addition to ASIC 106, the imaging system 100 may include other electronic control, communication and computational circuitry 110. It is understood that the ultrasonic imager 108 can be one self-contained unit as shown in FIG. 1, or it may include physically separate, but electrically or wirelessly connected elements, such as part of the electronic control unit 110. An example of this is shown in FIG. 2.

Figure 2:
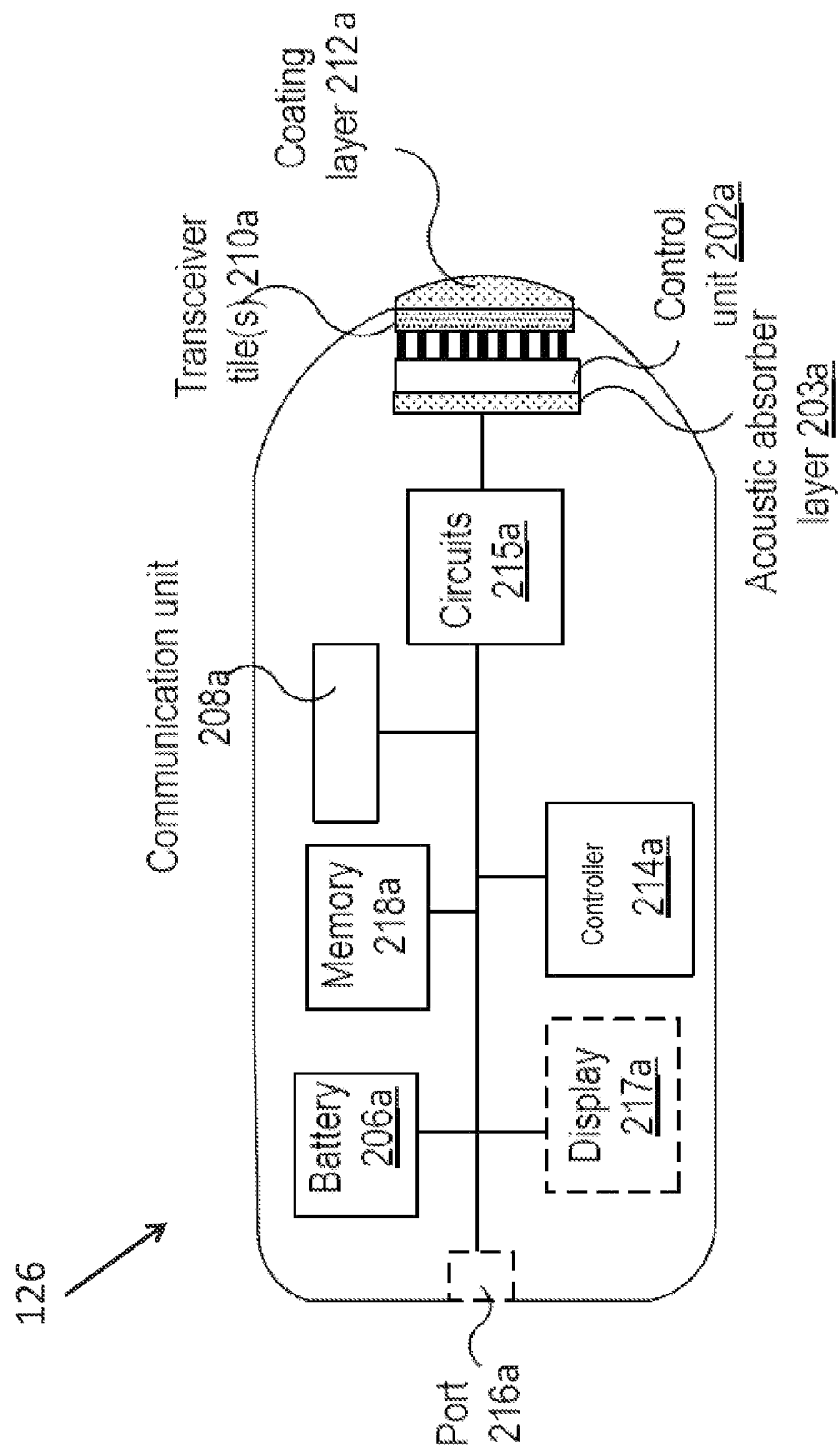
FIG. 2 shows an exemplary schematic diagram of an ultrasonic transducer here.

FIG. 2 shows a schematic diagram of the imager 126 according to embodiments of the present disclosure. As depicted in FIG. 2, the imager 126 may include: a transceiver array 210a for transmitting and receiving pressure waves; a coating layer 212a that operates as a lens for steering the propagation direction of and/or focusing the pressure waves and also functions as an impedance interface between the transceiver array and the human body; the lens 202 may also cause attenuation of the signal exiting the transducer and also entering the transducer and therefore it is also desirable to keep this to a minimum; when elevation control is electronic, this lens may not be needed and can be replaced by a thin protective impedance matching layer only, where losses are only minimal; a control unit 202a, such as ASIC chip (or, shortly ASIC), for controlling the transceiver array 210a and coupled to the transducer array 210a by bumps. The combination of the transceiver array with the ASIC connected to it consists of a tile. Controllers 214a, which may be, for example, Field Programmable Gate Arrays (FPGAs) for controlling the components of the imager 126, a circuit(s) 215a, such as Analog Front End (AFE), for processing/conditioning signals; an acoustic absorber layer 203 for absorbing waves that are generated by the transducer tiles 210a and propagate toward the circuit 215a. In certain embodiments the acoustic absorber layer is located in between the transducer and the ASIC; in certain embodiments, these acoustic absorber layers are not needed; a communication unit 208a for communicating data with an external device, such as the device 101, through one or more ports 216a; a memory 218a for storing data; a battery 206a for providing electrical power to the components of the imager; and optionally a display 217a for displaying images of the target organs.

When using the imager, for example to image human or animal body part the transmitted ultrasonic waveform is directed towards the target. Contact with the body is achieved by holding the imager in close proximity of the body, usually after a gel is applied on the body and the imager placed on the gel, to allow superior interface of ultrasonic waves being emitted to enter the body and also for ultrasonic waveforms reflected from the target to reenter the imager, where the reflected signal is used to create an image of the body part and results displayed on a screen, including graphs, plots, statistics shown with or without the images of the body part in a variety of formats.

It should be noted that the probe 126 may be configured with certain parts being physically separate, yet connected through a cable or wireless communications connection. As an example, in this particular embodiment, the pMUT assembly and the ASIC and some control and communications related electronics could reside in a unit often called a probe. The part of the device or probe that contacts the body part contains the pMUT assembly.

Figure 3A:
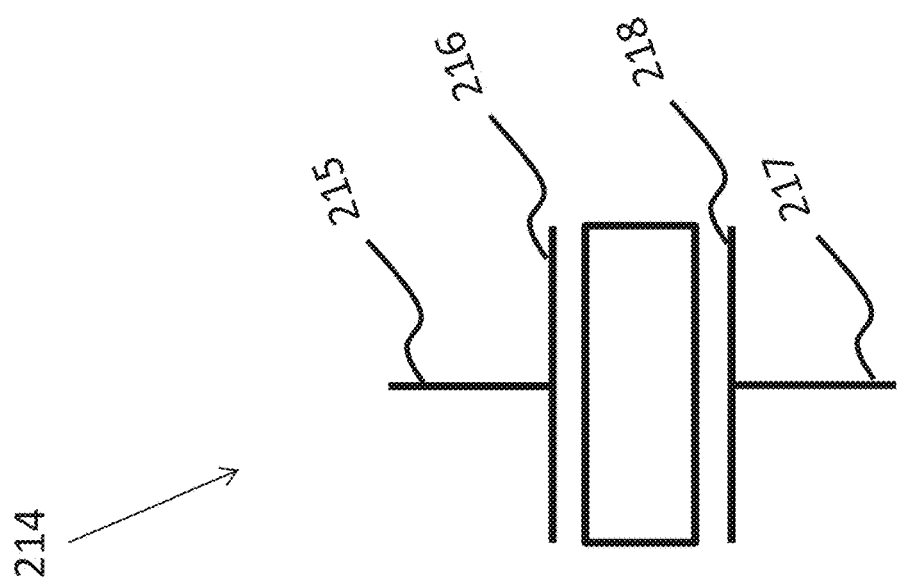
FIG. 3A shows an exemplary schematic diagram of a piezoelectric micro machined transducer (pMUT) element with 2 conductors.

FIG. 3A shows a cross section of a schematic diagram of a conventional piezoelectric element 214. In this embodiment, the piezoelectric element has 2 electrodes, the first electrode 216 is connected to a signal conductor 215 and the second electrode 218 is connected to a second conductor 217 which can be commonly connected to ground or other DC potential.

Piezoelectric elements have been used for decades for ultrasonic medical imaging. However, the piezoelectric element can be thick, for example, approaching around 100 µm and typically may require +100V to −100V alternating current (AC) drive across it to create an ultrasonic pressure wave of sufficient strength to enable medical imaging. The frequency of this AC drive signal may be around the resonating frequency of the piezoelectric structures and can be above 1 MHz for medical imaging applications.

In some embodiments, the power dissipated in driving the piezoelectric element is proportional to $C*V^2$, where C is capacitance of the piezo element and V is the maximum voltage across the piezoelectric layer. When transmitting, a multiplicity of piezoelectric elements can be driven together with somewhat different delay to focus a beam or to steer a beam. The simultaneous drive of many elements can cause temperature to rise on the surface of the elements. It is highly desirable or required not to exceed a threshold temperature so as not to injure the subject being imaged. Thus, this threshold temperature limits the number of elements that can be driven and the time period for which they can be driven.

Disclosed herein, in some embodiments, the piezoelectric elements are much thinner, approximately 1 to 5 µm thick, compared to around 100 µm thickness of conventional bulk piezo elements. Such large decrease in thickness may enable use of lower voltage drive signals for the piezoelectric elements to maintain electric field strength similar to conventional elements. For example, the piezoelectric elements disclosed herein may require drive voltages ranging from around 5V to 20V peak to peak.

The capacitance of the piezo element may also be increased by the reduction in thickness for certain piezoelectric materials. Thus, as an example, when drive voltage decreases from 100 V to 10 V when driving 10× times thinner film, capacitance may increase by a factor of 10 for the thinner piezoelectric materials, and power dissipation may be reduced by a factor of 10. This reduction in power dissipation also can reduce heat generation and temperature rise in the imaging probe. Thus, using lower drive voltages, the temperature of the pMUT surface can be lowered.

In some embodiments, for a given temperature, when using low voltage pMUTs, more pMUT elements can be driven to illuminate a larger area. This may allow faster scanning of the target, especially if multiple emissions are needed to scan an entire target to form an image. Often, a target area may be scanned with multiple emissions using different steering angles and image data combined to obtain a higher quality image.

It may also be desirable to image at a high frame rate. A frame rate measures how many times a target is imaged per minute. It is desirable to image at a high frame rate, when tissue motion is involved to observe targets moving without image blurring. In some embodiments, the ability to drive more piezoelectric elements enables more coverage of the transducer aperture per emission, minimizing the number of emissions needed to cover entire aperture, thus increasing frame rates.

In some embodiments, image quality can be improved by combining several frames of images into one resultant lower noise frame. However, this can reduce frame rate. When using low power pMUT with higher frame rate compared with that of the conventional piezo films, for a given rise in pMUT temperature, this averaging technique can be used due to low voltage pMUTs having lower power thus enabling inherently higher starting frame rates. In some embodiments, a synthetic aperture method of ultrasound imaging can be used to allow compounding of images.

In some embodiments, the ability of drive more piezoelectric elements at a time improves signal to noise ratio (SNR) and enables better quality of the reconstructed image.

Further, as noted in FIG. 1, an ASIC 106 is coupled to the pMUT 102. The ASIC can contain low noise amplifiers (LNA). The pMUTs are connected to the LNA in receive mode through switches. The LNA converts the electrical charge in the pMUT generated by a reflected ultrasonic beam exerting pressure on the pMUT, to an amplified voltage signal with low noise. The signal to noise ratio of the received signal can be among the key factors that determine the quality of the image being reconstructed. It is thus desirable to reduce inherent noise in the LNA itself. This can be achieved by increasing the transconductance of the input stage of the LNA. This can be achieved for example by using more current in the input stage. More current may cause power dissipation and heat to increase. However, in cases where low voltage pMUTs are used, with ASIC in close proximity, the power saved by the low voltage pMUTs can be utilized to lower noise in the LNA for a given total temperature rise acceptable when compared to transducers operated with high voltage.

Figure 3B:
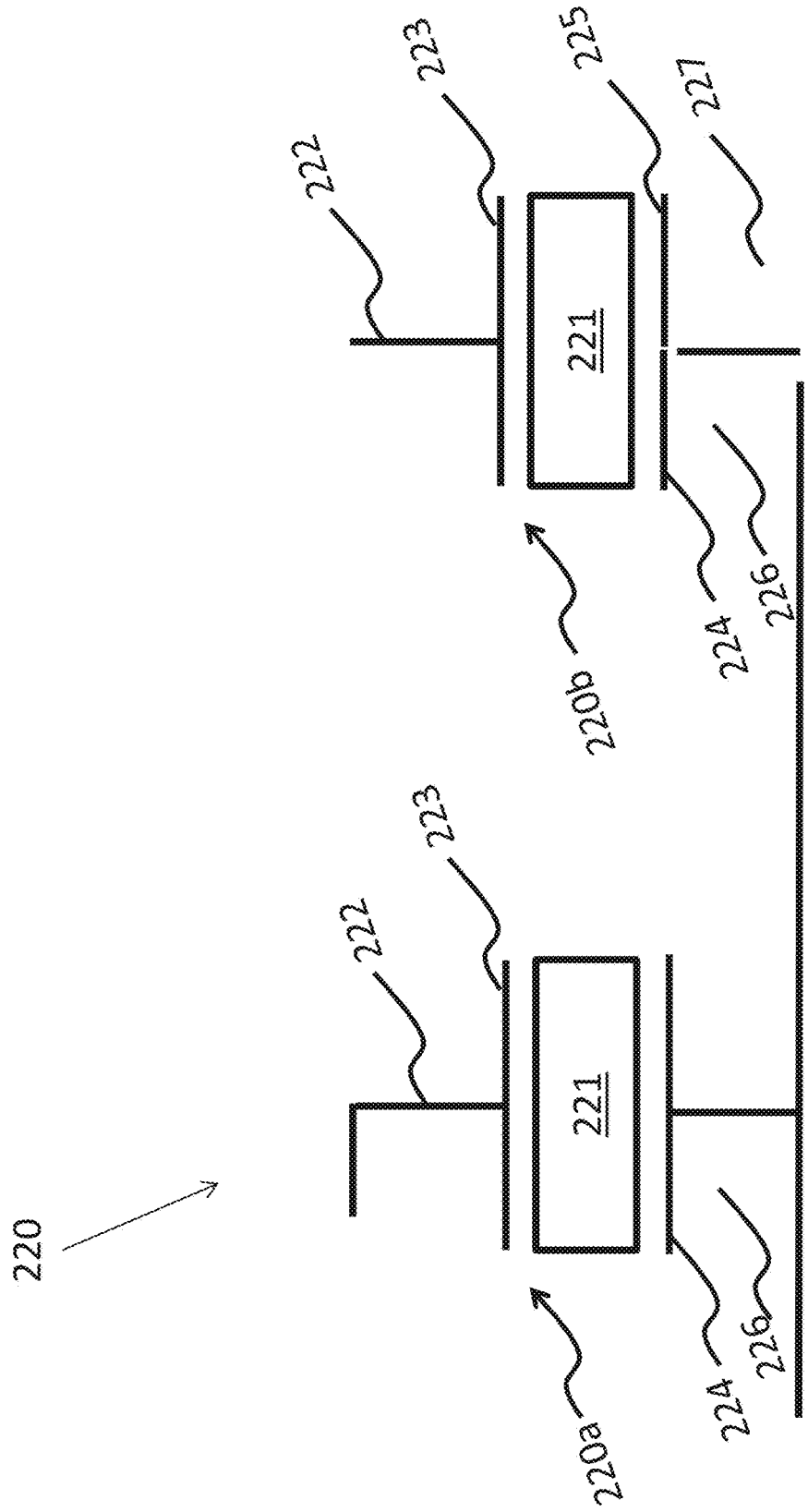
FIG. 3B shows an exemplary schematic diagram of a pMUT element comprising two sub elements, each sub elements with 2 or more electrodes.

FIG. 3B shows a schematic diagram of a pMUT element 220 disclosed herein. It consists of 2 subelements 220a and 220b. Subelement 220a, in this embodiment, has a piezoelectric layer 221, with a first electrode 223, connected to first conductor 222 and a second electrode 224 connected to a second conductor 226. Subelement 220b has a first electrode 228 connected to first conductor 229 and second electrode 225 connected to second conductor 227. Typically, the second conductors of both subelements are connected together and connected to a bias voltage.

Figure 3C:
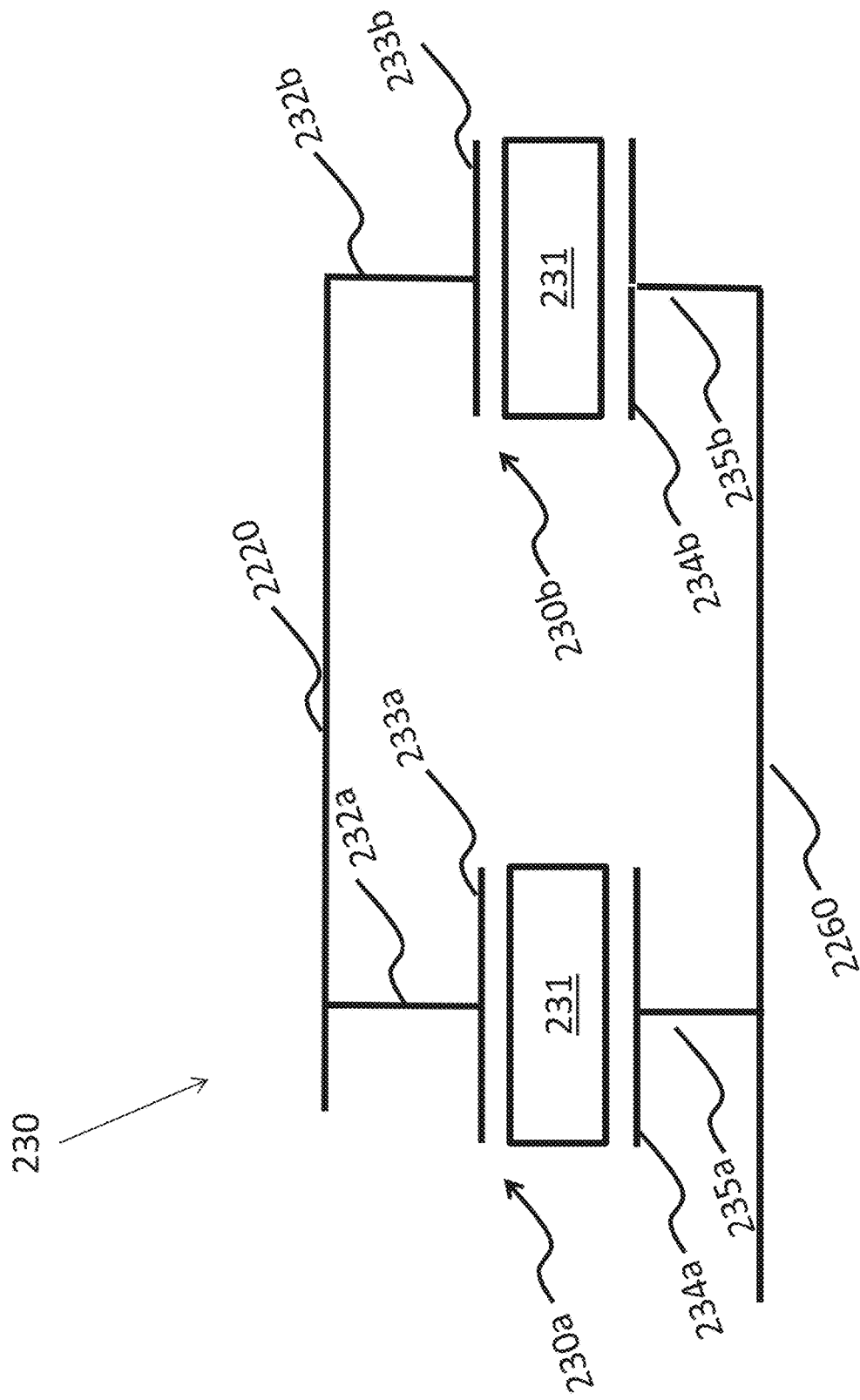
FIG. 3C shows an exemplary schematic of a pMUT element with 2 sub elements, each sub element with 2 electrodes, wherein the first electrode of first sub element is connected to one of the electrodes of the second element and the second electrode of the first element connected to the remaining electrode of the second sub element.

FIG. 3C is a schematic diagram of a pMUT element 230 with 2 sub elements 230a, 230b. In some embodiments, each pMUT element includes one or more sub elements. Each sub element, in this embodiment, has a piezoelectric layer 231, with a first electrode 233a, connected to first conductor 232a and a second electrode 234a connected to a second conductor 235a, where the first conductors of all sub elements are connected together by connection 2220 and second conductors of all sub elements are connectors connected together by connection 2260. A second subelement 230b has piezoelectric layer 231 with a first electrode 233b connected to first conductor 232b and a second electrode 234b connected to second conductor 235b.

In some embodiments, an element may consist of more than 2 subelements, where the first electrode of all subelements are connected together, typically to a drive signal and the second electrode of all subelements are also connected together, typically to a bias voltage.

Figure 4:
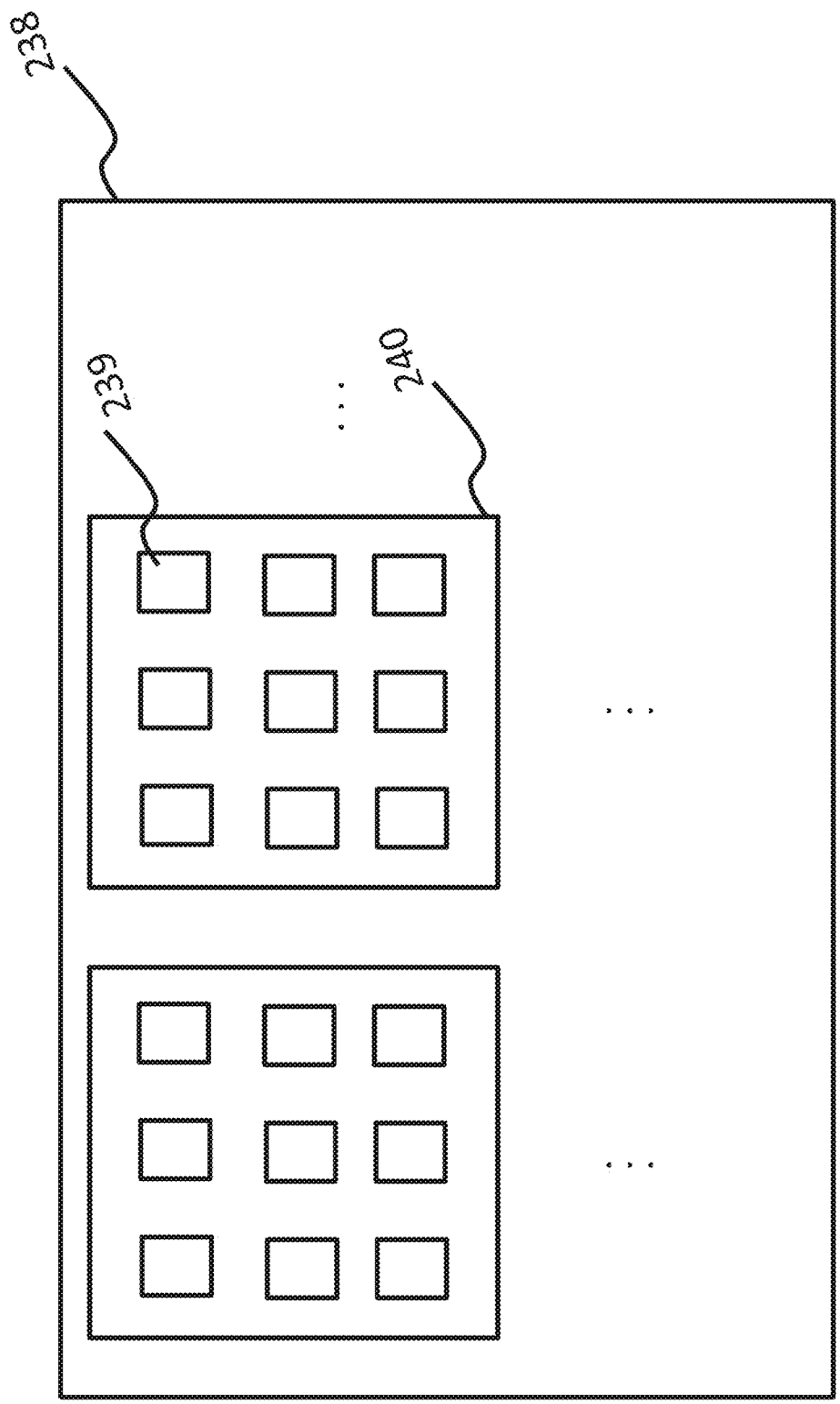
FIG. 4 shows an exemplary diagram of the pMUT array of an ultrasonic transducer system herein.

FIG. 4 shows a substrate 238, on which a plurality of piezoelectric micro machined ultrasound transducer (pMUT) array elements 239 are arranged. In this embodiment, one or more array elements form a transceiver array 240, and more than one transceiver array are included on the substrate 238.

Figure 5:
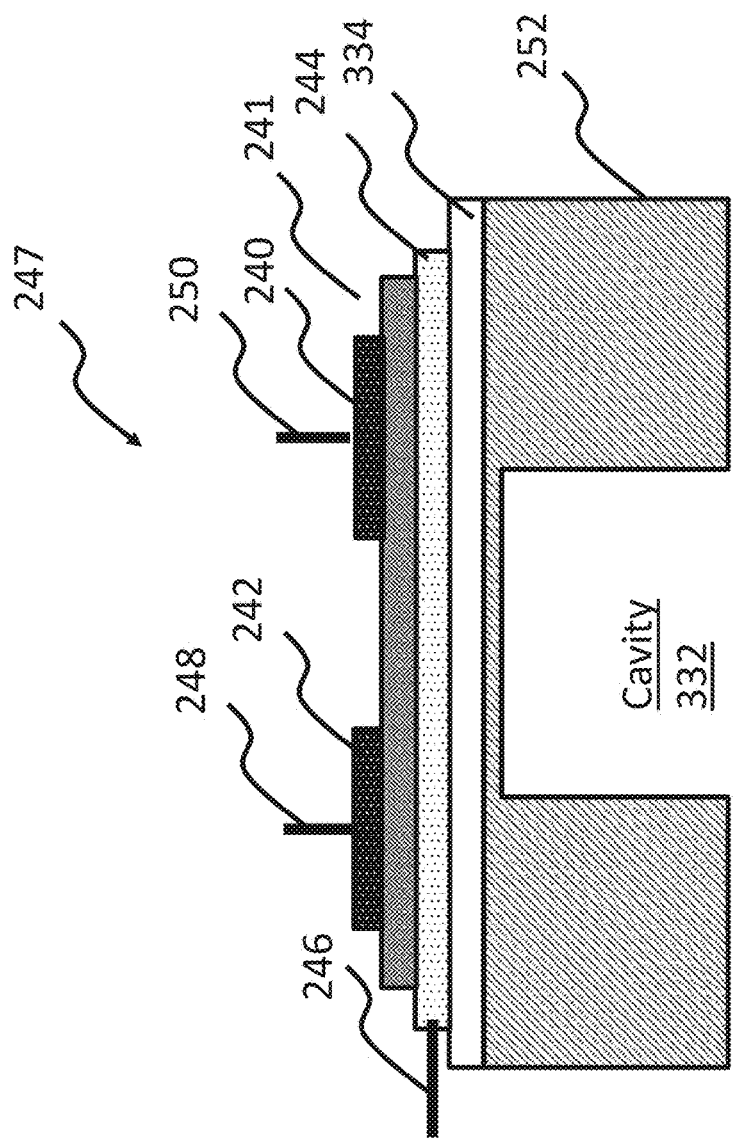
FIG. 5 shows an exemplary cross-section of a piezoelectric element of the pMUT array herein.

FIG. 5 shows a cross section of an exemplary embodiment of a piezoelectric element 247. In this embodiment, the element 247 has a thin piezoelectric film 241, disposed on a substrate 252. The piezoelectric film has a first electrode 244 that is connected to a signal conductor 246. This electrode is typically deposited on the substrate on which SiO2 is grown. A layer of TiO2 followed by platinum is deposited on which PZT is sputtered or a PZT sol gel is applied to develop a thin layer of PZT as the piezoelectric film 241. This and the first metal electrode are patterned by etches to the shape desired. The signal conductor 246 is connected to the first electrode. A second electrode 240 is grown above the thin film 241 and connected to a second conductor 250. A third electrode 242 is also grown adjacent to the second electrode but electrically isolated from it. A third conductor 248 is connected to the third electrode. The actual layout of the electrodes shown can vary from square to rectangular, elliptical and so forth adjacent electrodes or annular electrodes, with an electrode surrounding another. The piezoelectric film can have different shapes and can be present in certain portions over the substrate and cavity.

Due to non-symmetry in the crystalline structure of PZT, an electrical polarity develops, creating electric dipoles. In a macroscopic crystalline structure, the dipoles by default can be found to be randomly oriented, for example as shown in FIG. 6 on the left. When the material is subjected to a mechanical stress, each dipole can rotate from its original orientation toward a direction that minimizes the overall electrical and mechanical energy stored in the dipole. If all the dipoles are initially randomly oriented (i.e., a net polarization of zero), their rotation may not significantly change the macroscopic net polarization of the material, hence the piezoelectric effect exhibited may be negligible. Therefore, it is important to create an initial state in the material such that most dipoles may be more-or-less oriented in the same direction. Such an initial state can be imparted to the material by poling it. The direction along which the dipoles align is known as the poling direction. Orientation of dipoles during and after poling is shown in FIG. 6 (middle and right panels).

Piezoelectric thin films therefore may need to be poled initially before being used. This can be accomplished when the film is sputtered under a field. This can also be done post fabrication by applying a high voltage across the film, typically at high temperature (e.g., 175° C.) for some time (e.g., 1-2 minutes or more). In the piezo element of FIG. 3, a pMUT can be built with 2 terminals and a high voltage can be applied for example across 216 and 218. This high voltage can be around 15 V for a 1 µm thick piezo film. Such a voltage is sufficient for poling.

Prior art pMUTs or other piezo elements from bulk PZT typically have two electrodes. As disclosed herein, the piezoelectric element may have 2 (in FIG. 3) or more electrodes, as shown in FIG. 5. In FIG. 5, the first conductor during poling can be tied to ground potential, while the second conductor is tied to a negative potential, say −15V for a 1 µm thick PZT film, and the third electrode is tied at +15V for some time at high temperature. This can create 2 poling directions across the PZT film that are opposite for piezo film between first and second conductors as compared to piezo film between first and third conductors. After poling is complete, during transmission or receiving operation, the second and third conductors can be connected to ground or a bias voltage, while the first conductor is connected to an ASIC to be driven by a transmit driver during transmit operation or is connected to a LNA through switches during receive operation. The second and third conductor can also be tied to a non-zero DC bias, where the bias values can be different.

The piezoelectric element in an exemplary embodiment utilizes transverse strain, leveraging PZT transverse strain constant d31, the piezoelectric coefficient, to create movement of a membrane or convert movement of a membrane into charge. The PZT element of FIG. 5 with orthogonal poling directions to the film, in transmit operation amplifies movement of the membrane for a given drive compared to a structure shown in FIG. 3A with only one poling direction for the film. Thus transmit sensitivity can be improved, allowing larger movement of the membrane per volt of applied transmit drive.

In receive mode, the orthogonal poling direction may create more charge to be sensed by a LNA. The LNA connections are shown symbolically in FIG. 7. Not all elements in the path of connecting the piezo element to the LNA are shown for simplicity. Piezoelectric element 260, in certain embodiments, has first electrode 274 connected to a switch in series with LNA 268, connected by conductor 262. The second electrode of 260 is 266 and may be connected to a DC bias that includes 0 V (ground). 270 represent a reflected ultrasonic beam striking the pMUT element 260 and create charge across electrodes 266, 274. It is to be noted that the LNA can be designed to operate in voltage or charge mode. pMUTs may tend to have large capacitance and for a given amount of charge will create a lower voltage across the transducer than for PZT bulk element with much smaller capacitance if voltage sensing is used, where the voltage on the transducer is amplified. Since the voltage at input of LNA is small, output is noisier. Charge amplification can provide better signal to noise ratio at the output of the LNA due to high capacitance of pMUT elements compared to voltage mode operation, especially when pMUTs produce more charge output for a given input pressure in receive mode. This is explained in FIG. 7, where any charge received by Ct is transferred across a much smaller capacitor Cf creating a bigger voltage at output of LNA 272. These LNAs are also designed so that they power up or down rapidly.

Traditional 2D imaging is done using columns of elements that are arranged in a rectangular shape. Alternately, 2D imaging may be achieved by taking many smaller elements arranged in a column. Individual array elements may be combined to act as a single larger 1D array element to make up a column. This is achieved by hardwiring these individual elements, to create a larger element which has one signal conductor and a common ground conductor. Transmit drive, receive sense and control are implemented for this one combined and larger two-lead pMUT.

Figure 8A:
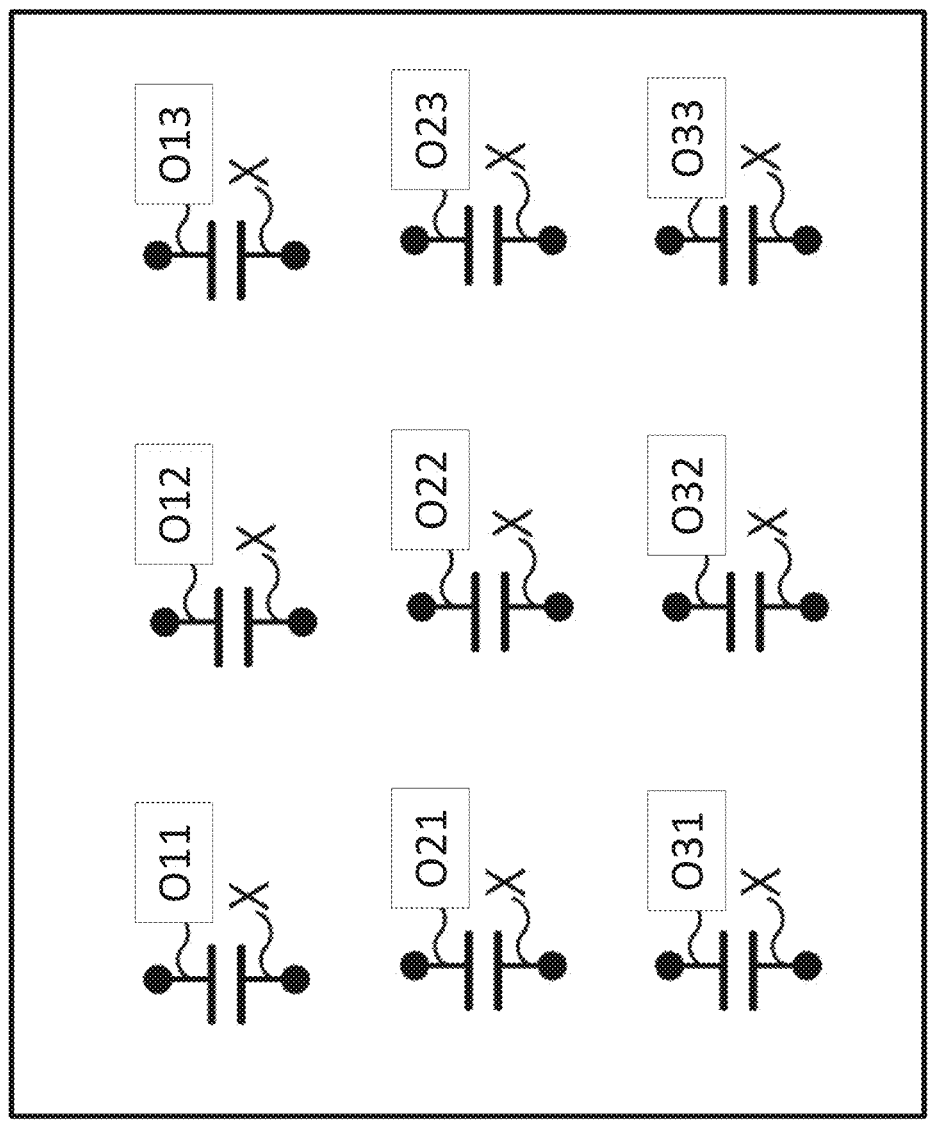
FIG. 8A shows an exemplary embodiment of a 2D array of pMUTs with one common ground or biasing electrode for electrically adjustable line transducers in which lines can be in vertical or horizontal direction and size of lines (e.g., number of pMUT element in a line) can be electrically programmable.

FIG. 8A shows the schematic diagram of an exemplary embodiment of the ultrasonic imaging array 300 of a transducer herein. The array is shown with 9 pMUT elements, arranged in 3 rows and 3 columns or 3 by 3, for the purpose of illustration. It is understood that in practice the array size can be various sizes larger or smaller as needed. Non-limiting example of the sizes include: 32 by 32, 32 by 64, 32 by 194, 12 by 128, 24 by 128, 32 by 128, 64 by 128, 64 by 32, 64 by 194 (columns by rows or rows by columns).

Figure 8B:
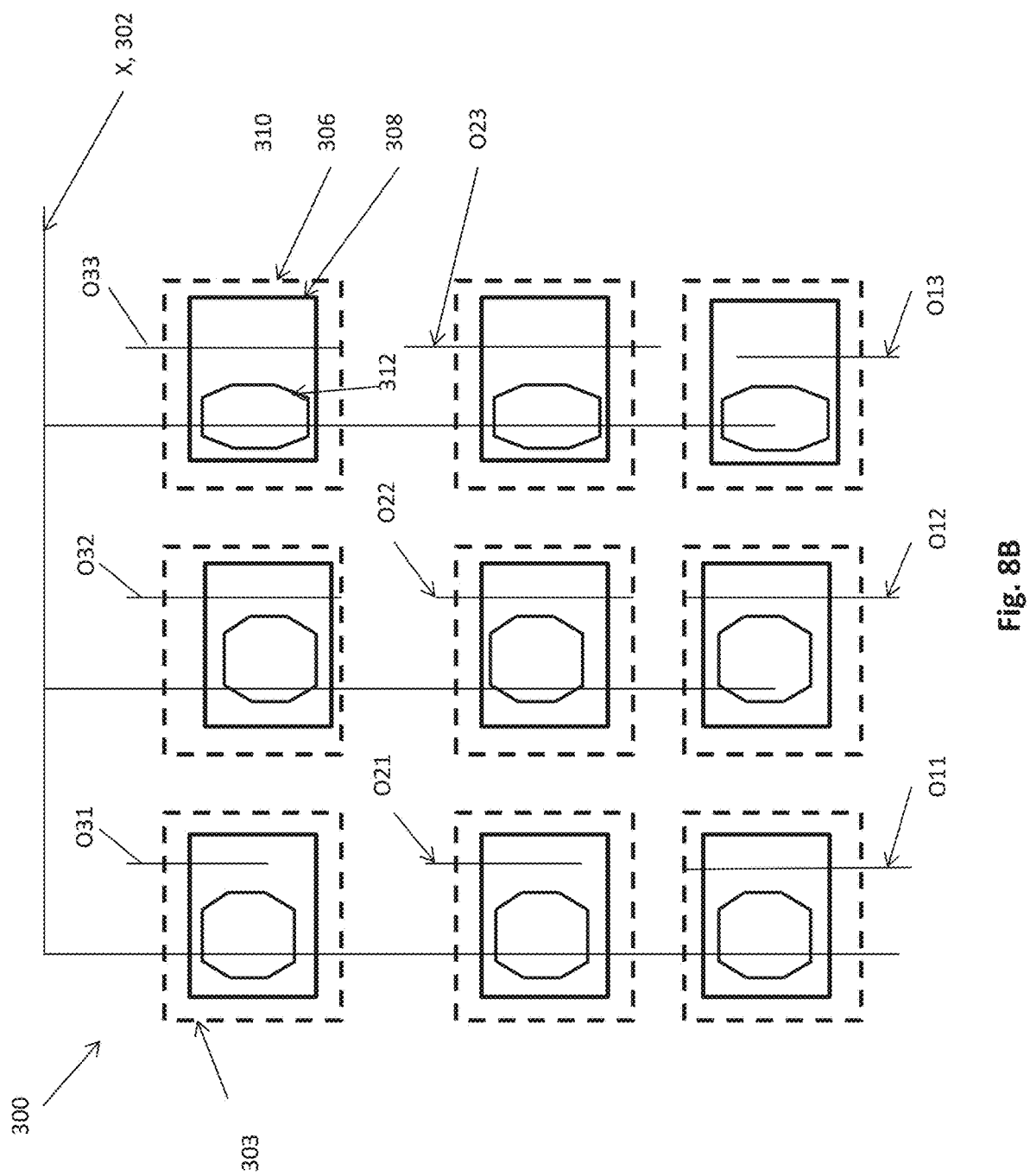
FIG. 8B shows an exemplary embodiment of a 2D array of pMUTs with connections shown to bias voltage and/or actively driven terminals.

The conductor of each piezoelectric element is connected to the electrode and is named Oxy, where x ranges from 1 to 3 and y ranges from 1 to 3, in FIG. 8B. The first conductor of each piezoelectric element is connected to the first electrode and is named O11. Further, all elements for an electronically configurable imager, have their O leads connected to a corresponding electronics located on another wafer. The second electrode of each element called X, are all connected to other X electrodes for the other elements by conductor 302. The conductor O is a signal conductor, while the X is a ground or bias line. In this embodiment shown in FIG. 8B, the O electrodes are connected to an ASIC in close proximity to the substrate on which pMUTs are disposed on. In an exemplary case where there is an array of 32 by 32 pMUTs, there are 1024 piezo elements. There can be 1024 "O" lead connections to the ASIC, typically located below the pMUT die. Each of these 1024 O lines are connected to a transmit driver during transmit operation and to the input of a LNA during receive operations, where the transmit driver goes into a high impedance state in the receive mode.

Figure 9A:
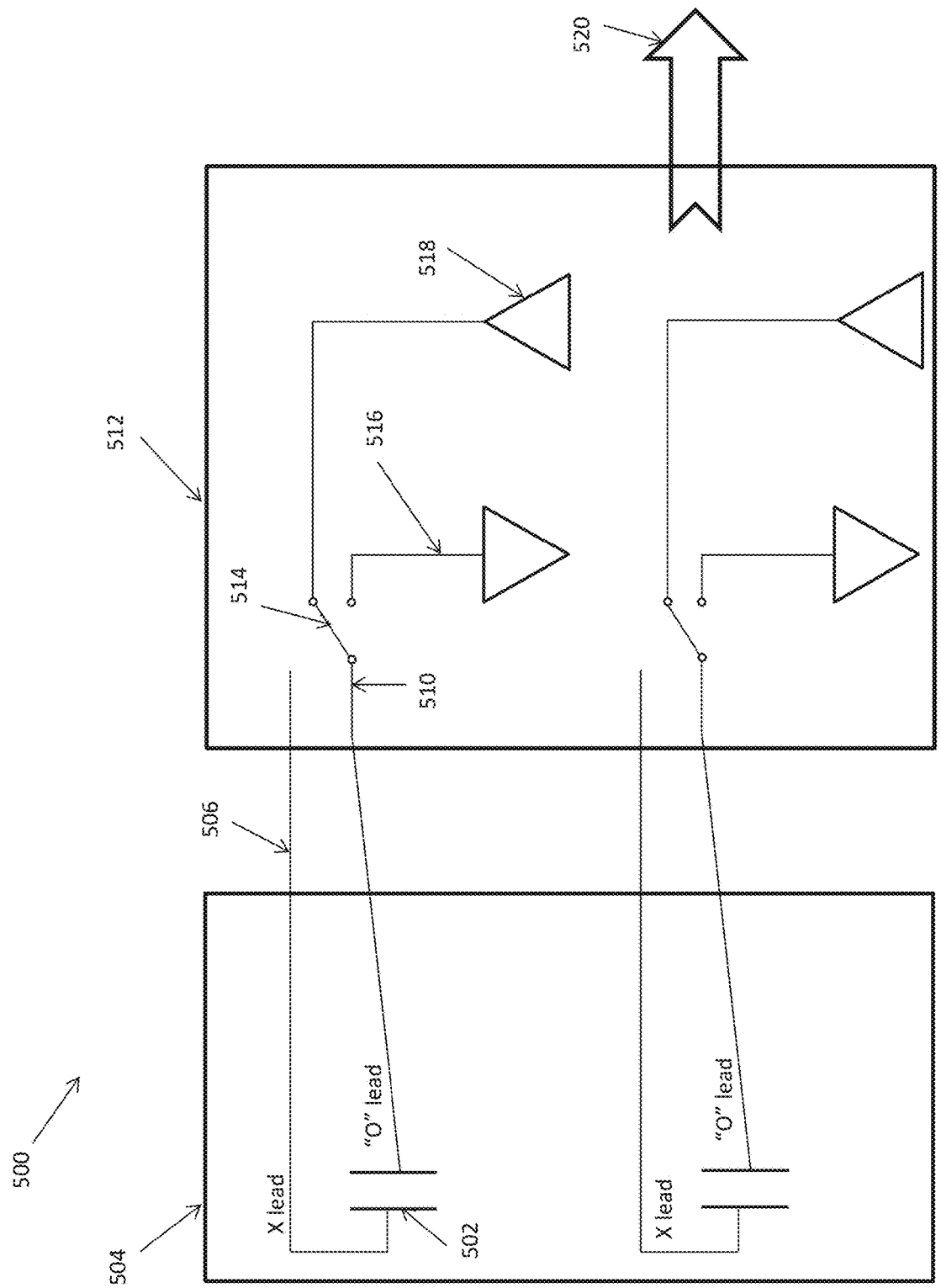
FIG. 9A shows an exemplary schematic diagram of interconnection of 2 pMUT elements to an ASIC containing transmit and receive drivers and other functions.

FIG. 9A is a schematic representation of interconnection of 2 transducer elements to an ASIC 500. In certain embodiments, the 2 transducer elements 502 are on one substrate 504, to an ASIC containing transmit and receive and other functions on another substrate 512. Input of a LNA 516 is connected by switch 514 to lead 510 which connects it to the signal conductor of the transducer, the O lead. In some embodiments, bias conductor 506 are connected into the ASIC and later come out of the ASIC for connection to ground or other biasing voltages. These are the X leads of the transducers and may be connected together with other X leads in the transducer and the ASIC. A transmit driver 518 may be controlled by communication external to ASIC on substrate 512, as indicated by 520. It may also be connected to switch 514, which shows switch connection when in transmit mode. The output of the LNA and the input of the transmit driver as shown in FIG. 9A may require 2 different leads. It is possible to use one lead, by using a multiplexer switch similar to 514. In some embodiments, connection to LNA output can be provided to outside electronics in receive mode, and input to transmit driver can be provided in transmit mode.

Figure 9B:
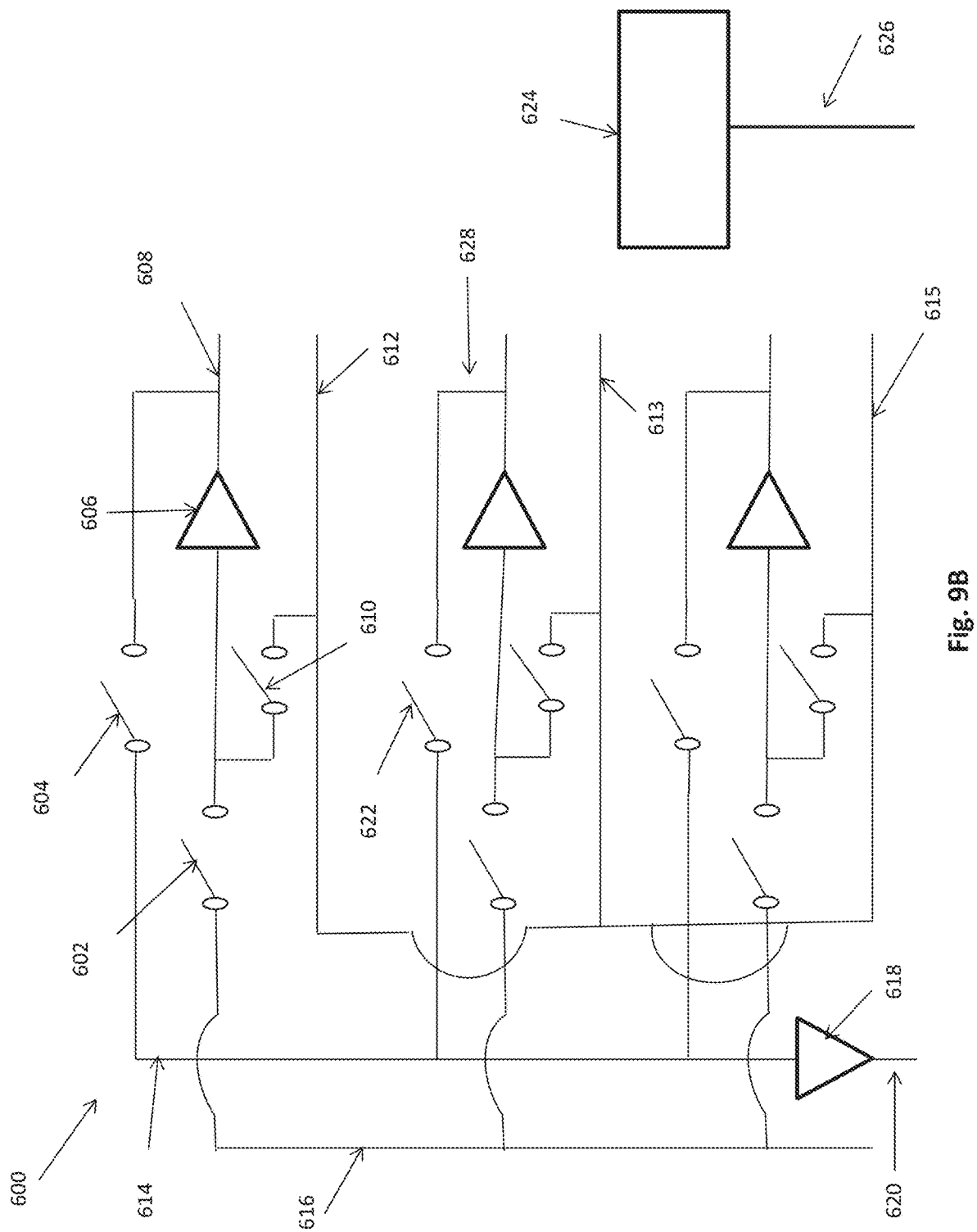
FIG. 9B shows an exemplary schematic diagram of the ASIC of FIG. 9A in which one column of electronics interfaces directly to one column of pMUTs, to constitute a composite larger transducer element.

FIG. 9B shows a schematic representation of some of the functionality in the ASIC for one column of electronics. The one column of electronics may interface directly to one column of pMUTs, to constitute a composite larger line element. It is understood that the ASIC may contain circuitry for other columns or rows and include other supporting circuitry not shown. It is also understood that the actual functionality desired can be achieved with a different circuit topology that would be considered obvious to those of ordinary skill in the art. The representation shown is simply to illustrate the idea itself.

FIG. 9B shows an exemplary schematic of one column of an ASIC 600. In certain embodiments, a conductor 608 is connected to a corresponding signal conductor for an element in the pMUT array of FIGS. 8A-8B, O31. Similarly, O21 of FIGS. 8A-8B is connected to 628 of FIG. 9B. A transmit driver 606 can be connected to the conductor 608 in FIG. 9B. This driver 606 may have a switch 602 connected to its input and connects to lead 616 (the signal conductor for the line element) that connects to the input of other transmit drivers in that column through switches on that column. The switches can be controlled by 624, which via communication with an external controller, may determine which switch(es) to be turned on. Signal conductor 616 may also connect to electronics implementing transmit beamformers. The O conductor 608 can also connect to a switch 604; the other side of the switch 604 may connect to similar switches in that column (for example, 622). The line 614 may also be connected to the input of a low noise amplifier (LNA) 618. Only one LNA may be required for each line element (or column). The LNA can be activated in receive mode by the control unit 624, which also turns on switches (e.g., 604), while turning off other switches (e.g., 602). This may connect the signal electrode of the pMUTs (through connection 608) to the LNA, which may amplify and convert the received signal to a voltage output 620 with low additive noise. Note, in receive mode, the controller may also make the transmit drivers go to disabled mode, where their output impedance becomes very high, so as not to interfere with the receive signal. In transmit mode, when a piezo element is not supposed to transmit, switch 610 can be turned on, with switches 602 and 604 off, to ensure a net zero volt drive across the pMUT signal and bias electrode for elements that are not supposed to transmit signals while in transmit mode. The X lines are also connected to the ASIC. Note, in FIGS. 8A-8B only 1 biasing electrode X is shown. But multiple biasing electrodes can exist.

For simplicity, FIG. 9B only shows the connection to only one of the 2 biasing conductors (X in FIG. 8).

In some embodiments, conductor 612 in FIG. 9B can be connected to X, 302 in FIG. 8. In some embodiments, conductor 613 in FIG. 9B can also be connected to X, 302, but at locations closer to 613, and so on. Note, these additional interconnections 613 and 615 are not essential, while at least one connection (either 612 or 613 or 615) is needed.

FIG. 9B shows that the receive output 620 and transmit input 616 may require 2 leads. But using a multiplexer, one lead can also be used for this purpose.

A line imager herein may include a multiplicity of piezo element columns, each column is connected by at least a signal and bias leads to a controller. Pulses of an appropriate frequency drive a line. The other lines are driven with delayed versions of this pulse. The amount of delay for a certain line is such that it allows the resultant beam transmitted to be steered at an angle or be focused at a certain depth, with operations known as beamforming.

The line imagers of FIGS. 8A and 8B are electronically configurable. Using an example of an array of piezo elements that are arranged with 24 elements in one direction and 64 elements in an orthogonal direction (azimuth direction for this example), a 64 line imager can be built, with each line consisting of up to 24 elements. However, the size can be electronically adjusted from 0 to 24 elements for any line and any number of lines in azimuth up to 64 can be activated.

Figure 10B:
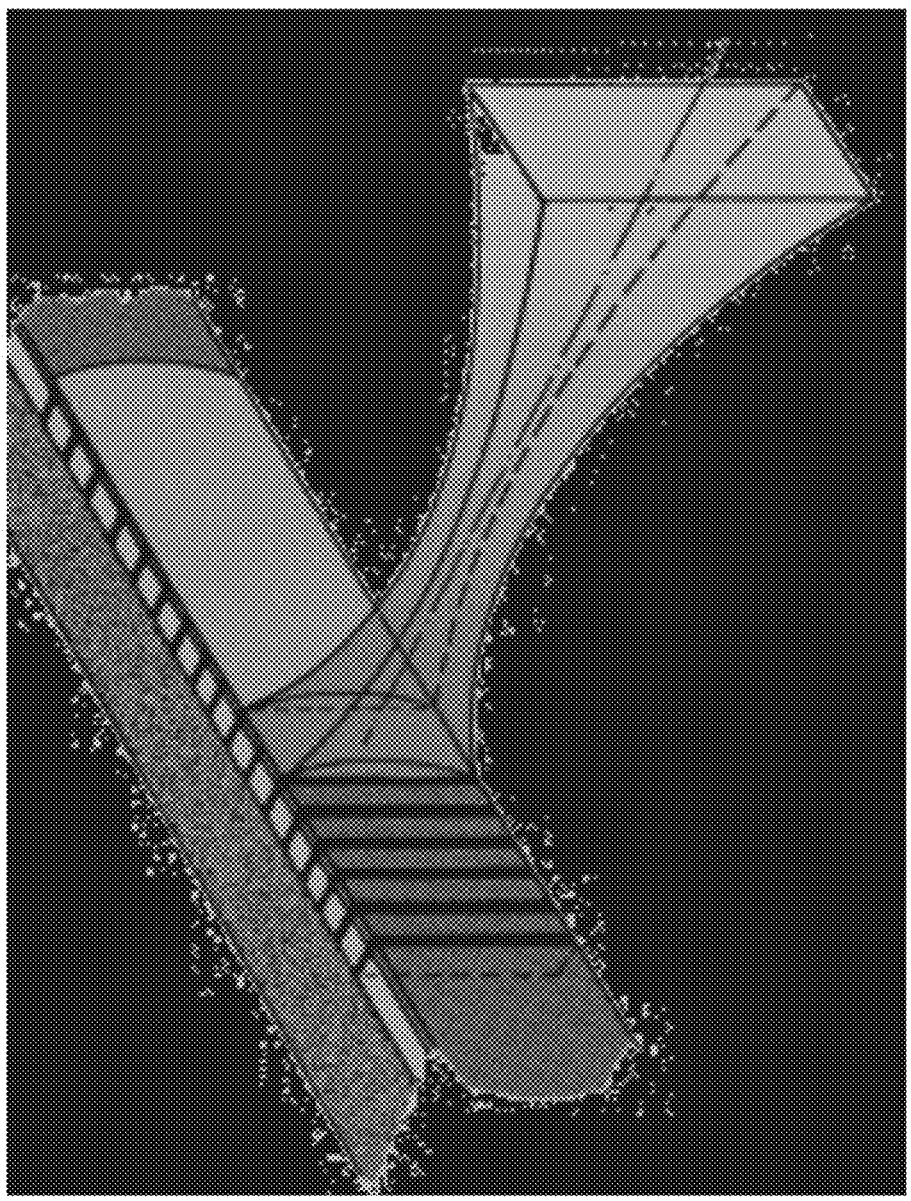

It is desirable in a 2D or 3D imager to image a thin slice of the elevation plane as shown in FIGS. 10A and 10B. In this particular embodiment, elevation direction is in the ya axis on the left panel. An elevation plane 1201 is within the ya-za plane. In the same embodiment, the azimuth plane 1202, also the scanning plane herein, is orthogonal to the elevation plane. Referring to FIG. 10B, a mechanical lens focuses beams in the elevation plane, keeping beams from straying away to form a much thicker slice in the elevation plane and hitting other objects in the thicker elevation slice with the unwanted reflections becoming part of the received signal, adding to signal cluttering and degrading the image quality.

If the beam spreads well beyond the intended slice thickness, it could potentially hit targets outside the desired range and reflections from those will create clutter in the reconstructed image. A mechanical lens formed on the transducer surface can focus beams in the elevation plane to a fixed elevation slice thickness as seen in FIG. 10B, where thickness is minimum at elevation focus point as seen in FIG. 10B and also noted on FIG. 10A as elevation plane focus point. Electronic focus for 2D imaging will allow for improved focus in the elevation plane by virtue of dynamic receive focus as a function of time. Here the focal length in elevation is varied as the beam travels down toward the target and results in a superior image. For 3D imaging, a fixed mechanical lens does not work, since that specific elevation slice cannot be steered or sweep over the desired volume. Therefore, an electronically controlled elevation focus is desirable.

In some embodiments, this is achieved by dividing the transducer into a number of different strips. Referring to FIG. 11, in a particular embodiment, the transducer is organized in N columns, where each column has up to M rows of transceivers' elements. The rows of elements can be divided into strip A which includes a first number of rows, where the strip A has up to N columns, strip B that includes a second number of rows that are in the central section of rows with each row of up to N columns, and strip C that includes a lower section of rows of up to N columns. The strips A, B, and C can be non-overlapping with adjacent strip(s). Alternatively, the strips may overlap for a number of rows and columns with its adjacent strip. In some embodiments, the strips together cover all the N columns and M rows of the transducer element. In some embodiments, when electrically programmed, the strips all together may only cover a part of the M by N array of the transducers.

Figure 12:
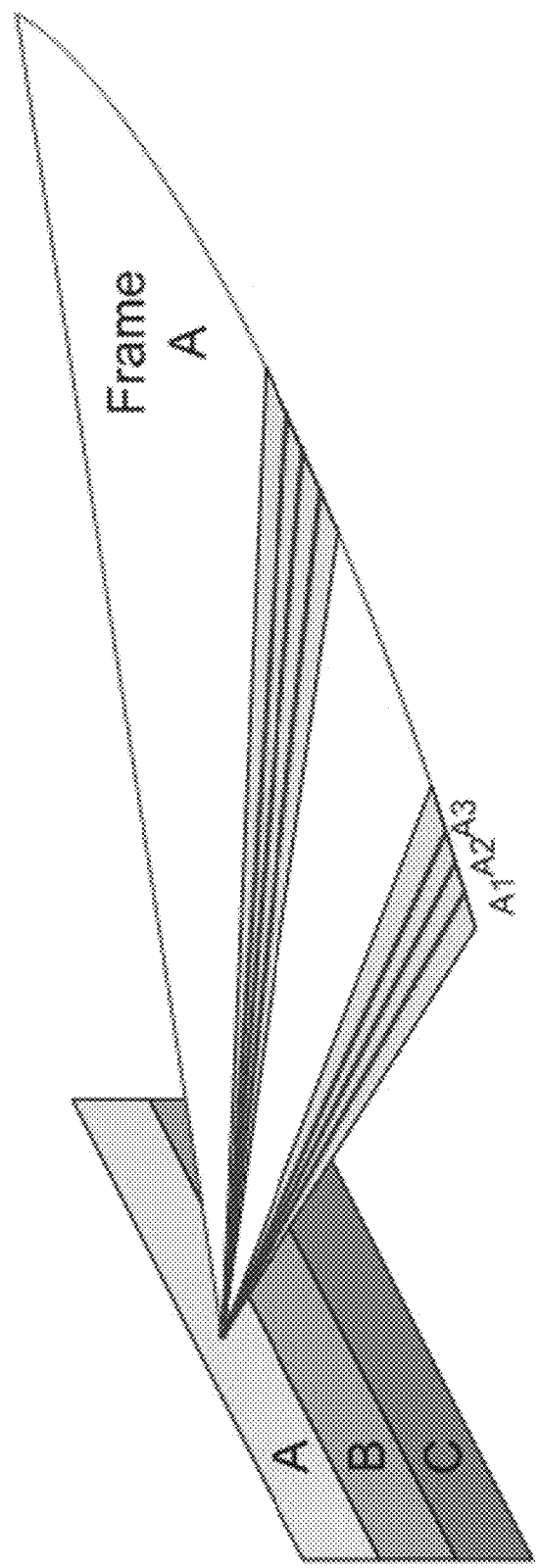
FIG. 12 shows an exemplary schematic diagram of a number of scan lines that make up an ultrasonic image frame.

In some embodiments, the top section A is organized such that all elements in that section are driven by transmit driver(s) intended for the column that the element(s) are in. In this embodiment, in a transmit operation, N transmit driver with unique delays driving N composite columns (each composite column may include elements from rows from strip(s) A or B or C) are used to focus an ultrasound beam in the azimuth plane 1202. During receive operation, reflected signal that impinges in section A is beamformed to create scan line A1, A2, A3, etc. as shown in FIG. 12. Referring to FIG. 12, three strips of PMUTs are labeled as A, B and C. These strips include rows of PMUTs that, where elements on a column are driven by a common transmit driver, with N drivers for N columns (i.e., a different driver for each of the N columns). Scan lines A1, A2, etc. can be formed by transmission and reception using strip A. Scan lines B1, B2, etc. are formed from section B and scan lines C1, C2, etc. are formed from section C. Now using scan data from the 3 sections, another focus this time in the elevation direction is performed using unique delays to data from section A, B and C in a similar technique that was used to focus beams in the azimuth plane earlier using delays along column drivers. This process may be thought as a dual stage beamformer, where first stage consists of developing scan lines from A, B, C and a second stage that used that data to develop focus in the elevation plane. The focus in elevation is achieved in the receiver by digitally applying delays. This technique not only allows a focus in the elevation plane, but also allows focus to be dynamic. In this case, the focal length can be adjusted as a function of time, to allow elevation focus to travel with the ultrasonic beam.

Figure 13:
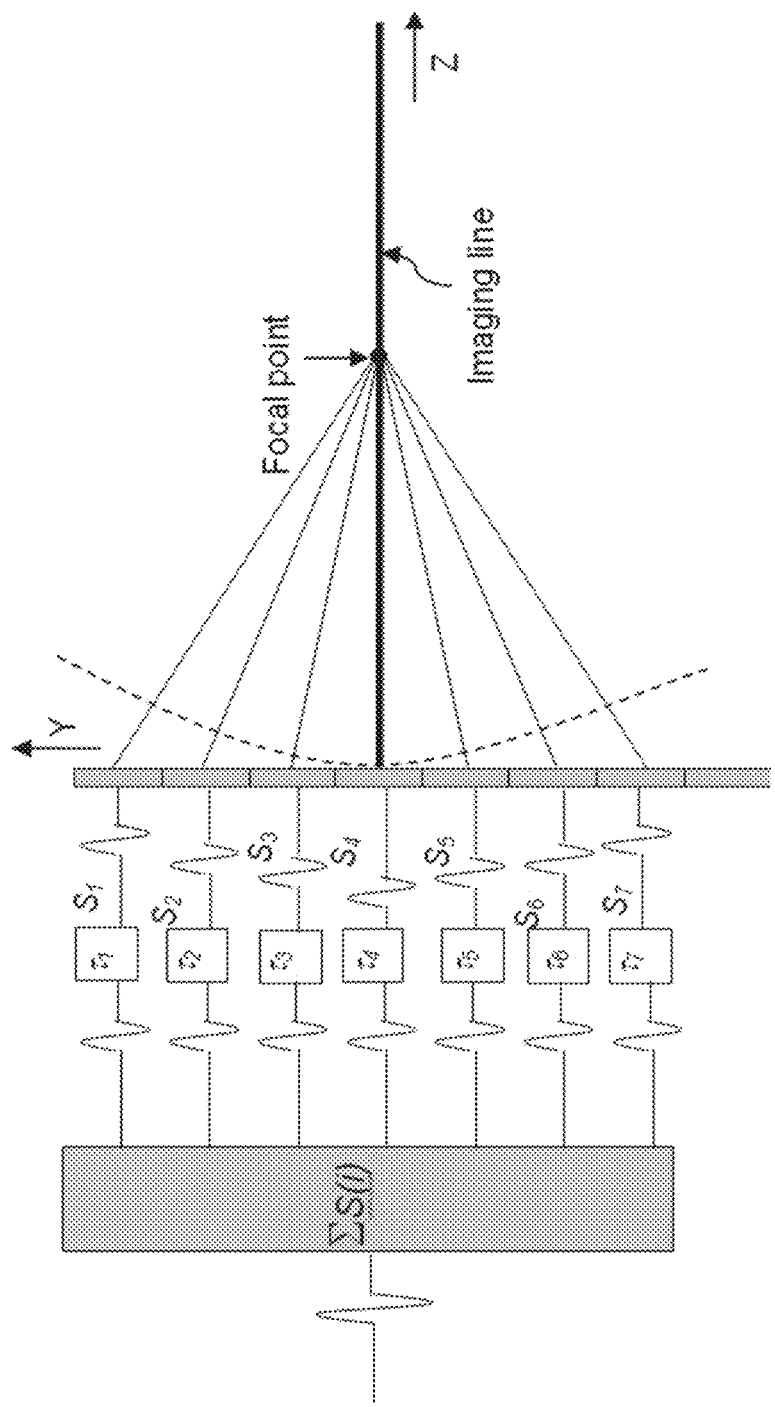
FIG. 13 shows an exemplary schematic diagram of obtaining a scan line of FIG. 12.
Figure 14:
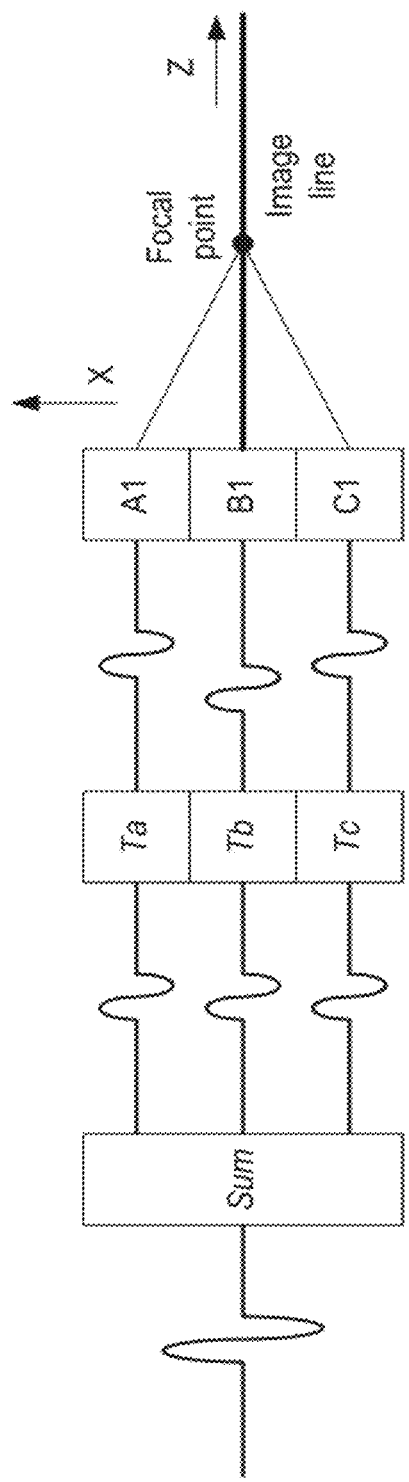
FIG. 14 shows an exemplary schematic diagram of obtaining elevation focus using delays applied to different strips.

Although the process described in FIGS. 13 and 14 may require three transmissions and receptions, the first and second transmission and reception from section A and C can be combined into one operation. In some embodiments, transmissions both from a top portion and a bottom portion of the transducer can be performed simultaneously, where the delays on the top portion and bottom portion of a column are identical. The second transmission is from the central portion with different delays from that used in the first and/or the second transmission.

In some embodiments, the top section, the central section, and/or the bottom section can be divided into one or more subsections, each of which include a number of rows for pulse transmission and signal receiving. In some embodiments, each subsection can be used to form multiple scan lines in a manner similar to what has been disclosed herein.

In some embodiments, the transducer element array can be divided into more than 3 strips, for example, 4, 5, 6, 7, etc. In some embodiments, scan line in each strip can be performed either sequentially or simultaneously. In some embodiments, in simultaneous transmission, scan line from strips symmetrical to the center strip are obtained. In some embodiments, the delays for elements in same column are identical for sections operated on simultaneously.

The focus can also be assisted by further employing a lower amplitude of voltage for a part of the two outer sections of the transducer with respect to remaining parts of the transducer.

Figure 16:
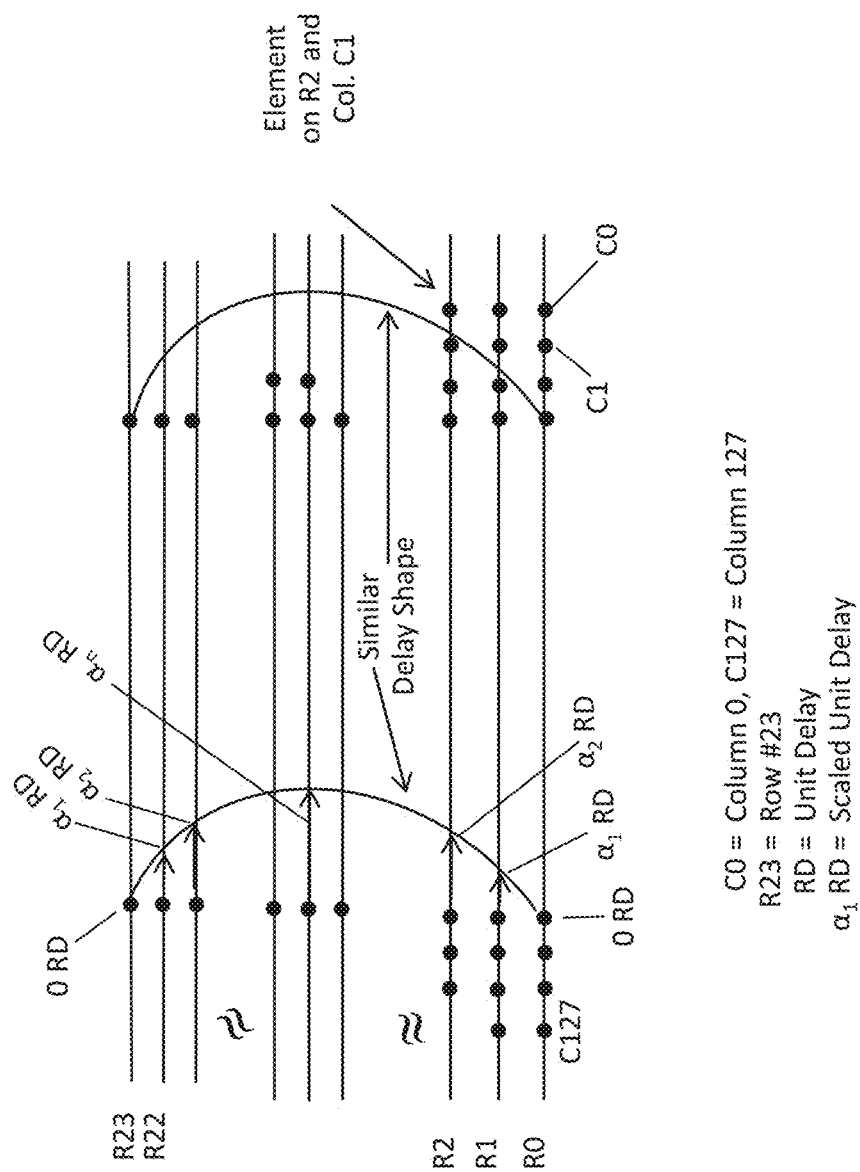
FIG. 16 shows an exemplary schematic diagram of transducer elements and their delays, the delays can be programmed electronically and can be substantially similar for more than one column of the transducer elements.

In some embodiments, a unique programmable delay along the elevation direction is implemented for each element of all columns. All N columns may receive drive signals that are delayed relative to each other. Additional delays can be generated to add further delay along the column elements, where each element along the column can be delayed differently relative to its adjacent neighbor(s) on the same column. A delay profile example is shown in FIG. 16. The delay for all columns elements along the elevation direction can be similar. In one embodiment, the delay is symmetrical, with maximum at the center element for a focus in the elevation plane. The amount of delay difference between the outer and central elements determines the focal length.

In some embodiments, the delay profile is shown in FIG. 16, where relative delay at the edge elements for a column may be 0*RD or 0 ns. For element on row 1 and R22, delay relative to delay at row 0 can be alpha1*RD and so on as shown in FIG. 16, if symmetric delays are desired around a central element. Delay RD is programmable as are alpha1, alpha2, etc. Therefore, a delay profile can be made up along a column, where the delay can be relative to delay at the edge of the columns. The relative delay profile can be identical for other column elements. In other embodiments, the delay profile may not be symmetric around a central element and can be arbitrarily programmed. In some embodiments, the delay is in the range of 25 ns to 1000 ns. In some embodiments, the delay is programmable with different ranges of 10 ns to 5000 ns. In some embodiments, the delay is in the range of 50 ns to 500 ns.

The procedure to obtain a scan line using the systems and methods herein, in some embodiments, is shown in FIG. 13. In some embodiments, the reflected signal is received by the transducer, the signal is converted to voltage and amplified and digitized by an analog to digital converter (ADC). These received signals are also known as RF signals. These RF signals can be delayed by $\tau n$ (e.g., $\tau 1, \tau 2, \tau 3, \tau 4$ . . . ) and summed to form a scan line, e.g., A1, A2, etc. in FIG. 12. In some embodiments the signals are delayed and weighted with coefficients and then summed to form scan lines.

In some embodiments, focusing a beam in the receive direction utilizes more than one RF signals, e.g., S1, S2, etc. along the azimuth direction (Y), which are digitized output samples known as RF signals. In some embodiments, the RF samples are delayed, for example, with a delay profile along the Y direction and the resulting signal, can be weighted and summed to form a scan line.

As illustrated in FIG. 12, in successive transmission and reception events, scan line A1, A2 and additional scan lines can be obtained using section A. In some embodiments, an image frame may include many scan lines such as 100 or even more to achieve fine scan of the target area being imaged. Similar procedure can be used to obtain scan lines using Section B and Section C. The scan lines from sections A, B, C are developed using a first level beamformer, where a beamformer creates scan lines using an algorithm, where in the embodiment described the algorithm used a signal delay and sum method previously described. A synthetic aperture, second level beamformer is then used to achieve focus in the elevation plane, as shown in FIG. 14. In some embodiments, these transmissions are focused on a single elevation angle (0 degree, 10 degrees, 20 degrees, 30 degrees, etc.) thereby reducing out of plane clutter that is not within the elevation plane and obtaining an improved image.

Referring to FIG. 14, in a particular embodiment, second stage focusing/beamformer uses beam data (i.e., scan line data) from: A1, B1, and C1; A2, B2, and C2; A3, B3, and C3; etc., which are delayed, weighted, and summed to form the final beam output to allow elevation plane focusing. In this embodiment, X is the elevation axis.

Unlike mechanical lenses, as disclosed herein with synthetic lenses, the focal distance can be electronically programmed into the beamformer. In some embodiments, the process may require a number of transmissions and receptions (e.g., 1 transmission and reception from N lines to form scan line A1) to form a scan line from any sections of the transducer, e.g., (sections A, B, and C). To form a frame, R scan lines are required to scan full area to be imaged. Further in this case, 3 separate frames A, B, C are needed. In some embodiments, it is desirable to have a high frame rate in an image. A frame may include many scan lines. However, if the number of transmissions and receptions can be reduced while the same number of scan lines can be developed, then the frame rate will be increased. In some embodiments, increased frame rate can be achieved by combining the transmission and reception from two sections (e.g., A and C). Since these regions are symmetrical with respect to a central region, the delays needed for example as shown in FIG. 13 can be identical for regions A and C. By combining these two regions into one combined region to transmit and receive signal from, the frame rate can be increased by 150%. The central portion B may require different delays from the delays used in the first transmission for regions A and C. In some embodiments, scan lines A1, B1, C1 and the like are formed along the azimuth plane. A second beamforming operation can use data from the first level beamformer and using similar techniques as shown in FIGS. 13 and 14, a focus can be achieved in the elevation plane. In some embodiments, 2D scans can start from one side of a strip, e.g., column N, and completes at the other end, e.g., column 1. Thus, frame A which can be obtained by scanning for beam A1, A2, AN . . . in order. By following this sequence for frame B, which is a sequential frame in time to frame A the target may have moved. To minimize impact of motion artifacts, beamforming can be done by interleaving scan lines for different frames, such as A1, B1, C1, A2, B2, C2 and so on. When A and C are combined such that transmit and receive can be done together, the combined A, C region can be named as D and scan lines as D1, D2, etc. A non-limiting exemplary scan sequence can be D1, B1, D2, B2, etc. This may help minimize sensitivity to movements in the target being imaged.

In some embodiments, the number of rows used to form A, B, C is programmable. The number of rows can be adjusted depending on what anatomies are being imaged and can be set using presets, for example, based on anatomies or patient information, in the user interface.

In some embodiments, an electronic synthetic lens offers dynamic focusing and dynamic aperture. For example, in near field, the weights for A and C can be minimal and gradually increase with depth, thus resulting in change in aperture.

In some embodiments, sections (e.g., A and C) are apodized during transmission and reception. Apodization can be achieved by pulse width modulation (PWM) of the Transmit (Tx) drive waveform. A unapodized pulse drive has a nominal pulse width. When pulse width is changed, e.g., reduced, the pressure output from the pMUT can reduced. In some embodiments, apodization is a tapering of weights for elements as they go from the center of the transducer to the edges. This can reduce side lobes and create higher quality images. By applying apodization to the procedure described, signals leaking outside of the elevation plane can be reduced.

Figure 20:
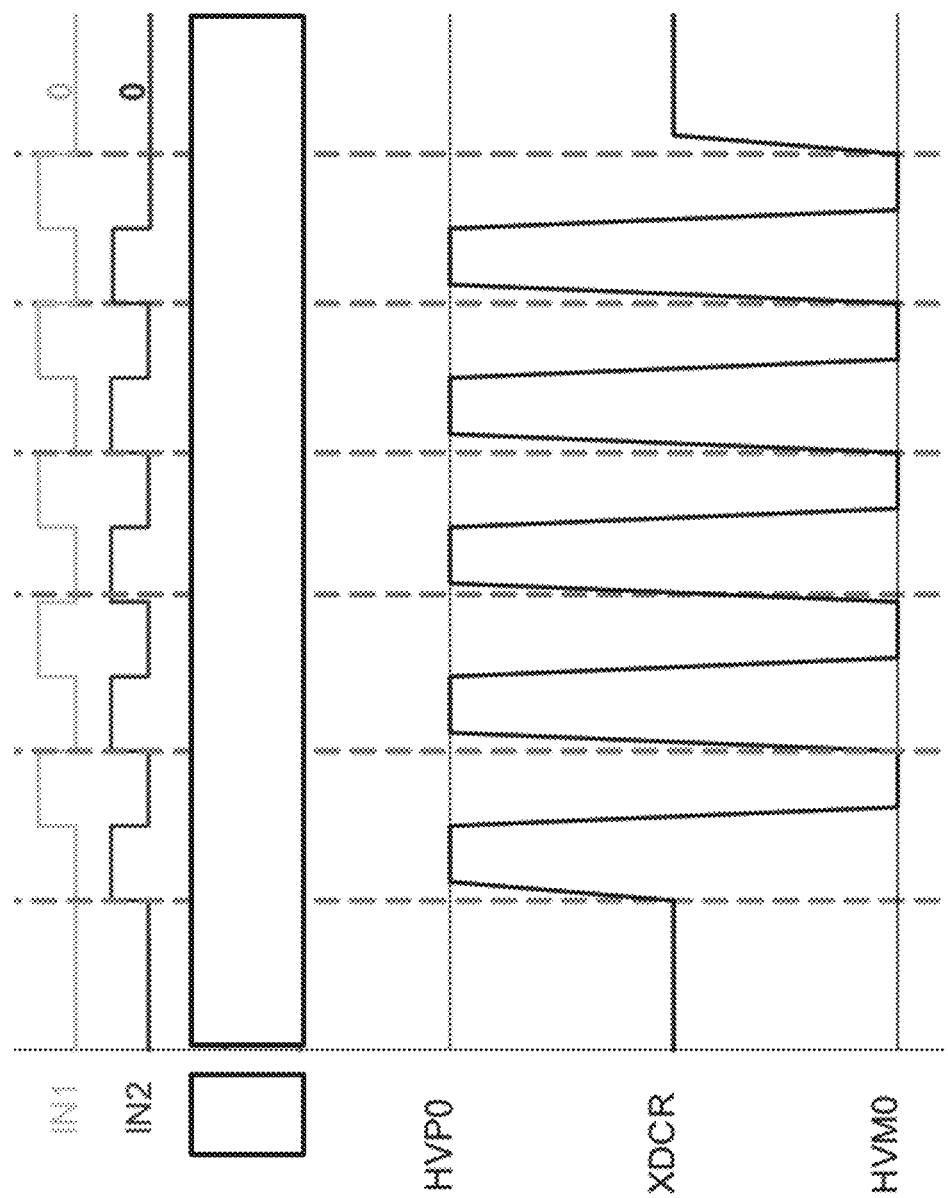
FIG. 20 shows an exemplary schematic diagram of a pulsar with two digital inputs that generates an output as transmit drive pulse(s).

In some embodiments, the apodization can be achieved by using a multi-level transmit drive, for example, 3 or 5 or 7 levels. By choosing different levels of this drive signal, apodization can be created by applying amplitude varying transmit drive signals that are lower in amplitude for element closer to the edge than the center of the transducer. In this example, all elements on outer rows compared to central rows can have lower drive voltages, by digital decoding and selecting, certain drive levels may be available to form the multi-level outputs. A three level decoding example is shown in FIG. 20.

In some embodiments, apodization is implemented by employing piezoelectric elements of smaller size at edges compared to those at the center of the transducer aperture.

In an embodiment, the circuit employs programmable delays along the elevation direction for all columns. All N columns may receive drive signals that are delayed with respect to each other. Additional delays are generated to add further delays along the column elements, where each element along a column can be delayed differently with respect to its adjacent neighbor on the same column. A delay profile example is shown in FIG. 16. Therefore, the effective delay for an array element $ele_{i,j}$ is the summation of the group column delay, $\tau_j$, and then the individual row delay, $$\tau_{i,j} = \tau_j + \tau_i \quad (1)$$

Where in one embodiment:

$$\tau_j = \sqrt{(x-x_j)^2 + z^2}/c \quad (2)$$

$$\tau_i = \sqrt{(y-y_i)^2 + z^2}/c \quad (3)$$

In the above equations, the focal point on transmit is at position (x,y,z) and the delays are calculated independently for the element at position $x_j, y_i$. The variable c is the assumed speed of sound in the propagating medium. Note that in the case of perfect, non-separable focusing, the delay for transducer element, $ele_{i,j}$, is computed as:

$$\tau_{i,j} = \sqrt{(x-x_j)^2 + (y-y_i)^2 + z^2}/c \quad (4)$$

The separability assumption of the delays in azimuth and elevation is not perfect and the largest errors in the delay profile will occur on the outer elements of the focusing aperture. However, for small steering angles, and large f/#'s this separability assumption provides satisfactory results and ease of electronic implementation.

The delays for all column elements along the elevation are similar. The delay profile can be symmetrical, with a maximum delay at the center for a focus in the elevation plane. The amount of delay determines the focal length. Shallow focus depth requires a relatively longer delay, for example on the order of hundreds of nanoseconds, while deeper focus depth requires shorter delays, for example on the order of a few nanoseconds. Another technique employs a programmable delay along the elevation direction for all columns. All N columns may receive drive signals that are delayed with respect to each other. Additional delays are generated to add further delay along the column elements, where an element along the column can be delayed differently with respect to its adjacent neighbor on the same column. Asymmetrical delays with respect to the center element on a column thus can also be achieved.

In another embodiment, programmable delays are employed along the elevation direction, where the elevation delays are a summation of a coarse, linear delay and a fine, arbitrary delay. Again, all N columns receive drive signals that are delayed with respect to each other. Elevation delays are generated to add further delay along the column elements, where each element along the column is delayed by a coarse and fine delay, where the coarse delay may be linear between adjacent elements and the fine delay may be linear or non-linear between adjacent elements. The linear delay and fine delay along the column elements can be different from column to column. Therefore, the effective delay for an array element $ele_{i,j}$ will be the summation of the group column delay, $\tau_j$, the linear coarse row delay, $\tau_{i,coarse}$, and the fine row delay, $\tau_{i,fine}$.

$$\tau_{i,j} = \tau_j + \tau_{i,coarse} + \tau_{i,fine} \quad (5)$$

Where in one preferred embodiment:

$$\tau_j = \left(\sqrt{(x-x_j)^2 + (y-y_{min})^2 + z^2} - \sqrt{x^2+y^2+z^2}\right)/c \quad (6)$$

$$\tau_{i,j,coarse} = \Delta\tau y_i$$

-continued $$\tau_{i,j,fine} = \left(\sqrt{(x-x_j)^2 + (y-y_i)^2 + z^2}\right)/c - \tau_j - \tau_{i,j,coarse} \quad (7)$$

In the above equations, the focal point on transmit is at position (x,y,z) and the delays are calculated independently for the element at position $x_j, y_i$. The variable c is the assumed speed of sound in the propagating medium. In equation (6) the $y_{min}$ parameter is calculated by projecting the focal point, (x,y,z) onto the 2D transducer plane and calculating the transducer row position with minimum distance to the projected focal point. The slope of the coarse delay, $\Delta\tau$, can be calculated such that the fine delay can be used to give a good approximation of the perfect 2D delays.

It should be clear to one skilled in the art that the above methodology for calculating delays gives a much better approximation to the 2D focal delays of equation (4) compared to the X-Y separable delays previously mentioned. The improved delay calculation comes at the expense of requiring a coarse delay clock, fine delay clock, and some more register bits for implementing the different delays on a column by column basis. However, this method is easier to implement in an integrated circuit than a fully arbitrary delay in two dimensions with fine clock delays and individual element routing. In another embodiment, a cascaded series of flip flops gate a clock arriving at the column from the Tx beamformer with appropriate delay. This delay is then propagated in the column by a different clock whose frequency is programmable, but synchronized to Tx clock that generated the delay for drivers for the various column drivers. For symmetrical delay around a central element on the column, the flip flop chain generating the delays stop at the central element of the column, where the delay profile is symmetrical around the center as noted in FIG. 17. The delays generated by the flip flops are routed to the proper locations, so a row 0 element has same delay as an element on the last row, and an element on $2^{nd}$ row has similar delay as an element $2^{nd}$ from last on top side and so on. In an embodiment, the delays between adjacent elements in a column are linear. The results in Table 1 and the elevation beamplots in FIG. 23 quantify the effects of using a linear delay profile in elevation compared to a parabolic profile. The results in Table 1 quantify the beamwidths (at −3 dB and −10 dB) of the one way beamplots in FIG. 21. Five different implementations of elevation focusing are investigated for a 2D transducer array: 1) no elevation focusing 2) Perfect 2D focusing (Eq. 4), 3) linear delays, 4) piecewise linear delays and 5) sparse apodization. For the linear delay case, the delays between adjacent elements along a column are fixed with respect to one another, and the elevation delay profile can be symmetric around the center of the array. For the piecewise linear delays, the delay profile is separated into at least 3 segments where the adjacent elements in a given segment have fixed delays relative to one another. This method can allow for a better approximation of the parabolic delay profile by including multiple linear delay segments. Finally, the sparse apodization method reduces the number of active elements compared to the other methods by turning elements on and off in order to make the array behave similarly to a 1.5D array on transmit. One example of this sparse apodization method is shown in FIG. 21. In this approach, the output pressure may be reduced compared to the output pressure full aperture. The results in Table I show the −3 dB and −10 dB beamwidths of the elevation beamplots with 0° steering in azimuth. The results show that the linear delay method is better than using no elevation focusing and is similar to the perfect 2D focusing method. The piecewise linear delay method achieves an even better beamwidth performance than the linear method. The sparse apodization method is better than no elevation focusing in terms of achievable beamwidth but is not as good as the linear methods. The reason for the sparse apodization method underperforming is most likely due to the fact that the pitch along the "rows" of the sparse array is reduced compared to the other methods. The elevation beamplot results in FIG. 21 show that the linear and piecewise linear delay beamplots are similar to the 2D focused beamplot down to −15 dB. The sparse apodization method has an asymmetric beamplot due to the lateral offsets of the rows and this method also exhibits the largest sidelobes of all methods investigated. The methods also show stability when laterally steering off-axis (right hand plot of FIG. 21). These results suggest that the aforementioned electronic elevation delays methods are suitable alternatives for phased array and linear array imaging in low-cost, battery operated ultrasound systems.

TABLE 1

Elevation focus impact using various delay profiles or no focusing. These results quantify the results of the 0° azimuthal steering beamplots on the left hand side of FIG. 21.

| Focusing Method | −3 dB Beamwidth (mm) | −10 dB Beamwidth (mm) |
|---|---|---|
| No Elevation Focusing | 6.08 | 15.98 |
| Perfect 2D Focusing | 5.35 | 9.23 |
| Linear Delays | 5.38 | 9.25 |
| Piecewise Linear | 5.35 | 9.25 |
| Sparse Apodization | 5.50 | 9.65 |

FIG. 21 shows elevation beamplots of a simulated 24×128 matrix array with 0° lateral steering (left) and 45° lateral steering (right). This figure shows the differences of the investigated methods of providing focusing in the elevation dimension compared to no elevation focusing (blue curve).

Figure 22:
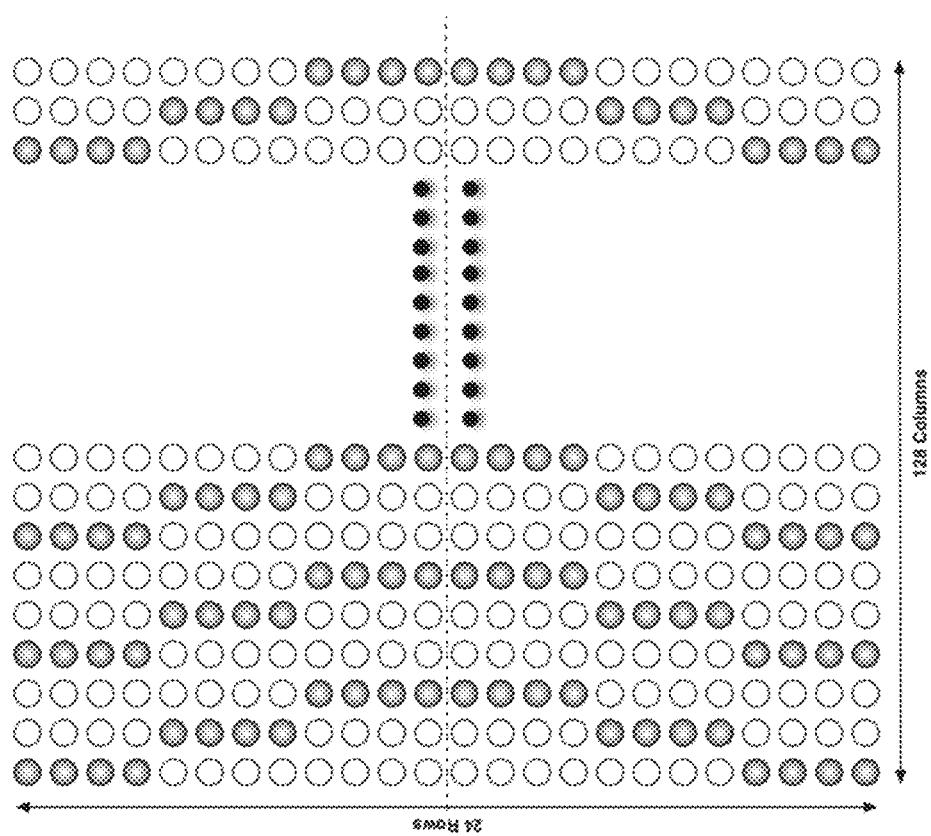
FIG. 22 shows a sparse Tx aperture allowing for transmit elevation focusing with a 24×128 2D array.

FIG. 22 shows a sparse Tx aperture allowing for transmit elevation focusing with a 24×128 2D array. The shaded circles are the active elements per column and elevation symmetry is used (assumes focusing along the elevation plane of symmetry). This transmit scheme would output approximately ⅓ less pressure than when using all 24×128 active elements.

Figure 15A:
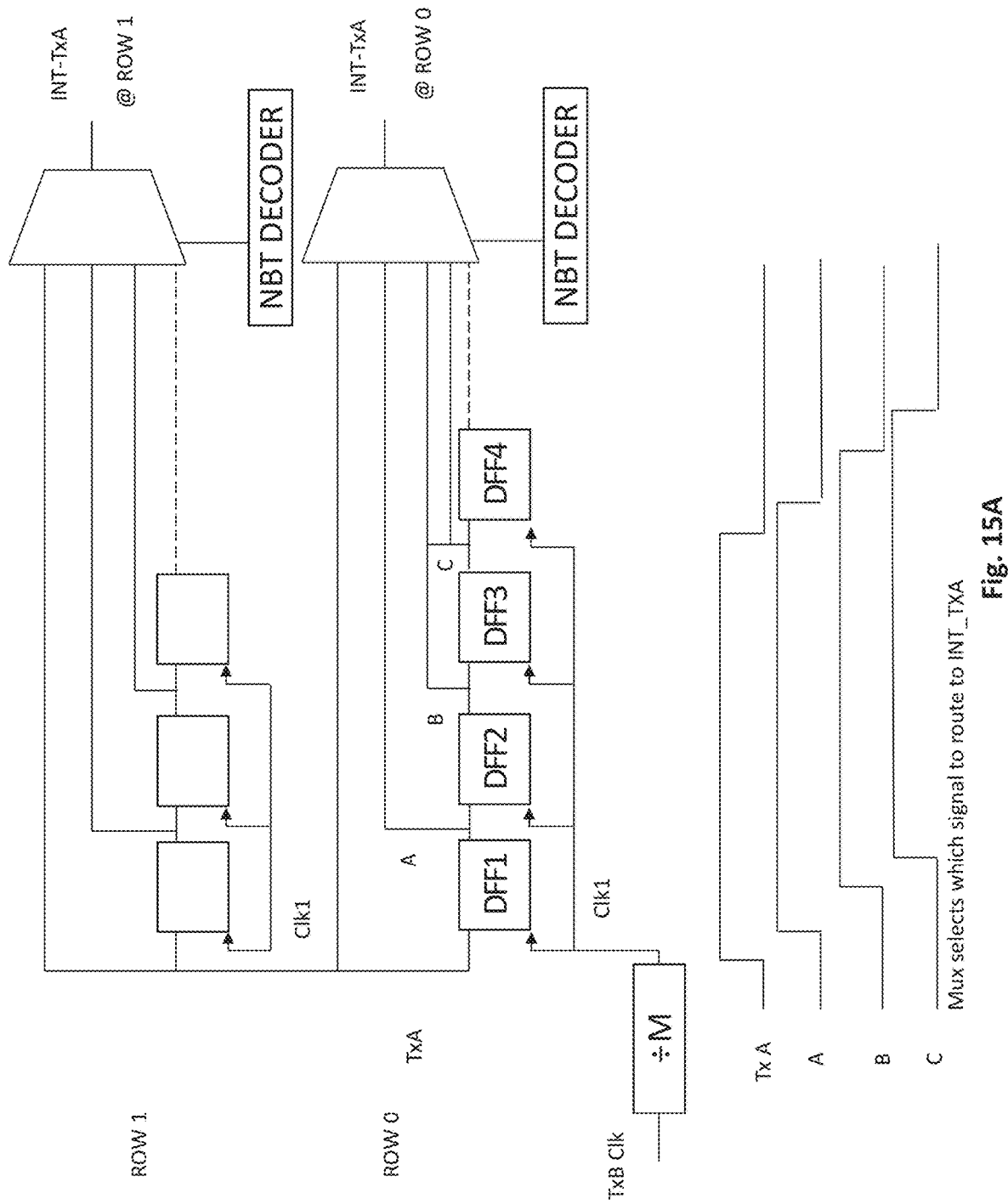
FIG. 15A shows an exemplary schematic diagram of a delay circuit herein with multiple flip flops.
Figure 15B:
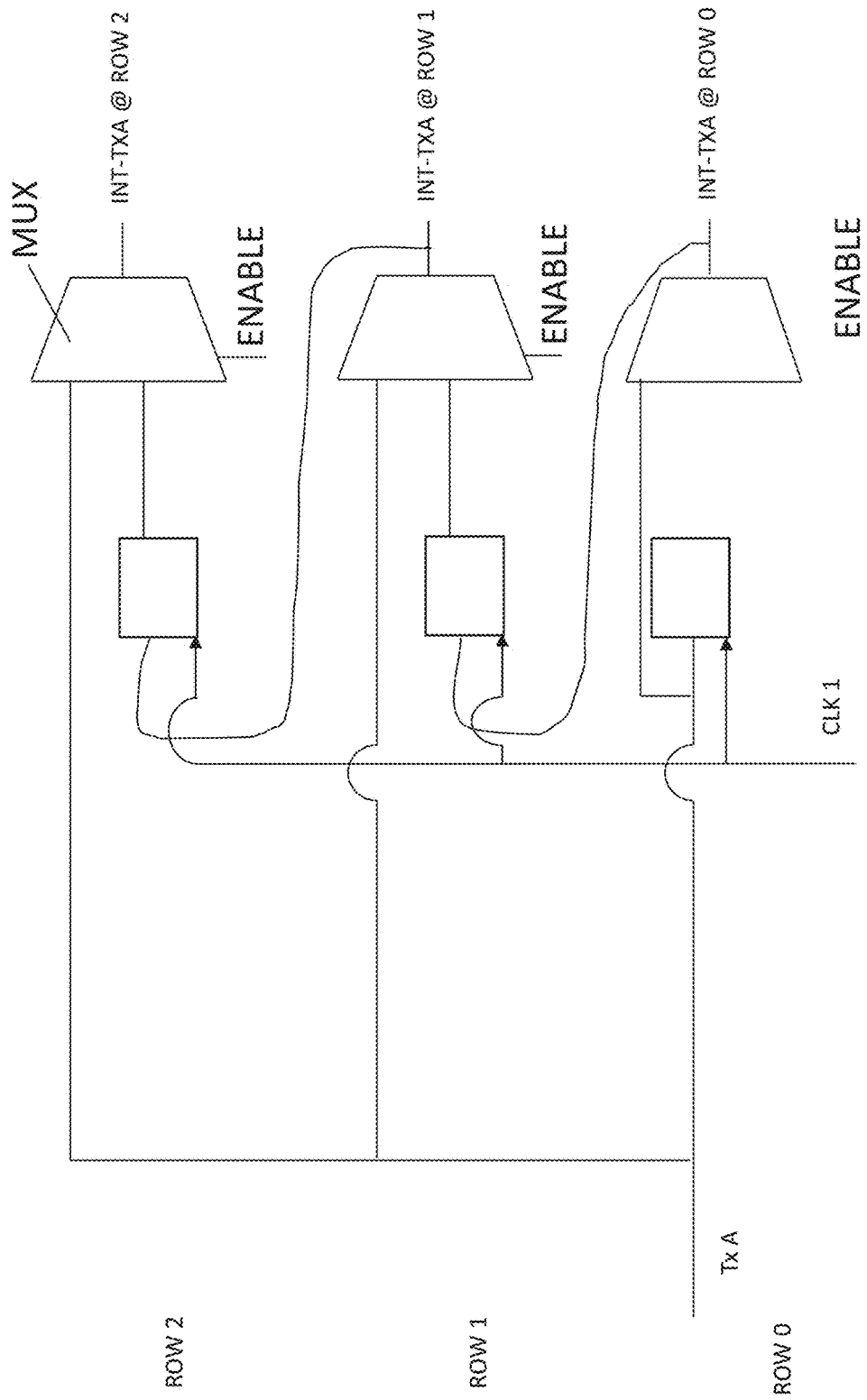
FIG. 15B shows an exemplary schematic diagram of a delay circuit herein.
Figure 19:
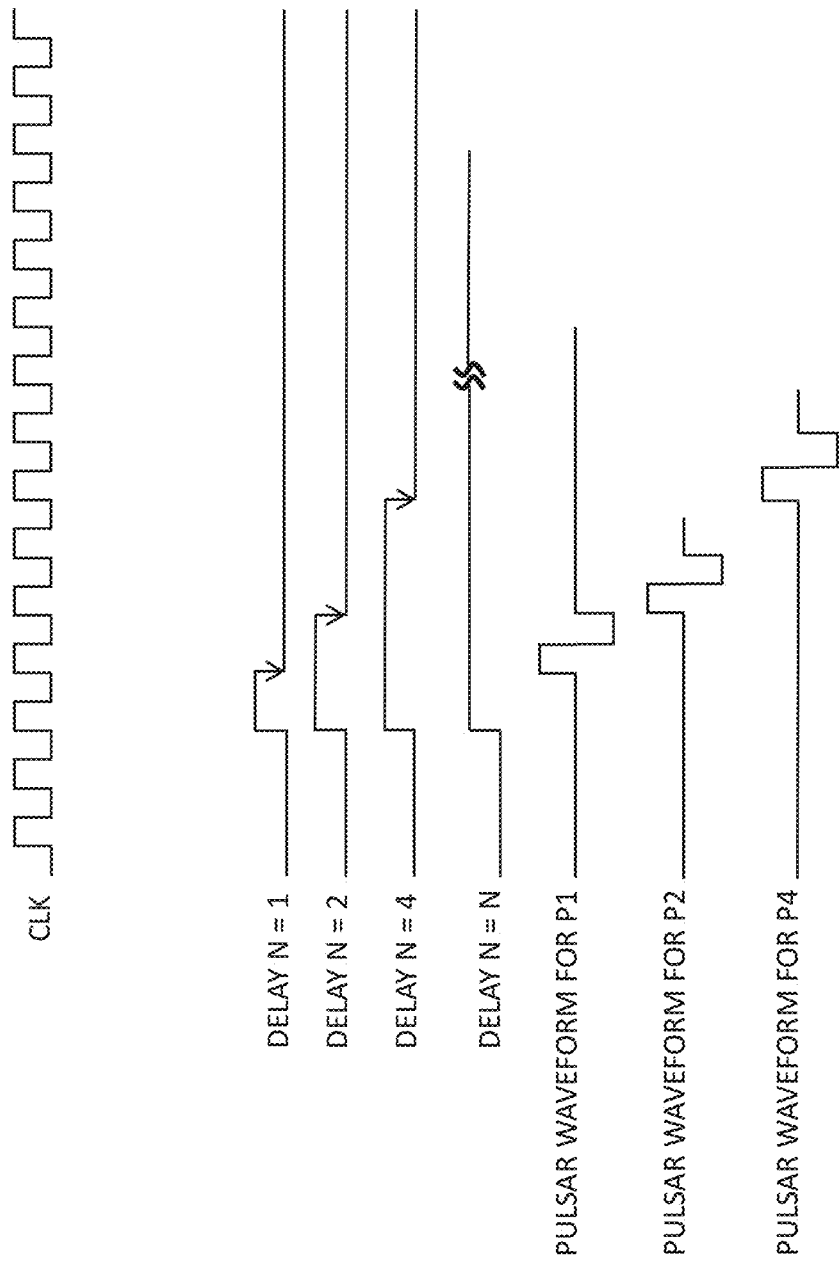
FIG. 19 shows an exemplary schematic diagram of generating different delays using internal counter signals.
Figure 28:
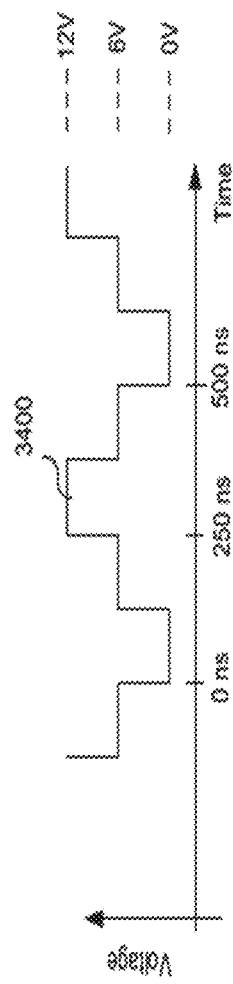
FIG. 28 shows a transmit drive signal waveform according to embodiments of the present disclosure.

In some embodiments, each element on a column has a dedicated transmit driver. In some embodiments, each element driver includes a digital delay circuit driven by a clock, e.g., TxB Clk. The delay circuit in one embodiment comprises multiple flip flops as shown in FIG. 15A. The flip flops (e.g., DFF1, DFF2, DFF3, DFF4, etc.) have a digital input starting from the bottom of the column, e.g., Row 0. TxA is a digital bit generated from a Transmit beamformer. The transmit beamformer in this preferred embodiment consists of circuitry that provides multiple digital bits per channel. In FIG. 15A, we show 2 bits per channel. TxA is such a bit. TxB is another bit, with circuitry identical to that shown attached to TxA also duplicated for TxB. These 2 bits are encoded to determine the voltage drive levels for the transmit driver as shown in FIG. 28. Here TxA and Txb are digital signals that are decoded to determine output levels of the Tx driver. For example if TxA, TxB are both 0 or, the output level is common or sometimes, a signal ground. If TxA=1,TxB=0, the output is HI. This can be a positive voltage of 5V or 10V or some other value as needed. When TxA=0, TxB=1, the output goes LO or −5V or −10V for example when common is 0V. The TxA and TxB are created in a Tx beamformer using a high speed clock called TxB CLK. This is in a preferred example, a 200 MHz clock. Delayed output signals from the Tx pulsar output can be used to steer or focus ultrasound beams as shown in FIG. 16 Here, a line imager is assumed with all elements on a line sharing same delay. Each line element has 2 bits (TxA,TxB) sent by the Tx beamformer. The bits for the next lines are different and can be delayed depending on need to steer of focus a beam. These delays applied by the Tx beamformer are along the azimuth axis and can steer or focus a beam in the axial direction. Delays are however also needed along the elevation direction to steer or focus a beam in the elevation plane. This requires separated delays for elements on a column. FIG. 15A shows an exemplary embodiment. The TxA, TxB bits arrive from the Tx beamformer at a column. Flip flips DFF1-DFFN, where N is 1 to 16 or 32 or as large as needed, are located on every row. DFF1's input pin 2 connects to TXA or TxB. Pin 1 of flip flops are connected to clock named clk_hi, which is generated by a digital divider with TxB clock as its input. The division is by M, where a digital input bus labeled Div Control, shown here as a 8 bit bus, is used to determine the value of M. Flip flops DFF1-DFFN, created delays of tXA/TxB input signals as shown in FIG. 15A with A,B,C being delayed versions of TxA,TxB. The outputs of these are connected to a MUX which selects one of these inputs as its output, where the selection is done using a DECODER controlled by SEL0, SEL1, and so on., where these consist of F bits. These digital outputs, 2 in this case per element, is then decoded as shown in FIG. 20 and used to drive the pulsar output. This circuit can provide fine delays with respect to incoming delay on TxA,TxB bits for elements on a column. Further, these delays can be unique for the elements on the column. FIG. 15B shows an exemplary embodiment, where coarse delays can be also added to elements on a column. Here another divider, this time divides by N, the input clk TxB, where M is smaller or equal to N and are integers. The output of this divider, clk_lo is connected to the clk input of the DFF shown in FIG. 15B. Here, TxA or the output of the DFF (which is a delayed version of TxA) is connected to a MUX and if a non-delayed version is chosen, that is applied to row 0 element. This is then connected to pin 2 of DFF on row 1. This time if row 1 element wants a delay, the delayed version (pin 3 output of DFF) is selected by MUX on row1. This can be repeated for the next element. Here we have added a delay to all elements on the column except for element on row 0. This linear delay applied to elements up the column will help steer a beam. Circuits on FIGS. 15A and 15B can also be combined to impart a fine delay and a course delay to all elements on a column. For example, this can be done by adding circuitry to INT TXA@Row0 and similar node on other rows, where the fine delay circuitry from FIG. 15A is inserted to add fine delays to these outputs already delayed by a course delay generator. These circuitries provide fine delay. Following the output of DFF a going up to a mux, similar to mux 1, but for the next row. This signal is then delayed by DFF connected to it. The same process is repeated going vertically to other rows. This delays signals linearly going up the elements on a column. On each row, DFF1-N adds fine delay as desired to all elements on a column. A second input of mux 1 and similar mux's for all rows are used to delay signals linearly starting with least delay on the top and largest delay at the bottom (row 0). TxA/B in this will also connect to pin2 of mux 1's clone on last row. This way using the UP control on MUX1 (and its equivalents on other rows) the delay could be increasing from the bottom to the top or vice versa. FIG. 19 shows pulsar waveforms, i.e., output of the transmit driver after delay and decoding for elevation focus is complete where P1 represents the transmit driver output for element 1 with 1 delay unit, P2 is for 2 delay units applied to element 2 and P4 is output of element 4 transmit driver with 4 delays. In this case only coarse delay up the column is shown and no fine delay is shown in this diagram. FIG. 16 shows relative delay for elements on a column. In some embodiments, the amount of delay determines the focal length. In some embodiments, the starting delay for all columns can be different, set by needs to focus along the azimuth axis. The delay along the elevation axis can be arbitrary. For example, delay can linearly increase from the bottom row going to the top row of the transducer. In this case, the beam can be steered in the elevation direction. If the delay is symmetric around the central element, the focus is in the elevation plane. Other various delay profiles are also possible and can allow focus and steering of the elevation slice.

Figure 17:
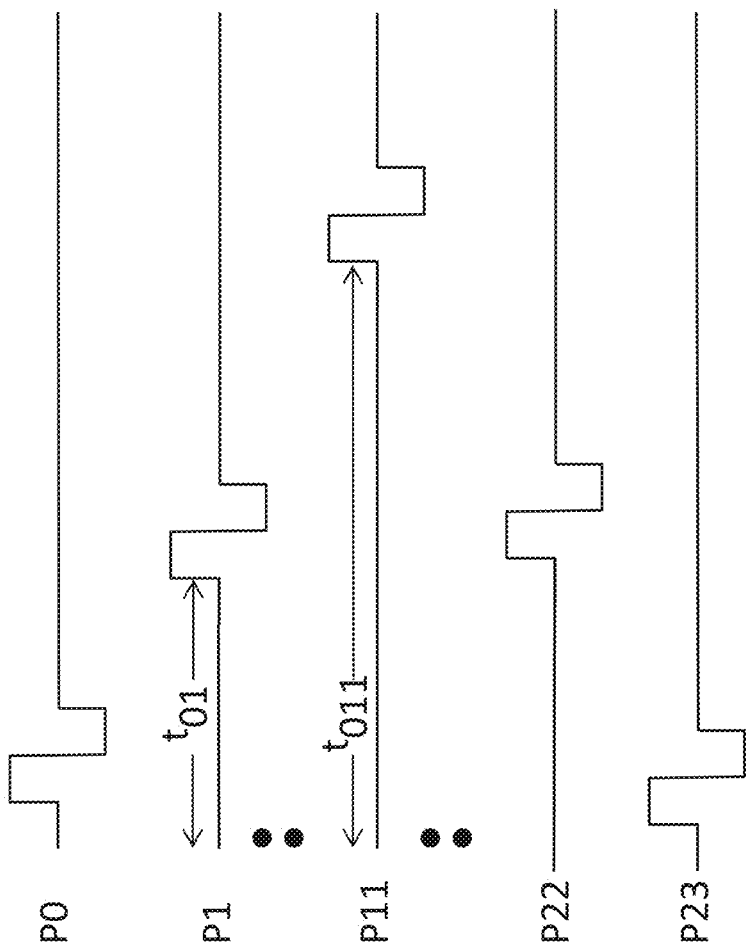
FIG. 17 shows an exemplary schematic diagram of transmit drive pulses with delays for a column of transducer elements with delay symmetry around a central element.

FIG. 17 shows non-limiting exemplary waveforms of transmit drive pulses applied to the piezoelectric elements along a column of the transducer. In this embodiment, the transducer has 24 piezoelectric elements on a column. P0 is the piezoelectric element on a certain column (e.g., column 1, 2, 3, 4, 5, 6, 7, 8, 9, 10, 11, etc.) on row 0, P1 is the piezoelectric element on the same column as P0 but on row 1, P11 is on the same column but on row 11, P22 on row 22 and P23 on row 23. In this embodiment, one pulse at a certain frequency is applied to element P0. The same pulse is applied to element P1, but delayed by t01 with respect to P0. Similarly, the same pulse arrives at P11 with delay t011 which is longer than delay t01. In this embodiment, delays have symmetry around the central element P11. This means pulse timing at P23 and P0 are substantially identical, pulse timing at P1, P22 are substantially identical, and so forth as indicated in FIG. 17. In some embodiments, the pulse (width, magnitude, shape, and/or frequency) herein is the same for all the elements of the same column. In some embodiments, the pulse relative delay and frequency herein is the same for all the elements on 2 rows for a column, for initial delay on element on $1^{st}$ element on a column can be different from similar element on a different column. In some embodiments, the pulse herein has various shapes and waveform may have multiple pulses. Non-limiting exemplary shapes of the pulse include one or more of a rectangular pulse, a Gaussian, and a sinusoidal pulse. In some embodiments, the delays, e.g., t01, t02, t03, . . . , t011 are programmed and controlled electronically for all elements on all selected columns.

Figure 18:
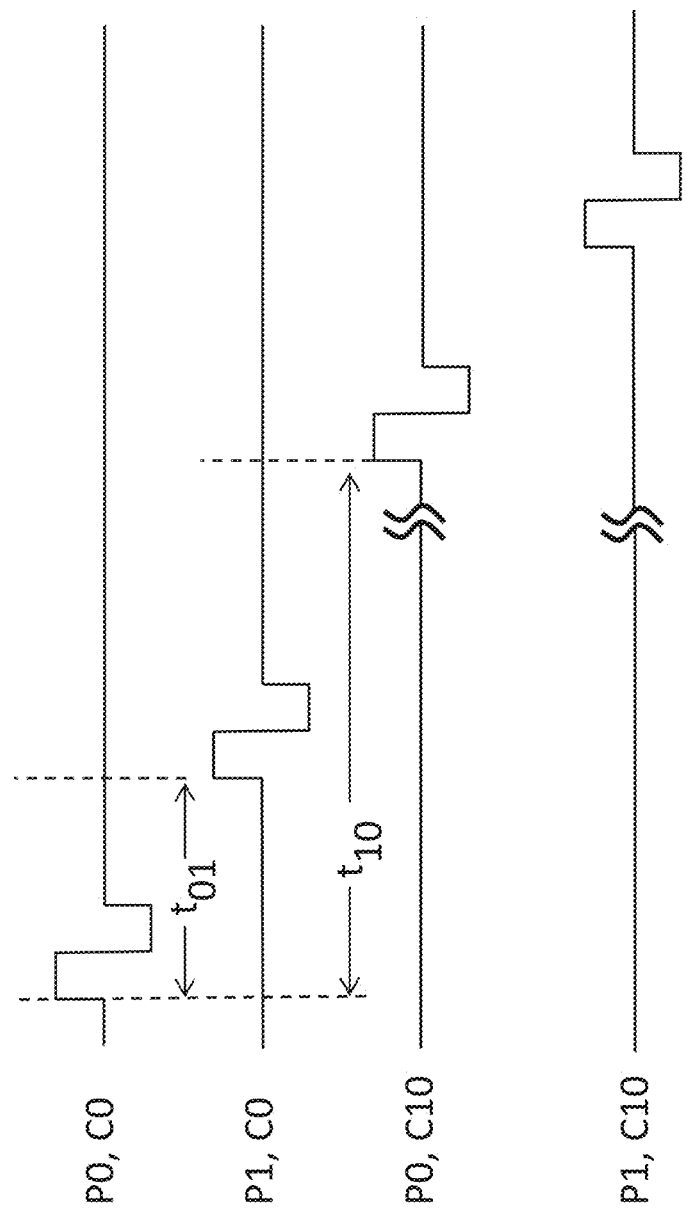
FIG. 18 shows an exemplary schematic diagram of transmit drive pulses with delays for transducer elements of different columns.

FIG. 18 shows delay relationship between columns. In this particular embodiment, the delays are determined by transmit beamformer channel delays. For example, t10 is the delay between element 0 on column 0 and element 0 on column 10. These delays are programmed in the transmit beamformer and are electrically adjustable to help focus a beam in the azimuth plane as shown in plane xa-za in FIG. 10A. In some embodiments, delays between elements on a column are separately programmed to focus a beam or tilt a beam in the elevation plane, as shown in plane ya-za in FIG. 10A. t01 is an exemplary delay between elements on a same column (e.g., elements 0 and 1 on column 0 and elements 0 and 1 on column 10). In some embodiments, delays of elements on a column are with respect to a starting delay determined by the transmit beamformer for that channel. In some embodiments, the starting delay may be predetermined by the transmit beamformer or adjustable by the transmit beamformer.

Referring to FIG. 20, in a particular embodiment, an example of the pulsar functionality is shown. In this embodiment, two digital inputs, i.e., IN1 (TxA in FIG. 17 for example), IN2 (TxB in FIG. 15A for example), control the voltage output level of the pulsar. Based on logic levels of these two inputs, a three level output result can be generated, where HVP0 is the positive high voltage, HVM0 is the negative low voltage, and XDCR is an effective ground level or 0V. In this embodiment, five cycles of an identical pulse shape are generated as the output result. In some embodiments, by changing the IN1, IN2 pattern and/or frequency of the pattern, the pattern, frequency, and/or number of pulses of the output result can be altered. In some embodiments, the logic levels or logical codings herein may include digital logic operations of one or more inputs. In some embodiments, the logic operations include using one or more logic operators on one or more inputs selected from: AND, NOT, OR, NAND, XOR, NOR, XNOR, or any other logic operations.

In some embodiments, a cascaded series/chain of flip-flops gate the transmit clock arriving at one or more column from the transmit driver for that column with a pre-determined or pre-programmed delay that is appropriate. In some embodiments, this delay is then propagated in the column by a different clock whose frequency is programmable, but synchronized to the transmit clock that generating the delay for drivers for the various column drivers. In some embodiments, the flip-flop chain generating the delay(s) stop at the central element of the column, where the delay profile is symmetrical around the center as in FIG. 17. The delays generated by the flip-flops can be routed to the proper locations in one or more column, so row 0 element has same delay as element on the last row, the element on $2^{nd}$ row has similar delay as element $2^{nd}$ from last on top side and so on.

In embodiments, elevation focus is achieved using various delay profile. Using a linear delay profile in the elevation direction such that delay monotonically increases or decrease from bottom to top of column may steer the beam in the elevation direction. On top of that, some additional curvature to the beam, where curvature is zero at ends of columns, may allow focus in addition to beam steering. Linear approximations of theoretical delays needed can be sufficiently accurate to provide steering and focus and allow economic implementations described in embodiments herein.

Figure 23:
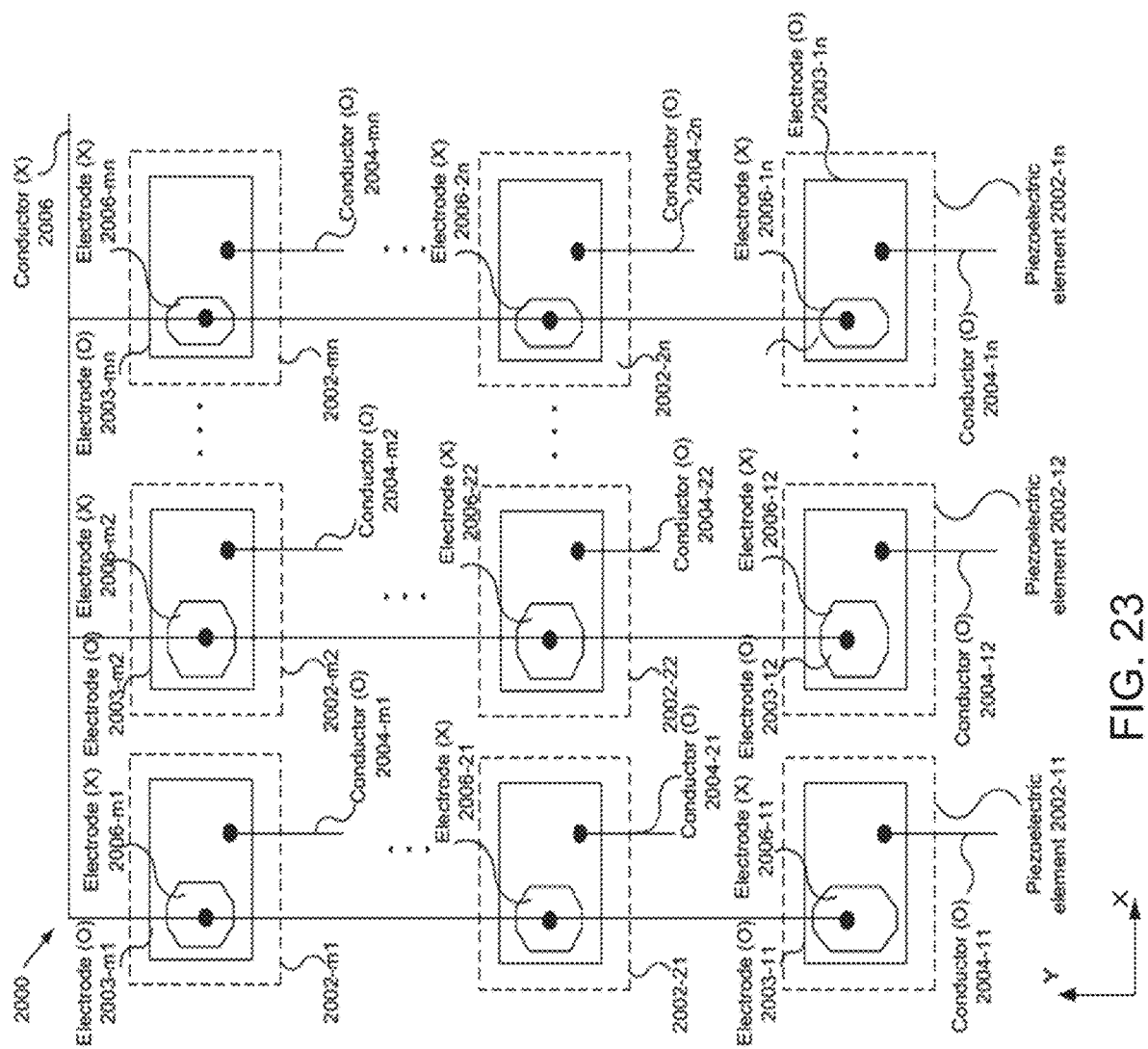
FIG. 23 illustrates a schematic diagram of an array of piezoelectric elements capable of performing two and three dimensional imaging according to embodiments of the present disclosure.

FIG. 23 shows a schematic diagram of an m×n array 2000 of piezoelectric elements 2002-11-2002-mn according to embodiments of the present disclosure. As depicted, each piezoelectric element may be a two terminal piezoelectric element (such as piezoelectric element 214 in FIG. 3A) and have an electrode (O) (e.g., 2003-11) electrically coupled to a conductor (O) (e.g., 2004-11) and an electrode (X) electrically connected to ground or a DC bias voltage via a common conductor (X) 2006. In embodiments, each signal conductor (O) may be managed independently by a circuit element). In embodiments, each conductor (O) (e.g., 2004-mn) may be electrically coupled to a transmit driver of a circuit element while all of the X electrodes (2006-11-2006-mn) of the piezoelectric element array may be connected to a common conductor (X) 2006. In embodiments, the array 2000 may be disposed on a transceiver substrate and electrically coupled to an ASIC chip by interconnection mechanism, such as m×n+1 bumps. More specifically, the m×n conductors (O) 2004-11-2004-mn may be coupled to m×n transmit drivers of ASIC chip by m×n bumps and the common conductor (X) 2006 may be coupled to the ASIC chip by one bump. In embodiments, such an exemplary arrangement as described here is used to perform 3D imaging, where each piezoelectric element, including at least one sub piezoelectric element, can provide unique information in the array. In embodiments, each piezoelectric element may have one or more membranes and vibrate in multiple modes and frequencies of the membranes. In embodiments, each piezoelectric element 2002 may be driven by pulses that have voltage profiles 3300 and 3400 in FIGS. 27 and 28.

In embodiments, the O electrodes in each column (e.g., 2003-11-2003-m1) may be electrically coupled to a common conductor. For instance, the circuit elements in the ASIC chip may be electronically controlled so that the O electrodes in each column may be electrically coupled to each other. In such a configuration, the O electrodes in each column may receive the same electrical pulse through a common transmit driver or per a multiplicity of drivers with identical electrical drive signals during the transmit mode. Similarly, the O electrodes in each column may simultaneously transmit the electrical charge to a common amplifier during the receive mode. Stated differently, the piezoelectric element in each column may be operated as a line unit (or equivalently line element).

Figure 24:
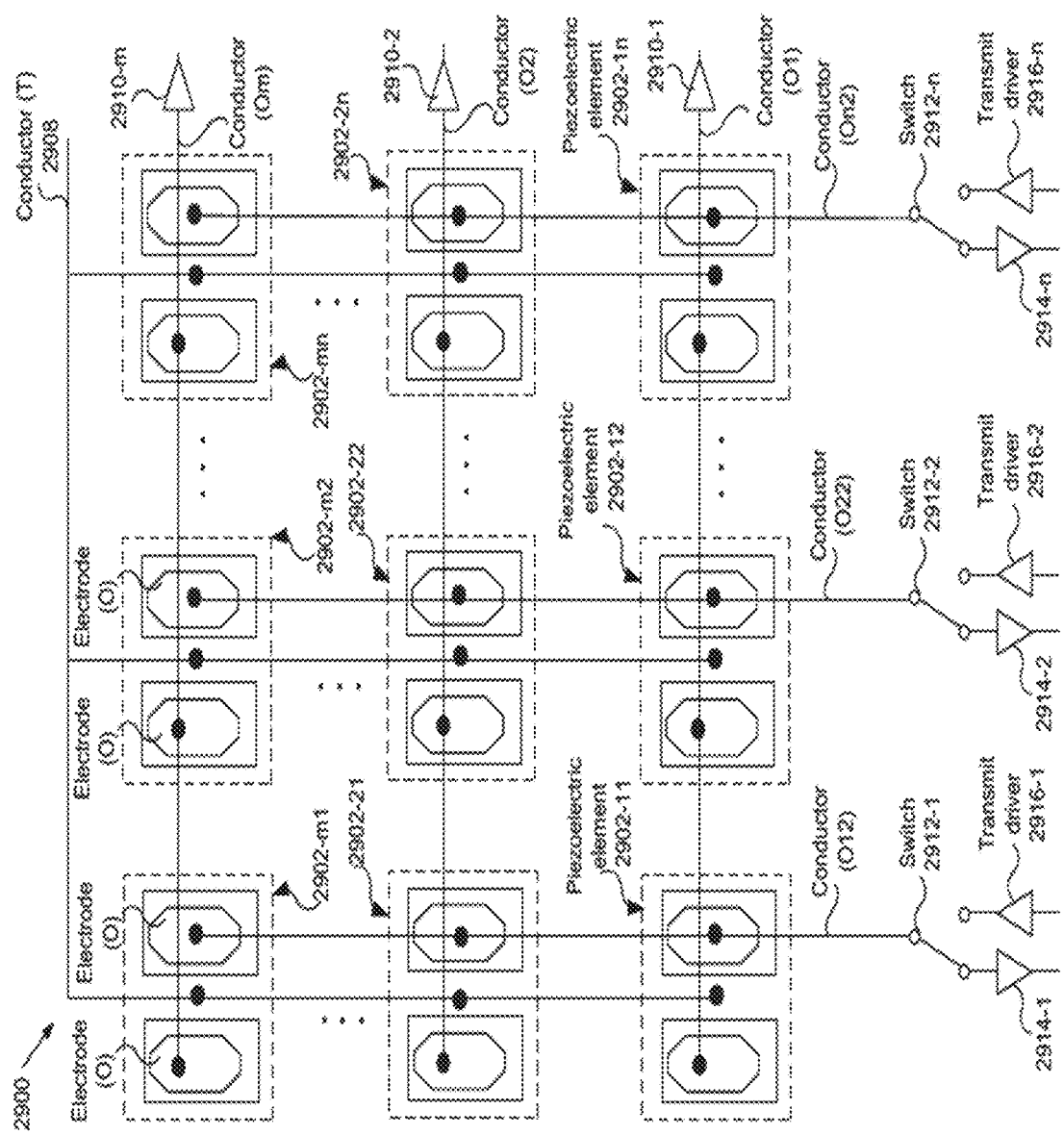
FIG. 24 illustrates a schematic diagram of an imaging system according to embodiments of the present disclosure.

FIG. 24 shows an exemplary embodiment of an imaging system 2900 according to embodiments of the present disclosure. As depicted, the imaging system 2900 includes an array of piezoelectric elements 2902-11-2902-mn and each piezoelectric element may include first and second signal (O) electrodes and a T electrode. In embodiments, all of the T electrodes in the array may be electrically coupled to one common conductor (T) 2908; each row of the first O electrodes may be electrically connected to one of conductors O1-Om; If a line imager without synthetic lens is desired. In this case a mechanical lens will suffice. However, the same thing can be achieved by not shorting all O nodes on a column as shown in FIG. 24. Instead, each O node is driven by a driver and if all driver signals for elements on a column have same delay, we have essentially achieved same behavior as shown in FIG. 24. In embodiments shown in FIG. 24, each of the switches 2912-1-2912-n may toggle between a transmit driver (e.g., 2916-1) and an amplifier (e.g., 2914-1), which may be a low noise amplifier. In embodiments, each of the conductors O1-On may be connected to one of the amplifiers 2910-1-2910-m, which may be low noise amplifiers.

In embodiments, during the transmit mode, a signal may be transmitted from a transmit driver (e.g., 2916-1) to a column of second O electrodes via a conductor (e.g., O12) so that the column of piezoelectric elements may generate pressure waves as a line unit. During the transmit mode, each switch (e.g., 2912-1) may be toggled to a corresponding transmit driver (e.g., 2916-1).

In embodiments, the imaging system 2900 may process the reflected pressure waves in two different methods. In the first method, the amplifiers 2910-1-2910-n may receive electric charge signals from the first O electrodes, i.e., each amplifier may receive signals from a row of the first O electrodes. This method allows biplane imaging/mode, where for a two dimensional image, the biplane image may provide orthogonal perspectives. Also, this method may provide more than two dimensional imaging capability. The biplane imaging may be helpful for many applications, such as biopsy. It is noted that, in this method, the transmitting and receiving modes may be performed simultaneously. In the second method, the switches 2912 may be toggled to the amplifiers 2914 so that each amplifier may receive and process the electrical charge signals from a corresponding column of the second O electrodes.

In embodiments, a line unit, which refers to a column (or row) of O electrode electrically coupled to an O conductor, may operate as a transmit unit or a receive unit or both. In embodiments, even though the conductors O1-Om are arranged in orthogonal directions to the conductors O12-On2, the directions may be electronically programmed and electronically adjustable. For instance, the gain of the amplifiers 2910 and 2914 may be adjustable electronically, where gain control leads are implemented in the amplifiers. In embodiments, the length of each line elements (i.e., the number of piezoelectric elements in each line element) may also be electronically adjusted. In embodiments, this may be achieved by connecting all signal electrodes of every piezoelectric element to corresponding nodes in the ASIC chip and, where the ASIC programs the connection between the signal electrodes of the elements to be connected to each other, transmit drivers or amplifiers as appropriate.

Figure 25:
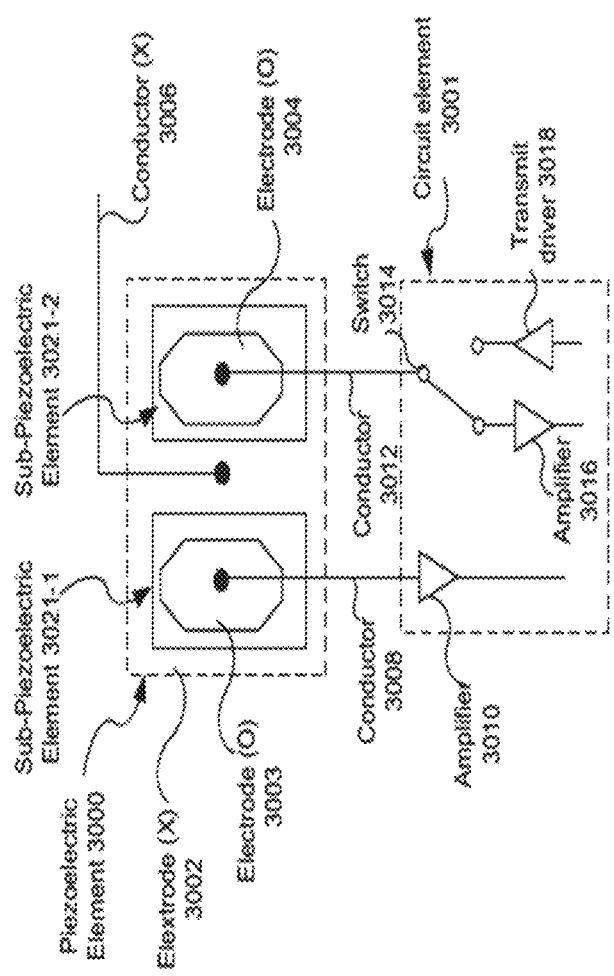
FIG. 25 shows an embodiment of a piezoelectric element coupled to a circuit element according to embodiments of the present disclosure.

FIG. 25 shows an embodiment of a piezoelectric element 3000 coupled to a circuit element 3001 according to embodiments of the present disclosure. As depicted, the piezoelectric element 3000 may include: a first sub-piezoelectric element 3021-1 and a second sub-piezoelectric element 3021-2. The piezoelectric element 3000 may include: a bottom electrode (X) 3002 that is shared by the first and second sub piezoelectric elements and coupled to a conductor (X) 3006. In embodiments, the first sub-piezoelectric element 3021-1 may include a signal (O) electrode 3003 that is electrically coupled to the amplifier 3010 via the conductor 3008. In embodiments, the second sub-piezoelectric element 3021-2 may include a signal (O) electrode 3004 that is electrically coupled to the switch 3014 via the conductor 3012.

In embodiments, a circuit element 3001 may be electrically coupled to the piezoelectric element 3000 and include two amplifiers 3010 and 3016, such as low noise amplifiers, and a transmit driver 3018. In embodiments, the switch 3014 may have one end connected to the O electrode 3004 through the conductor 3012 and the other end that may toggle between the amplifier 3016 for the receive mode and a transmit driver 3018 for the transmit mode. In embodiments, the amplifier 3016 may be connected to other electronics to further amplify, filter and digitize a receive signal, even though an amplifier is used to symbolically represent the electronics. The transmit driver 3018 may be a multi-stage drive and may generate an output with two or more levels of a signaling. The signaling can be unipolar or bipolar. In embodiments, the transmit driver 3018 may include a switch interconnecting an input to an output of a driver under electronic control of the driver, which is not explicitly shown in FIG. 25. Also not shown is the input signal to driver 3018, which may be delayed with respect to such signals for another element on the same column as shown in FIGS. 17A-D. Similarly, delays with respect to elements located in different columns are also implemented to allow electronic focus along azimuth axis, to allow for electronic focus along the elevation plane.

In embodiments, the signal of the transmit driver 3018 may be pulse width modulated (PWM), where, by controlling the pulse widths on a per element basis, a weighting function may be created on a transmitted ultrasound signal. This may for example perform a windowing function, where the transmit signal is weighted by a window function. In embodiments, the weighting coefficients may be achieved by varying the duty cycle of the transmit signal as is done during PWM signaling. This kind of operations may allow for transmit apodization, where the side lobes of a radiated signal are greatly attenuated, allowing for a higher quality image.

In embodiments, a transceiver array may be disposed in a transceiver substrate and include an n×n array of the piezoelectric element 3000 and an n×n array of the circuit elements 3001 may be disposed in an ASIC chip, where each piezoelectric element 3000 may be electrically coupled to a corresponding one of the n×n array of the circuit elements 3001. In such a case, the transceiver substrate may be interconnected to the ASIC chip by $3n^2$ bumps. In embodiments, each column (or row) of piezoelectric element array may be operated a line unit, as discussed in conjunction with FIG. 25. For instance, a same pulse may be simultaneously applied to a column of piezoelectric elements so that the column of piezoelectric elements may generate pressure waves simultaneously. It is noted that each piezoelectric element 3000 of the n×n array of piezoelectric elements may be coupled with a corresponding one circuit element 3001 of the n×n array of circuit elements. Alternately, each element on a column may be individually controlled by connecting the O node of an element to a dedicated Tx driver and also a dedicated receive amplifier. By controlling delays on the transmit driver and received signal from the LNA, elevation focus can be achieved in both the transmit and receive direction.

In embodiments, the sub-piezoelectric element 3021-1 may be in the receive mode during the entire operational period while the sub-piezoelectric element 3021-2 may be in either transmit or receive mode. In embodiments, the simultaneous operation of transmit and receive modes may allow the continuous mode Doppler imaging.

In embodiments, when the transmit driver 3018 transmits a signal to the electrode 3004, the power levels of the pressure wave generated by the sub-piezoelectric element 3021-2 may be changed by using pulse width modulation (PWM) signaling. This is important, for example, when switching from B mode to Doppler Mode imaging, signal power transmitted into the human body may be long and if power levels are not reduced, tissue damage may occur. Typically, in the conventional systems, different fast settling power supplies are used for B Mode and various Doppler Mode imaging to allow transmit drive voltages to differ in the 2 cases to for example not create excessive power in Doppler mode. Unlike the conventional systems, in embodiments, the power level may be changed by using the PWM signals on the transmit without using the conventional fast settling power supplies. In embodiments, rapid switching between Doppler and B mode imaging is desired to co-image these modes together. In embodiments, the ground electrodes of the piezoelectric element may also be separated from each other and connected to the ground separately. In embodiments, this independent grounding may reduce the noise and result in faster settling times. In embodiments, power transmitted may also be reduced by reducing the height of the transmit columns under electronic control. This again facilitates use of same power supply for both Doppler and B mode and meet power transmission requirements in each mode. This also allows co imaging.

Figure 26:
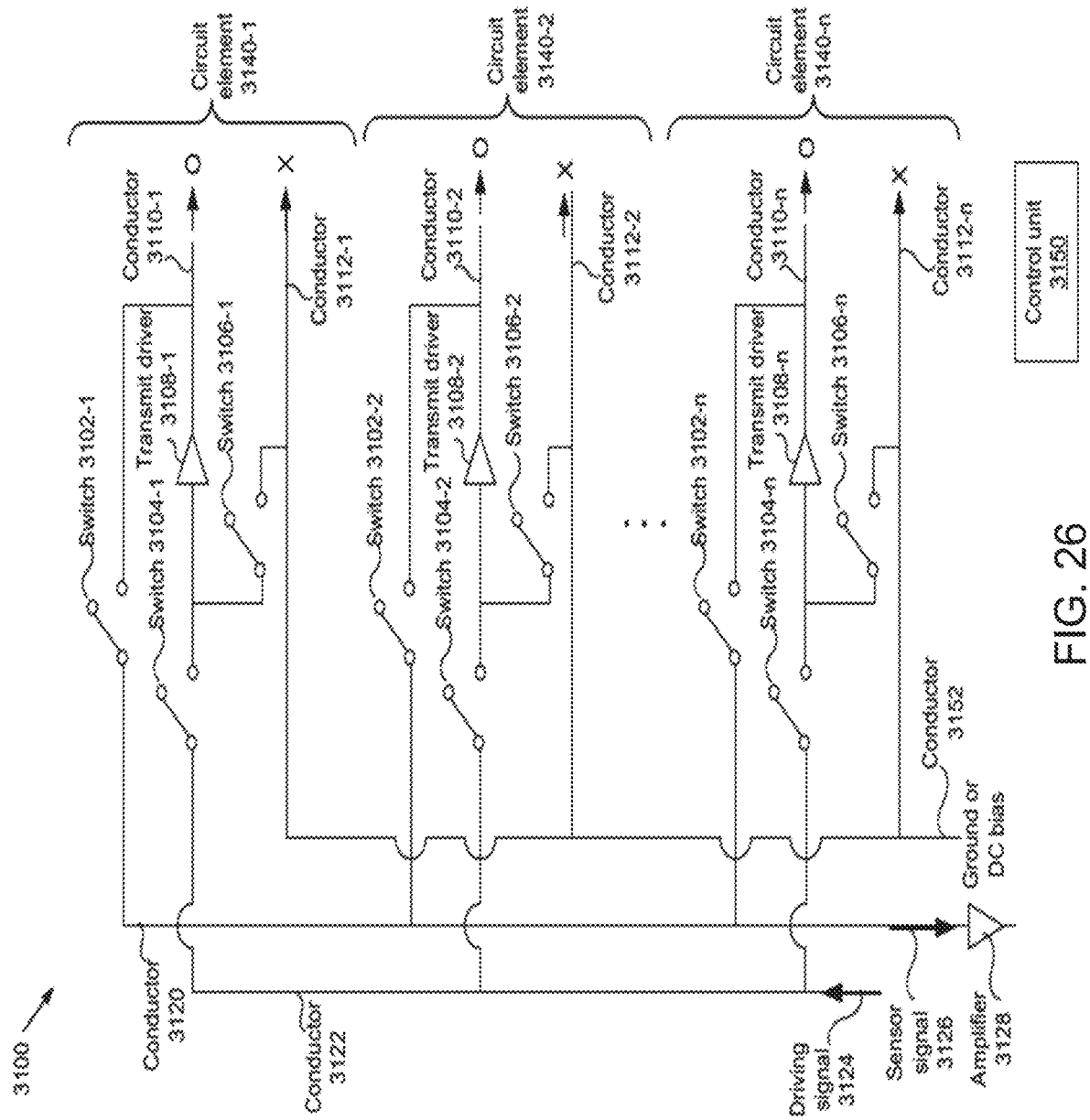
FIG. 26 shows a circuit for controlling multiple piezoelectric elements according to embodiments of the present disclosure.

FIG. 26 shows a circuit 3100 for controlling multiple piezoelectric elements according to embodiments of the present disclosure. In embodiments, the circuit 3100 may be disposed in an ASIC chip, where the array (arranged in row and columns) of piezoelectric elements that is disposed in a transceiver substrate and the ASIC chip may be interconnected to the transceiver substrate by bumps, where each pMUT may be connected to an associated Tx driver and receive circuitry through a switch as shown in FIG. 25 with O electrode connecting to switch 3014. As depicted, the circuit 3100 may include an array of circuit elements 3140-1-3140-n, where each circuit element may communicate signals with the O and X electrodes of the corresponding piezoelectric element.

As depicted in FIG. 26, each circuit element (e.g., 3140-1) may include a first switch (e.g., 3102-1), a second switch (e.g., 3104-1), a third switch (e.g., 3106-1), and a transmit driver (e.g., 3108-1). The output from the transmit driver (e.g., 3108-1) may be sent to an O electrode of the piezoelectric element via a conductor (e.g., 3110-1). During the transmit mode, each circuit element may receive a transmit driver (driving) signal 3124 through a conductor 3122. Each second switch (e.g., 3104-1), which may be transistor switches and controlled by a control unit 3150, may be turned on to transmit the signal 3124 to the transmit driver (e.g., 3108-1). (The electrical connections between the control unit 3150 and other components in the circuit 3100 are not shown in FIG. 26.) The transmit driver (e.g., 3108-1) may perform logical decode, level shift, buffer the input signal and send the transit signal to the O electrode via the conductor (e.g., 3110-1). In embodiments, during the transmit mode, the first switch (e.g., 3102-1) may be turned off.

In embodiments, the control unit 3150 may decide which piezoelectric elements need to be turned on during the transmit mode. If the control unit 3150 decides not to turn on a second piezoelectric element, the first switch (e.g., 3102-2) and the second switch (e.g., 3104-2) may be turned off, while the third switch (e.g., 3106-2) may be turned on so that the O and X electrodes have the same electrical potential (i.e., there is a net zero volt drive across the piezoelectric layer). In in embodiments, the third switches 3106 may be optional.

In embodiments, during the receive mode, the first switch (e.g., 3102-1) may be turned on so that the electrical charge developed in the O electrode may be transmitted through the conductors 3110-1 and 3120 to the amplifier 3128. Then, the amplifier 3128 may receive electrical charge signal (or, equivalently, sensor signal) 3126 and amplify the sensor signal, where the amplified signal may be further processed to generate an image. During the receive mode, the second switch (e.g., 3104-1) and the third switch (e.g., 3106-1) may be turned off so that the received signal may not be interfered. It is noted that the entire array of the circuit element 3140-1-3140-n may share a common amplifier 3128, simplifying the design of the circuit 3100. In embodiments, the X electrodes of the piezoelectric elements may be electrically coupled to the ground or a DC bias voltage via the conductors 3112-1-3112-n, where the conductors 3112-1-3112-n may be electrically coupled to a common conductor 3152.

In embodiments, the circuit 3100 may be coupled to a column of piezoelectric elements (e.g., 2002-11-2002-n1) in FIG. 23. In embodiments, the circuit 3100 may control a column of piezoelectric elements in FIGS. 25-32.

Figure 27:
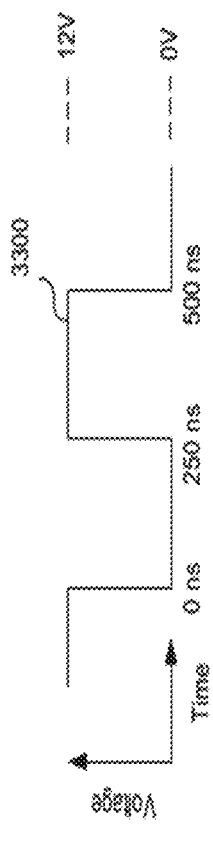
FIG. 27 shows a transmit drive signal waveform according to embodiments of the present disclosure.

FIGS. 27 and 28 show exemplary waveforms 3300 and 3400 for driving a piezoelectric element during the transmit mode according to embodiments of the present disclosure. In general, piezoelectric material may be vulnerable to damages caused by dielectric aging, and the aging may be delayed or avoided by using unipolar drive signals. The waveforms 3300 and 3400 represent the voltage potential between O and X electrodes and/or between O and T electrodes. As depicted, the waveforms may be unipolar in nature and may be a two level step waveform 3300 (i.e., the transmit driver, such as 2812, 2912, 3018, 3108, 3208, etc. is a unipolar transmit driver) or a multilevel (such as three level) step waveform 3400. The actual voltage amplitude may vary typically from 1.8 V to 12.6 V. In embodiments, the multistep waveform 3400 or a waveform with more steps may reduce heating in the piezoelectric element and have advantages for use during certain imaging modes, such as Doppler or harmonic imaging.

In embodiments, the frequency of the pulses in the waveforms 3300 and 3400 may vary depending on the nature of the signal needed and need to contain the frequency at which membrane underlying the pMUT is responsive to. In embodiments, the waveforms may also be complex signals, such as linear or non-linear frequency modulated chirp signals, or other coded signals using the Golay codes.

In embodiments, the circuits for driving the piezoelectric elements may further be designed such that the transmit output from the underlying membrane may be symmetrical in shape. In embodiments, for each signal pulse in the waveform 3300 (or 3400), the rising edge of the pulse may be substantially symmetrical to the falling edge of the pulse with respect to the center of the pulse. This symmetry lowers the harmonic content of the transmit signal, especially the second harmonic and other even order harmonics signal. In embodiments, the signal pulse in the waveform 3300 (or 3400) may be a pulse width modulated (PWM) signal.

Figure 29:
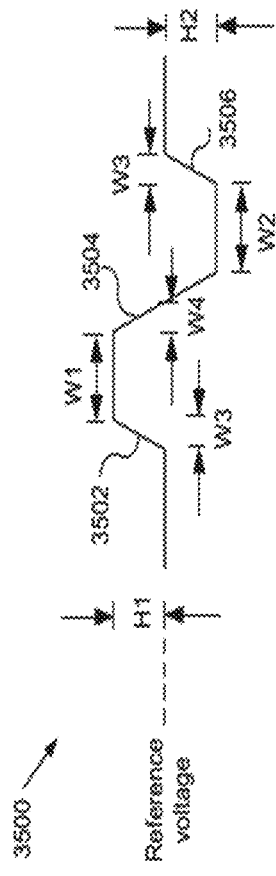
FIG. 29 shows a transmit drive signal waveform according to embodiments of the present disclosure.

FIG. 29 shows a transmit drive signal waveform according to embodiments of the present disclosure. As depicted, the signal 3500 from the transmit driver may be symmetric and bipolar i.e., the magnitude (H1) and width (W1) of the peak maximum voltage are the same as the magnitude (H2) and width (W2) of the peak minimum voltage. Also, the slope of the rising edge 3502 is the same as the slope of the falling edge 3504. In addition, the rising time W3 is the same as the fall time W4, where the fall time W4 refers to the time interval between the starting point of the fall and the reference voltage. Furthermore, the rising edge 3506 has the same slope as the rising edge 3502.

During the transmit operation, the transmit drive, e.g., 3018 in FIG. 25, may be driven by an electrical waveform, such as shown in FIGS. 27 and 28. FIG. 30 shows output signals of various circuits in an imaging assembly according to embodiments of the present disclosure. In embodiments, the waveform 3602 may be an output signal from the transmit driver, e.g., 3018 and transmitted to a piezoelectric element, e.g., 3000. In embodiments, as the piezoelectric element may have an inherent bandwidth, it may output a sinusoidal output 3604 at its resonant frequency. If the output of the transmit driver connected to the O electrode of the piezoelectric element rises very slowly, it may not be able to charge the electrode to the desired final value and thus may cause low output signals, as shown in waveform 3606, where final amplitude is smaller than in 3602. On the other hand, if the output signal of the transmit driver settles very quickly, the output signal of the transmit driver has larger bandwidth than the bandwidth limit of the piezoelectric element and therefore extra energy may be dissipated in heat. Therefore, in embodiments, as shown in the waveform 3608, the piezoelectric element may be charged at a rate such that it is completely charged but not very quickly. In embodiments, the waveform 3608, which represents the voltage potential across the top and bottom electrodes as a function of time, is closer in shape to the output of the transducer and because difference in shape is smaller, the input signal bandwidth and output signal bandwidth matches better, less loss of energy in heat occurs. In embodiments, drive impedance of transmit driver is optimized to reduce the loss of energy. Stated differently, the impedance of the transmit driver is designed to drive the piezoelectric element optimally with respect to heat dissipation and time constants needed for adequate voltage settling within a target time period.

In embodiments, the imager 126 may use a harmonic imaging technique, where the harmonic imaging refers to transmitting pressure waves on the fundamental frequency of the membrane and receiving reflected pressure waves at second or higher harmonic frequencies of the membrane. In general, the images based on the reflected waves at the second or higher harmonic frequencies have higher quality than the images based on the reflected waves at the fundamental frequency. The symmetry in the transmit waveform may suppress the second or higher harmonic components of the transmit waves, and as such, the interference of these components with the second or higher harmonic waves in the reflected waves may be reduced, enhancing the image quality of the harmonic imaging technique. In embodiments, to reduce the second or higher harmonic waves in the transmit waves, the waveform 3300 may have 50% duty cycle.

In FIGS. 23-24, the arrays may include multiple line units, where each line unit includes a plurality of piezoelectric elements that are electrically coupled to each other. In embodiments, the line units may be driven with multiple pulses that have phase differences (or equivalently delays). By adjusting the phases, the resultant pressure waves may be steered at an angle, which is referred to as beamforming.

FIG. 31A shows a plot of the amplitude of a transmit pressure wave as a function of spatial location along the azimuth axis of the transducer according to embodiments of the present disclosure. If the piezoelectric elements in the array are arranged in 2 dimensions and the piezoelectric elements on a column in the Y direction are connected and have many columns along the X direction, the X direction is known as the azimuth direction and the Y direction is known as the elevation direction.

In some embodiments, apodization herein includes using variable voltage drive, for example, with lower weights near edges and fuller weights near the central parts of ultrasonic pulses. Apodization may also be implemented by changing the number of elements along each column or rows, either alone or in combination with other methods disclosed herein.

FIG. 31B shows various types of windows for apodization process according to embodiments of the present disclosure. In FIG. 31B, x-axis represents position of a piezoelectric element relative to the piezoelectric element at the center of an active window and y-axis represents the amplitude (or, weight applied to the piezoelectric element). As depicted, for the rectangular window 3720, there is no weighting provided for any of the transmit lines, i.e., they are all at a uniform amplitude (i.e., symbolically 1). On the other hand, if the weighting function is implemented, as depicted by the Hamming window 3722, lines at the center get a greater weighting than ones at the edges. For instance, to apply the Hamming window 3722 to the transducer tile, the piezoelectric elements in the leftmost column (which is denoted as −N in FIG. 31B) and the piezoelectric elements in the rightmost column (which is denoted as N in FIG. 31B) may have the lowest weight, while the piezoelectric elements in the middle column may have the highest weight. This process is known as apodization. In embodiments, various types of window weighting may be applied, even though the Hamming window 3722 shown is only meant to be one example. In embodiments, apodization may be implemented by a variety of means such as scaling the transmit driver output drive level differently for different lines by employing a digital to analog converter (DAC) or by keeping the same drive level but reducing the number of pixels on a line The net effect is the side lobe level can be reduced by use of apodization, where the weighting of the transmit drive varies based on where a particular line is located within the transmit aperture energized.

In embodiments, the reduction in the voltage of the pulses or waveforms may lower the temperature at the transducer surface. Alternately, for a given maximum acceptable transducer surface temperature, transducers operating at lower voltages may deliver better probe performance, resulting in better quality images. For example, for a probe with 192 piezoelectric elements to reduce power consumption, transmit pressure waves may be generated by using only a portion of probe (i.e., a subset of the piezoelectric elements) and scanning the remaining elements sequentially in time using a multiplexer. Therefore, at any point of time, in the conventional systems, only a portion of the transducer elements may be used to limit the temperature rise. In contrast, in embodiments, the lower voltage probe may allow more piezoelectric elements to be addressed simultaneously, which may enable increased frame rates of the images and enhanced image quality. Significant power is also consumed in the receive path where the received signal is amplified using LNAs. An imaging system typically uses a number of receive channels, with an amplifier per receiver channel. In embodiments, using temperature data, a number of receiver channels can be turned off to save power and reduce temperature.

In embodiments, the apodization may be achieved by varying the number of piezoelectric elements in each line unit according to a window function. In embodiments, such a window approximation may be achieved by electronically controlling the number of piezoelectric elements on a line or by hardwiring the transducer array with the required number of elements. Apodization can also be created by using a fixed number of elements, but driving these elements with varying transmit drive voltage. For example, for apodization in the elevation direction, maximum drive is applied to central elements on the column and lower driver level are applied to outer elements on both side of the column around the central element on the column. Apodization can also be achieved by varying the poling strength of elements based on location on a column.

In general, the heat developed by a probe may be a function of the pulse duration in the transmit pulse/waveform. In general, to make the pressure waves penetrate deep in the target with better signal to noise ratio (SNR), a piezoelectric element may require long pulse trains. However, this also degrades axial resolution and also generates more heat in the piezoelectric elements. So, in the conventional systems, the number of pulses emitted is small, sometimes one or two. Since longer pulses may create more heat energy, making it impractical for their use in the conventional systems. In contrast, in embodiments, the pulses and waveforms 3300 and 3400 may have significantly lower peak values, which may enable the use of long pulse trains, chirps or other coded signaling. In embodiments, the longer pulse trains do not degrade axial resolution since in the receiver matched filtering is performed to compress the waveform to restore resolution. This technique allows a better signal to noise ratio and allows signal to penetrate deeper into the body and allows for high quality imaging of targets deeper in the body.

In embodiments, a layer of Polydimethylsiloxane (PDMS) or other impedance matching material may be spun over the transducer elements. This layer may improve the impedance matching between the transducer elements and the human body so that the reflection or loss of pressure waves at the interface between the transducer elements and the human body may be reduced.

In FIG. 23-24, more than one line unit may be created by connecting pixels in the y-direction (or x-direction), where one line unit (or equivalently line element) refers to multiple piezoelectric elements that are electrically connected to each other. In embodiments, one or more line units may also be created by connecting piezoelectric elements along the x-direction. In embodiments, the piezoelectric elements in a line unit may be hardwired.

Figure 7:
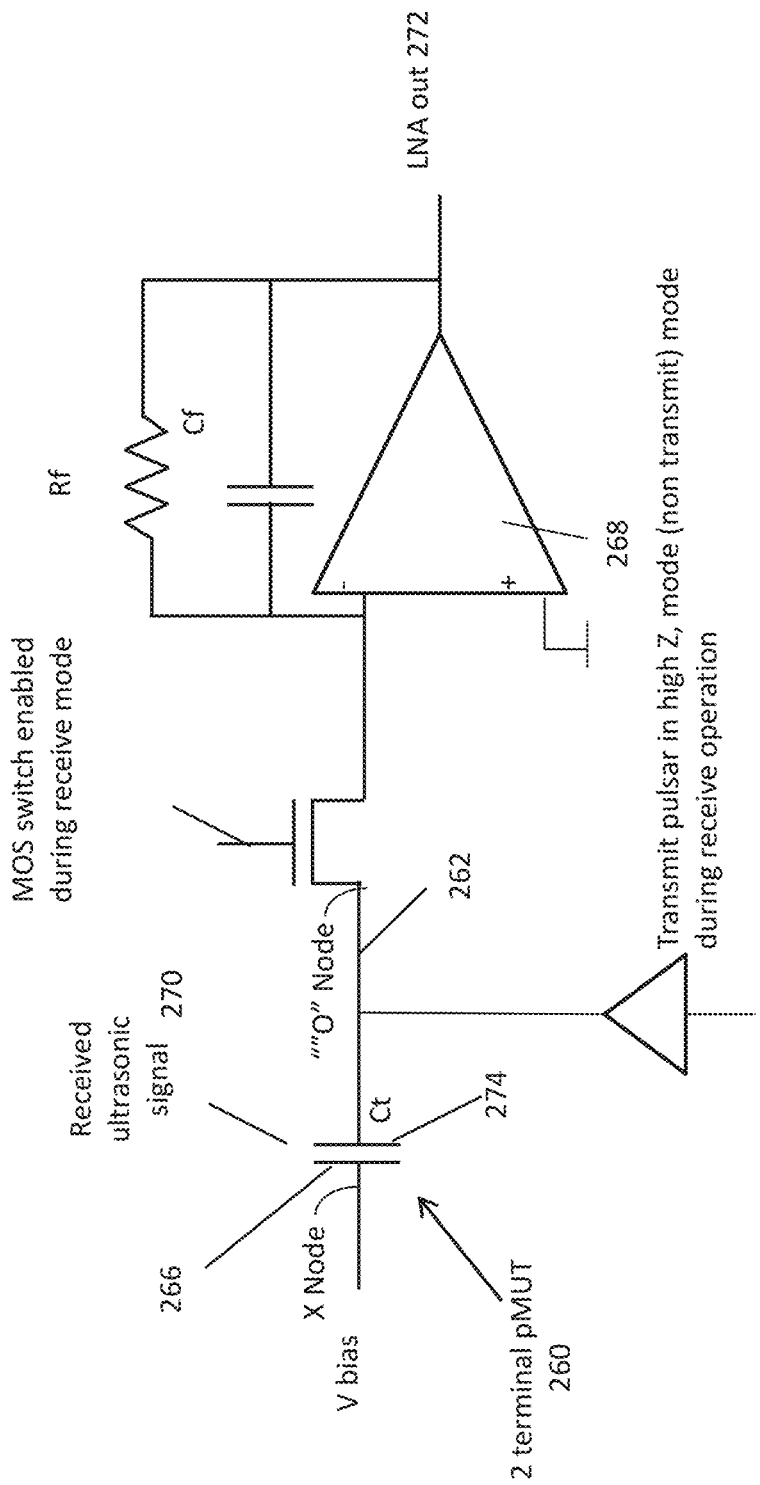
FIG. 7 shows exemplary connection of a piezoelectric element herein to a low noise amplifier (LNA) during receive mode with symbolic connection arrangement.
Figure 32:
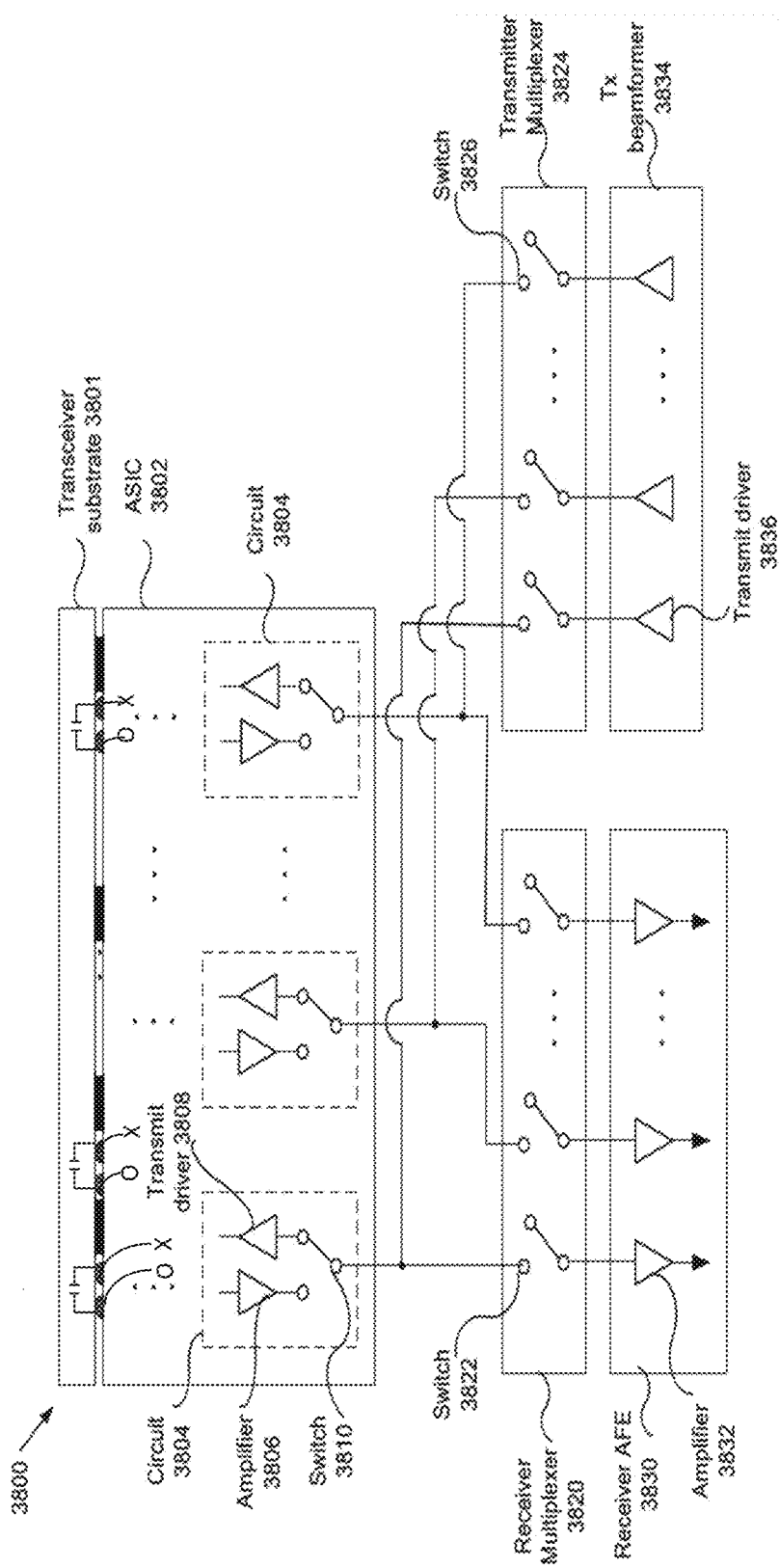
FIG. 32 shows a schematic diagram of an imaging assembly according to embodiments of the present disclosure.

As shown in FIG. 7, each piezoelectric element 260 may be electrically coupled to a circuit such as a transmit pulsar, switch and LNA. The number of piezoelectric elements in the transceiver substrate can be the same as the number of circuit in the ASIC chip that interfaces to the pMUT transducer array. Elements can be arranged in in a column or a row and can be electronically selected for connections to the ASIC containing electronic circuits For an electronically controlled line imager, a line imager/unit may be built by connecting each piezoelectric element of a two dimensional matrix array to a corresponding control circuit of a two dimensional array of control circuits, where the control circuits are located spatially close to pixels and contained for example in an ASIC such as shown in FIG. 32. To create a line element, a multiplicity of drivers controlling a column (or row) of pixels may be turned on electronically. In embodiments, the number of drivers in each line imager/unit can be electrically modified under program control and electronically adjustable.

In embodiments, smaller capacitance of each pixel may be driven efficiently by the distributed drive circuitry without other equalizing elements in between driver and pixel, eliminating the difficulty of driving a very large line capacitance. In embodiments, driver optimization may allow symmetry in rising edge and falling edges, allowing better linearity in transmit output, enabling harmonic imaging. (The symmetry is described in conjunction with FIGS. 27 and 28.) In embodiments, electronic control may allow programmable aperture size, transmit apodization, and horizontal or vertical steering control, all of which may improve image quality. In embodiments, the configurable line imager/unit under electronic control may be electrically modified under program control. For example, if a smaller number of connected elements is desired in the y-direction, the number may be adjusted by software control and without having to re-spin the control electronic circuitry or the piezoelectric array.

In embodiments, each line unit may be designed to consist of several sub units with separate control for each sub unit. The advantage of these sub units is that it may alleviate the difficulty of driving a large capacitive load for a line unit using one singe external transmit driver. For example, if two line units are created in the place of one line unit that includes the entire piezoelectric elements in a column, two different transmit drivers may be employed and each transmit driver may control half of the load of the full line unit. Also, even if one driver is used, driving the first half of the line unit and the second half of the line unit separately may improve the drive situation due to lower resistance connection to both ends of the line unit.

In embodiments, both the length and orientation of the line units may be controlled. For instanceE the line units may be arranged in both x and y directions. By way of example, in FIG. 23, the O electrodes along a column (e.g., 2003-11-2003-$n$1) may be electrically coupled to form one line unit, and the O electrodes in the other columns may be electrically coupled to form n number of line units that extend along the x-direction. More specifically, the line units that extend along the x-direction include n number of O electrodes (2003-12-2003-1$n$), . . . , (2003-$n$2-2003-$nn$). In embodiments, the arrangement of line units along orthogonal directions may be possible by controlling the electrical circuits in ASIC chip.

Arrays of transducers may be made of elements such as shown in FIG. 3B or FIG. 3C. In FIG. 3C, each element may have one or more sub elements, where each subelement has membranes disposed under the piezoelectric layer. In embodiments, the membranes may have multiple modes of vibration. In embodiments, one membrane may vibrate in the fundamental mode at a certain frequency while another membrane may vibrate at a different frequency determined by membrane design. This enables a wide frequency range of operation for the element, while still needing only 2 terminals for the element. In other embodiments, such as in FIG. 3B, the subelements can have separate drive terminals. Different drive signals for each subelement can be used to obtain wider bandwidth, by virtue of using drive signal content in different frequency zones. This also allows tuning the output signal by using multiple subelements, each with different drive signals. One such application is using a drive signal designed to counteract crosstalk from neighboring elements. In embodiments, multiple membranes may be driven by same electrode set and each membrane (sub element) may have different fundamental frequencies. In embodiments, each membrane may be responsive to a wide range of frequencies, increasing its bandwidth.

In some embodiments, the X (or T) electrodes in a column may be electrically coupled to a conductor. In embodiments, these conductors may be electrically coupled to one common conductor. For instance, the conductors may be electrically coupled to one common conductor line so that all of the T electrodes in the array may be connected to the ground or a common DC bias voltage.

In some embodiments, each array may include piezoelectric elements that are arranged in a two dimensional array (e.g., FIGS. 23-24), where the number of elements in the x-direction may be the same as the number of elements in the y-direction. However, it should be apparent to those of ordinary skill in the art that the number of elements in the x-direction may be different from the number of elements in the y-direction.

In embodiments, the ASIC chip coupled to the transducer substrate may contain temperature sensors that measure the surface temperatures of the imaging device 120 facing the human body during operation. In embodiments, the maximum allowable temperature may be regulated, and this regulation may limit the functionality of the imaging device since the temperatures should not rise beyond the allowable upper limit. In embodiments, this temperature information may be used to improve image quality. For example, if temperature is below the maximum allowed limit, additional power may be consumed in the amplifiers to lower its noise and improve system signal-to-noise ratio (SNR) for improved quality images.

In embodiments, the power consumed by the imaging device 126 increases as the number of line units that are driven simultaneously increases. All line units in the imaging device 126 may need to be driven to complete transmitting pressure waves from the whole aperture. If only a few line units are driven to transmit pressure waves, wait and receive the reflected echo at a time, it will take more time to complete one cycle of driving the entire line units for the whole aperture, reducing the rate at which images can be taken per second (frame rate). In order to improve this rate, more line units need to be driven at a time. In embodiments, the information of the temperature may allow the imaging device 120 to drive more lines to improve the frame rate.

In some embodiments, each piezoelectric element may have one bottom electrode (O) and one or more top electrodes (X and T) and have more than one resonance frequency.

In embodiments, the electrical charge developed during the receive mode is transferred to an amplifier, such as 2910, 2914, 3010, 3016, 3128, and 3806. Then, the amplified signal may be further processed by various electrical components. As such, it should be apparent to those of ordinary skill in the art that the each of the amplifiers 2910, 2914, 3010, 3016, 3128, and 3806 collectively refers to one or more electrical components/circuits that process the electrical charge signal, i.e., each amplifier symbolically represents one or more electrical components/circuits for processing the electrical charge signal.

FIG. 32 shows a schematic diagram of an imaging assembly 3800 according to embodiments of the present disclosure. As depicted, the imaging assembly 3800 may include: a transceiver substrate 3801 having piezoelectric elements (not shown in FIG. 32); an ASIC chip 3802 electrically coupled to the transceiver substrate 3801; a receiver multiplexer 3820 electrically coupled to the ASIC chip 3802; a receiver analogue-front-end (AFE) 3830; a transmitter multiplexer 3824 electrically coupled to the ASIC chip 3802; and a transmit beamformer 3834 electrically coupled to the second multiplexer 3824. In embodiments, the ASIC chip 3802 may include multiple circuits 3804 that are connected to and configured to drive multiple piezoelectric elements in the transceiver substrate 3801. In embodiments, each circuit 3804 may include a receiver amplifier (or shortly amplifier) 3806, such as LNA, and a transmit driver 3808 for transmitting a signal to a piezoelectric element, and a switch 3810 that toggles between the amplifier 3806 and the transmit driver 3808. The amplifiers may have programmable gain and means to connect them to piezo elements that need to be sensed. The transmit drivers have means to optimize their impedance and means to be connected to piezoelectric elements that are to be driven.

In embodiments, the receiver multiplexer 3820 may include multiple switches 3822 and the receiver AFE 3830 may include multiple amplifiers 3832. In embodiments, each of the switches 3822 may electrically connect/disconnect a circuit 3804 to/from an amplifier 3832. In embodiments, the transmitter multiplexer 3824 may include multiple switches 3826 and the transmit beamformer 3834 may include multiple transmit driver 3836 and other circuitry not shown to control the relative delay between transmit driver waveform of the various drivers, and other circuitry not shown to control the frequency and the number of pulses for each of the transmit drivers. In embodiments, each of the switches 3826 turn on during a transmit operation and connect to circuit 3804, while switches 3822 turn off, while switch 3810 connects to transmit driver 3808. Similarly, during a receive operation, switches 3826 turn off while switches 3822 turn on, while switch 3810 is connected to amplifier 3806.

In embodiments, the switches 3810 may be toggled to the transmit drivers 3808 during the transmit mode and toggle to the amplifiers 3806 during the receive mode. In embodiments, a portion of the switches 3822 may be closed so that the corresponding circuits 3804 may be set to the receive mode. Similarly, a portion of the switches 3826 may be closed so that the corresponding circuits 3804 may be set to the transmit mode. Since a portion of the switches 3822 and a portion of the switches 3826 may be closed simultaneously, the imager assembly may be operated in both transmit and receive modes simultaneously. Also, the receiver multiplexer 3820 and the transmitter multiplexer 3824 reduce the number of ASIC pins. In embodiments, the receiver multiplexer 3820, receiver AFE 3830, transmitter multiplexer 3824, and transmitter beamformer 3834 may be included in the circuits 202a or portions may also reside in 215a in FIG. 1B.

In embodiments, each piezoelectric may have more than two electrodes, where one electrode may be in the transmit mode to generate pressure waves while the other electrode may be simultaneously in the receive mode to develop electrical charge. This simultaneous operation of transmit and receive modes allow for better Doppler imaging Movement in target being imaged may cause errors in the resulting image and it may be desirable to reduce these errors. An example of movement is when performing cardiac imaging where the heart tissue is moving. High frame rates can be desirable to reduce impact of movements. Therefore, improving frame rates while maintaining electronic azimuth and elevation focus and apodization can be important. This may not only reduce burring in images but also allow for better images using dynamic focus in the receiver by electronically altering azimuth and electronic focus as a function of depth. Frame rate improvement can be achieved in a dual stage beamformer illustrated in FIG. 14, by simultaneously operating the top and bottom section at same time, reducing the number of operations. Further by completing the scan of one complete column, for example A1, B1 and C1 of FIG. 12 before generating A2, B2, C2 helps minimize impact of movements on a line. Further, one scan line can be created by using the transmission and reception of all rows and columns in the section operated. However, using a parallel beam former technique [High frame rate ultrasound imaging using parallel beamforming, Tore Grüner Bjåstad, Thesis for the degree of Philosophiae Doctor Trondheim, January 2009 Norwegian University of Science and Technology], multiple beams can be created, for example, 4. This can help further increase the frame rate and reduces impact of movements. These techniques also may create aberrations, but there are known electronic ways to correct them.

It may be desirable to output a larger pressure level (without exceeding regulatory limits) to improve image quality. The value of equalization is the increase in pressure output in the frequency region of interest. This increase in pressure output results in a larger signal output that results in an improved signal to noise ratio and improved signal penetration into the tissue, improving imaging depth. PMUTs are highly capacitive and adding inductances in series with them can help reduce reactance and better match driver impedance to assist with increased power transfer.

FIGS. 33-37 show transducer arrays and circuits that may be arranged in columns (and rows) and used for transmitting and receiving an ultrasonic beam. Uniquely, an inductor is in the path of current flowing through the transducer and through the inductor to virtual ground (a bias voltage). The addition of an inductor in series with the transducer helps compensate for the capacitive component of the transducers impedance and helps impedance matching of the driver (at the O node in FIG. 36A) to the impedance of the transducer and helps maximize power transfer to the transducer. The transmit driver directly drives the transducer and the inductor is in the ground return (or bias return lead of the transducer. In this disclosure, the values of the inductor (e.g., of around 0.5 µH), do not enable these inductors to be used in a low-frequency region (e.g., 2 MHz), since the area needed for each inductor is very large and the number of inductors is also large. Arranging the inductors to be in the ground return path, allows these inductors to be off chip with a minimum increase in number of extra pins (where one extra pin is needed for each inductor). To implement an inductor in series with a driver would require two pins per inductor for off chip implementation.

Figure 33A:
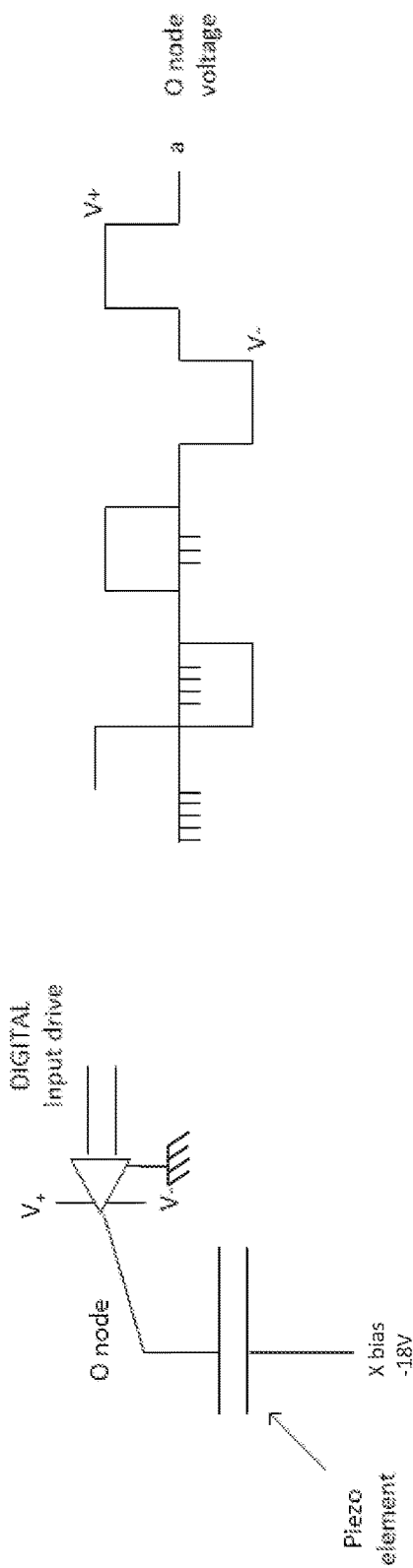
FIG. 33A shows a circuit containing a piezo element, which may be part of a piezo element array.
Figure 33B:
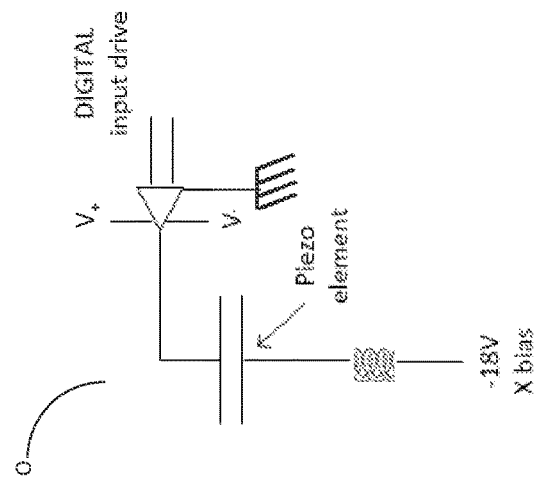
FIG. 33B shows a modification to the circuit of FIG. 33A, with an inductor connected in series between the piezo element and the X bias node.
Figure 33C:
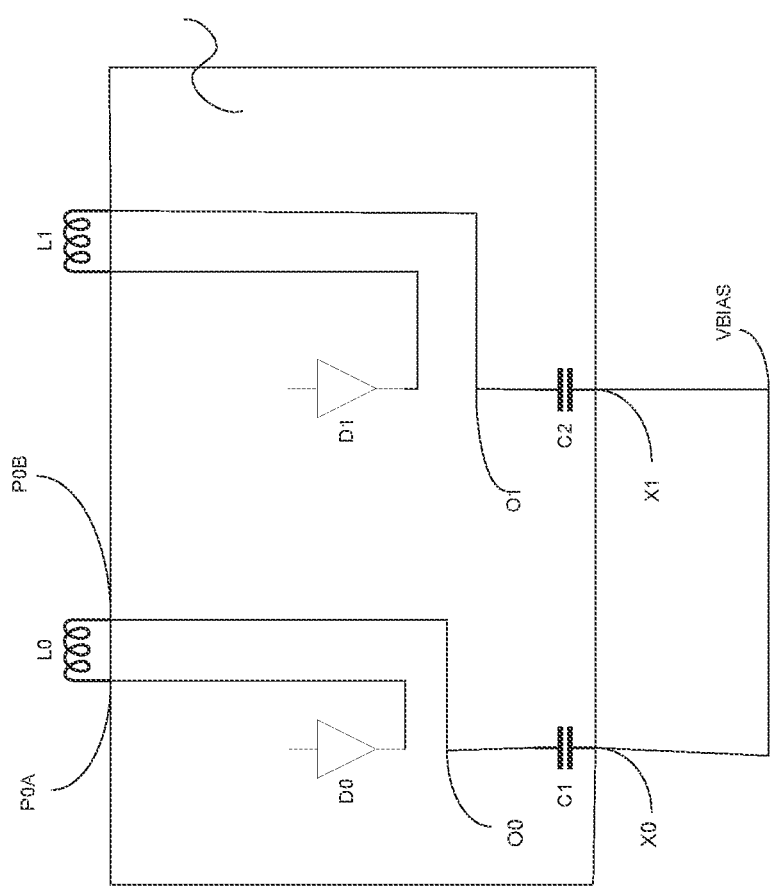
FIG. 33C shows a technique of using an inductor in between a transmit driver and the transducer it is driving.
Figure 33D:
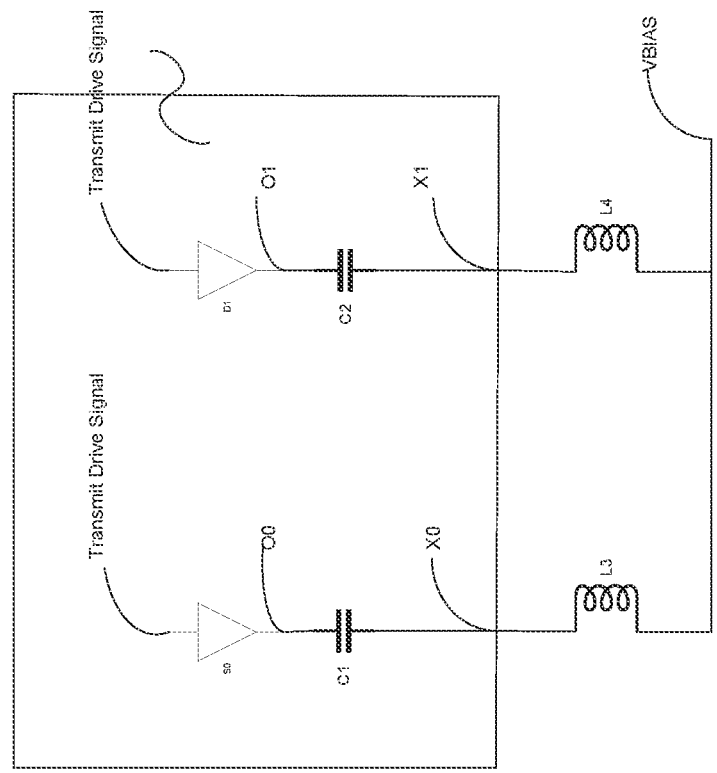
FIG. 33D shows a novel technique of placing the inductor between its return lead to ground (or Vbias) and actual ground (or Vbias).

FIG. 33C shows an example of using inductor-based equalization using a legacy technique of adding an inductor in series with the transmit driver. Here D0 is a transmit driver. The output of the driver is connected off chip to a pin P0A. An external inductor L0 is connected and other terminal of inductor is connected to pin P0B and retuned to circuit to drive transducer C0, where the other terminal of C0 goes to a pin X0 to be connected to a bias voltage. An issue with this technique is the requirement for extra pins P0A, P0B per inductor. Also interconnect wiring is significant. Additionally, the driver output comes out on a pin and gets exposed to parasitic loading that degrades performance of driver. For a 128 channel imager, requiring 128 inductors, 256 extra pins would be needed, making it a large burden or impractical. Further, the amount of interconnect would greatly increase compared to the subject matter described herein. This is especially important, since current levels are high, to keep impedance similar, requires increasing dimensions of the interconnect. Because of the need for two separate wires, the length of the interconnect doubles. Therefore, integrating an equalization technique using this legacy technique is not practical. A different technique is disclosed in FIG. 33D, whereby moving the inductor on the other side of the transducer (in series between the transducer and the bias voltage), only one extra pin and one extra interconnection wiring is needed, making integrating an equalization technique feasible. In fact, in many cases, since pins X0,X1 come out tp pins anyway, there is little penalty to add inductors for equalization, compared to situation with no inductor based equalization. The transposition of the inductors on the other side of the transducer not only has the advantages described, it additionally maintains the circuit's ability to perform equalization. Notably, this circuit also retains the ability to focus in the azimuth and elevation directions, with the focus control being dynamic as disclosed herein. The piezo element circuits include inductors, which allow for the circuits to be configured to transfer a maximum amount of power in the ultrasonic beam. Means to use the inductors within the circuits are integrated in such a manner that they do not take up too much space and make the circuits practical to build and use.

FIG. 33A shows a circuit containing a piezo element, which may be part of a piezo element array. The piezo element array may, for example, contain 4096 piezo elements, arranged in a grid of 128 columns and 32 rows, and may be for the purpose of forming a particular transmitted ultrasonic beam with a dynamic focus. Individual elements in the array of piezo elements may receive signals that are delayed in time, in order to change the focus of the transmitted ultrasonic beam. The terms "piezo element" and "pMUT transducer element" are herein used interchangeably. In addition, the terms "piezo element circuit" and "pMUT transducer circuit" are also interchangeable.

The circuit of FIG. 33A shows the piezo element as well as its O node and X node and a digital input drive. The O node may designate an input terminal for transmission of a drive signal from the digital input drive to the piezo element. The X node may be a bias or ground node. In the embodiment of FIG. 33A, the X node is biased at −18 V, but may also be biased at other voltages, such that it is more negative than the most negative drive voltage on the O node.

In the embodiment of FIG. 33A, the piezo element may be highly capacitive and is represented as a capacitor, for the purpose of properly identifying its behavior as a circuit element. The drive signal provided by the digital input drive may be, for example, a square wave, a step wave, a sinusoidal wave, a triangular wave, or another type of alternating voltage signal. For a particular piezo element, the digital input drive may delay the particular signal provided to the piezo element. An amount of temporal delay may be determined by a placement of the piezo element within the array, and may relate to a numbered row or column index label of the piezo element.

FIG. 33B shows a modification to the circuit of FIG. 33A, with an inductor connected in series between the piezo element and the X bias node. The inductor may be connected to correct a phase shift introduced by a complex impedance of the capacitive piezo element. Canceling out the phase shift by connecting the inductor is performed to increase power transfer by performing impedance matching. Integrating the inductor on a chip along with other circuitry is not practical for lower imaging frequencies (such as in the 1-10 MHz area). This is due to the size of the inductor and number of inductors needed on chip. When frequencies increase (for example, in the range of 50 MHz-100 MHz), the size of the inductor becomes smaller. Thus, the inductor becomes more practical to be integrated in a chip. The bulk of commercial medical imaging applications today are in the frequencies less than 10 MHz. Since, in practice, it may be difficult to integrate the inductor for these applications, in one embodiment, external inductors are used to connect an integrated circuit with a matrix array of transmit and receive circuitry that are connected to a matrix array of transducers. FIG. 33A shows one terminal of the transducer connected to a bias voltage (analogous to a ground reference). An external inductor is connected in between the transducer and the bias terminal. This requires the addition of only one pin per inductor, since the other terminal (Xbias is a common pin and already available). Such an arrangement allows inductor based equalization. For example, for a matrix array arranged in 128 columns and 32 rows, 128 inductors would be sufficient, where elements on a column are selected as desired (as shown in FIG. 34, through uses of switches under program control)

Figure 34:
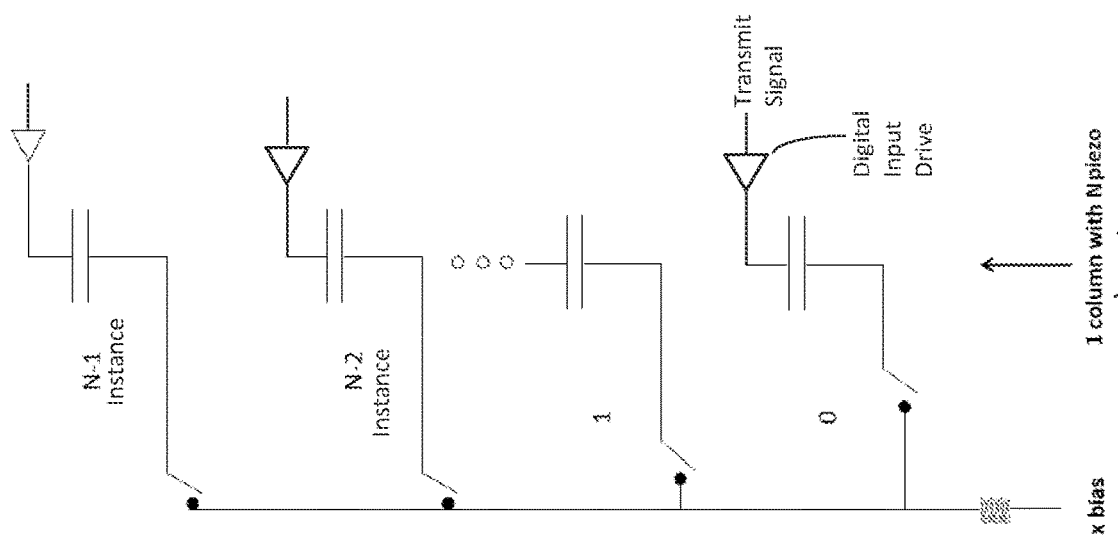
FIG. 34 shows a column of N piezo element circuits, of the type shown in FIG. 33B, connected to a common inductor placed in series between the piezo elements (logically selected and in parallel with one another) and the X bias terminal.

FIG. 34 shows a column of N piezo element circuits, of the type shown in FIG. 33B, connected to a common inductor placed in series between the piezo elements (in parallel with one another) and the X bias terminal. In this embodiment, the N piezo elements have N corresponding digital input drives. In other embodiments, equivalent of one input drive may be used to drive multiple piezo elements, for example, if the piezo elements are configured to transmit signals with equal delays. In another example, a transducer drive signal may be delayed relative to each other to enable electronic focusing in the elevation direction as explained in FIGS. 15-19. Multiple piezo elements may be selected at one time from the group, and piezo elements may be deselected or disconnected by disconnecting switches connecting them to the inductor and X bias terminal. The value of the inductor may be chosen to be large enough to offset changes in phase introduced by the capacitances of the piezo elements. For example, if 32 piezo elements are selected electronically, the column capacitance may be 1000 pF and the inductors may have inductance of 0.5 µH. Using these inductance to compensate for capacitance allows the system bandwidth to be improved selectively at certain frequencies. For example, pressure output can be improved over a certain bandwidth (for example, 1 MHz-6 MHz) can be improved, while pressure at higher frequencies say at >10 MHz can be decreased.

FIG. 35 illustrates multiple columns of piezo element circuits, of the type illustrated in FIG. 33A, without an inductor connected between the piezo elements and the X bias terminal. The embodiment of FIG. 35 shows two columns, but there may be 128 columns, each with 32 piezo elements per column, in a 4096 piezo element array. Larger column and row sizes are also possible or practical, as determined by application requirements, while still falling within the scope of this disclosure. The two columns shown have the transmit drive delayed relative to each other to allow for electronic focusing in the azimuth direction. Additional inductors similar to that shown in FIG. 34, allow similar focusing functionality and is shown in FIG. 36B. Note, the shorting switch may be not needed in some applications, where the value of the inductor does not need to change.

Figure 36A:
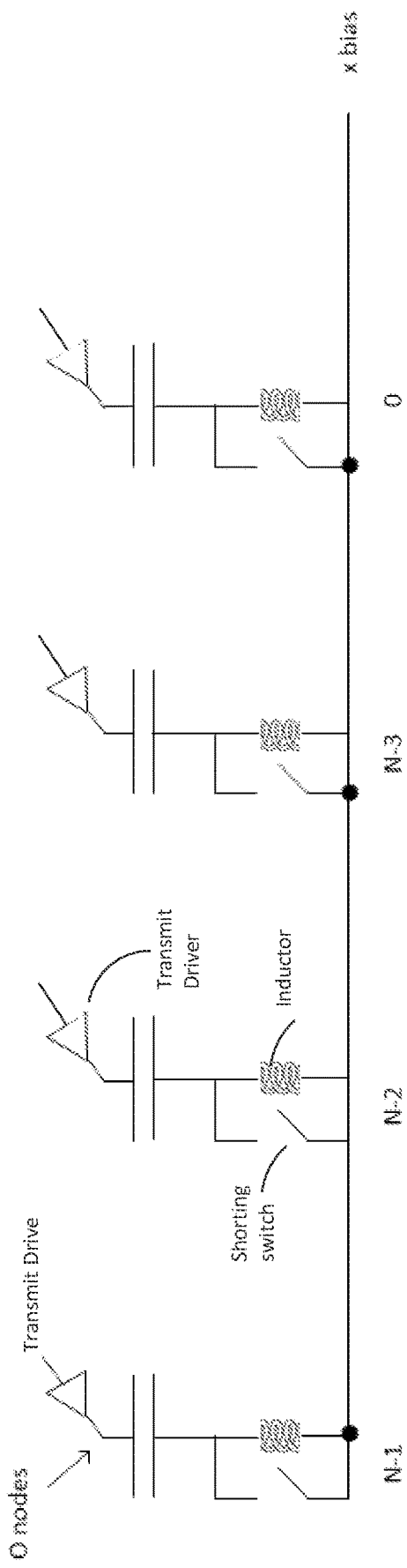
FIG. 36A illustrates an embodiment with multiple columns connected to a common X bias line.
Figure 36B:
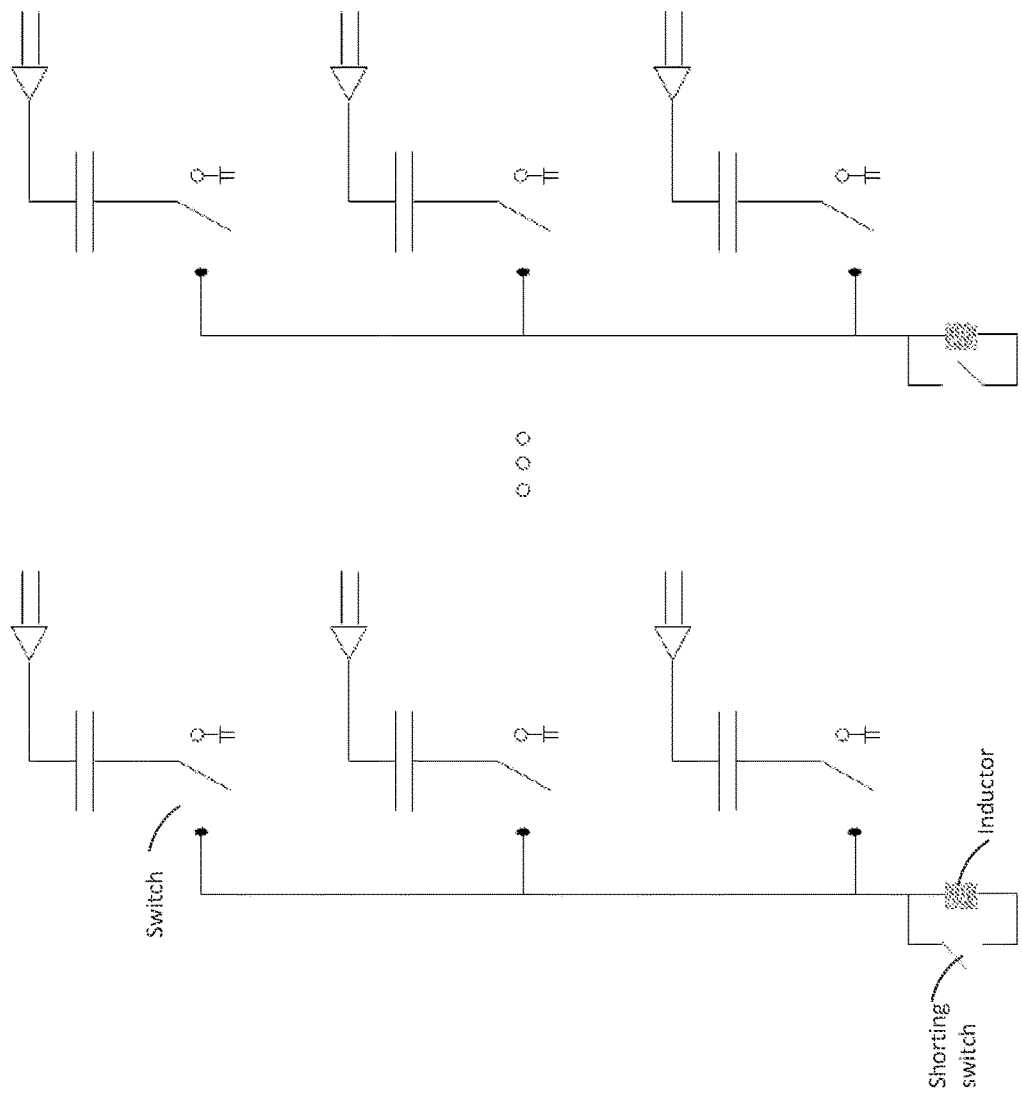
FIG. 36B illustrates an embodiment where multiple piezo elements are arranged per column. Individual piezo elements may be logically selected using switches connected in series with the piezo elements. Inductor may be bypassed by switches if desired.
Figure 37:
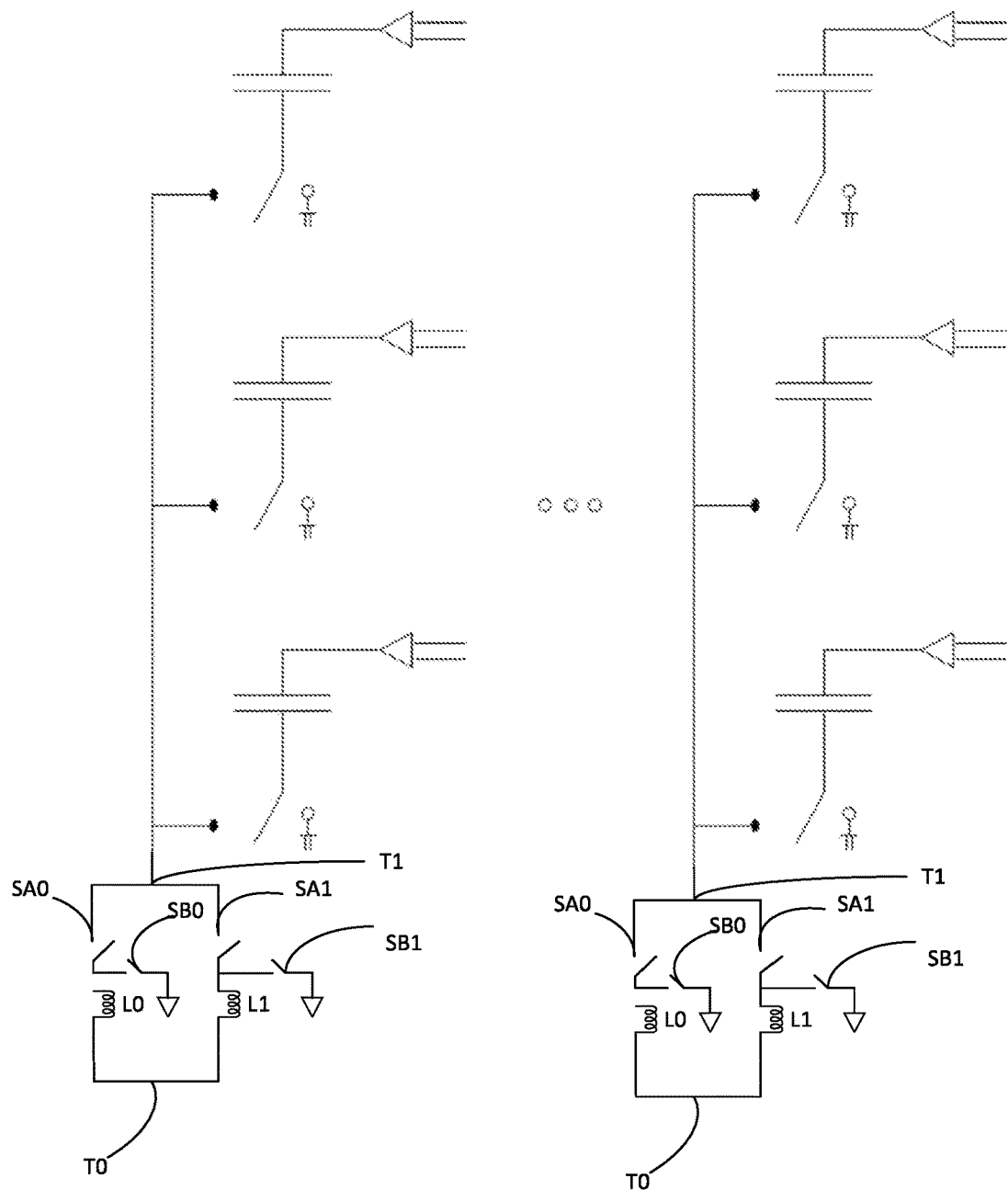
FIG. 37 shows an implementation of an inductor, composed of a bank of switchable and electronically selectable inductors.

FIG. 36A illustrates an embodiment with multiple columns connected to a common X bias line. In the embodiment of FIG. 36A, there are multiple columns with multiple inductors. The inductors may be shorted using a shorting switch. This is because, at high frequencies of the drive signals, the inductors bandlimit the imager, reducing ultrasonic pressure output from the transducer and possibly degrading image quality, parallel, with shorting cap. In another embodiment, when it is feasible to integrate inductors on an ASIC along with other circuitry, using a switching arrangement, it would be feasible to select the value of the inductor desired. This switching arrangement would have N inductors, replacing each inductor shown, for example, in FIG. 34. The N inductors would have a common terminal while the other terminal would have a switch in series with the other end of the switch tied together as shown in FIG. 36B and FIG. 37. FIG. 37 shows an arrangement of inductors that can be switched electronically to change the value of the inductor. The circuit has two inductors, L0 and LI, connected in parallel between terminals TO and Tl. Each inductor L0, L1 has a switching arrangement such as represented by SA0, SA1 and SB0, SB1, respectively. When the inductor LO is to remain in circuit, SA0 is on and SBO is off and vice versa. When the inductor L1 is to remain in circuit, SA1 is on and SB1 is off and vice versa. These switches are synchronized logically to be complementary. For example, SBO, when turned on, shunts the current flowing through inductor L0 to ground. SA0, when turned on, connects inductor L0 to terminal Ti. Such a composite inductor can replace each inductor in FIG. 36B as shown in FIG. 37.

In some embodiments, although electronic or electrical connections between individual elements shown in figures herein are hardwired or physical connections, different digital connections may be used to thus enable programmable and more flexible digital communications. In some embodiments, such digital connections may include but not limited to switches, plugs, gates, connectors, etc.

Although certain embodiments and examples are provided in the foregoing description, the instant subject matter extends beyond the specifically disclosed embodiments to other alternative embodiments and/or uses, and to modifications and equivalents thereof. Thus, the scope of the claims appended hereto is not limited by any of the particular embodiments described. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

As used herein A and/or B encompasses one or more of A or B, and combinations thereof such as A and B. It will be understood that although the terms "first," "second," "third," etc. may be used herein to describe various elements, components, regions and/or sections, these elements, components, regions and/or sections should not be limited by these terms. These terms are merely used to distinguish one element, component, region or section from another element, component, region or section. Thus, a first element, component, region or section discussed below could be termed a second element, component, region or section without departing from the teachings of the present disclosure.

The terminology used herein is for the purpose of describing particular embodiments only and is not intended to limit the present disclosure. As used herein, the singular forms "a," "an," and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

As used in this specification and the claims, unless otherwise stated, the term "about," and "approximately," or "substantially" refers to variations of less than or equal to +/−0.1%, +/−1%, +/−2%, +/−3%, +/−4%, +/−5%, +/−6%, +/−7%, +/−8%, +/−9%, +/−10%, +/−11%, +/−12%, +/−14%, +/−15%, or +/−20% of the numerical value depending on the embodiment. As a non-limiting example, about 100 meters represents a range of 95 meters to 105 meters (which is +/−5% of 100 meters), 90 meters to 110 meters (which is +/−10% of 100 meters), or 85 meters to 115 meters (which is +/−15% of 100 meters) depending on the embodiments.

While preferred embodiments have been shown and described herein, it will be obvious to those skilled in the art that such embodiments are provided by way of example only. Numerous variations, changes, and substitutions will now occur to those skilled in the art without departing from the scope of the disclosure. It should be understood that various alternatives to the embodiments described herein may be employed in practice. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the disclosure and that methods and structures within the scope of these claims and their equivalents be covered thereby.

What is claimed is:

1. An ultrasonic imaging system comprising a transducer comprising:
   a) a plurality of transducer elements, wherein each transducer element has a first terminal and a second terminal;
   b) a plurality of transmit drivers, wherein each transmit driver is connected to each first terminal of the plurality of transducer elements; and
   c) at least one inductor; and;
   d) a complementary switch communicatively coupled to an inductor of the at least one inductor, wherein the complementary switch connects the inductor either to (i) a second terminal of a transducer element of the plurality of transducer elements or (ii) to a ground.

2. The ultrasonic imaging system of claim 1, wherein the transducer is a piezoelectric micro machined transducer (pMUT) device, a capacitive micromachined ultrasonic transducer (cMUT) device, or a bulk piezo transducer.

3. The ultrasonic imaging system of claim 1, wherein the plurality of transducer elements is organized in an array, wherein the array is organized in rows and columns, wherein one or more transducer elements of the plurality of transducer elements along a column is electronically selected to define a column of transducer elements, and wherein one or more transducer elements of the plurality of transducer elements along a row is selected electronically to define a row of transducer elements.

4. The ultrasonic imaging system of claim 1, wherein the inductor of at least one transducer circuit of the column of transducer circuits is connected in parallel to a switch, wherein closing the switch shorts the inductor.

5. The ultrasonic imaging system of claim 3, where delays of the plurality of transducer elements in a first column are independent from delays of the plurality of transducer elements in a second column and delays of the plurality of transducer elements in a first row are independent from delays of the plurality of transducer elements in a second row.

6. The ultrasonic imaging system of claim 3, wherein transducer elements on a column have different delays.

7. The ultrasonic imaging system of claim 3, wherein a bandwidth of the transducer is increased in a region of interest.

8. The ultrasonic imaging system of claim 3, wherein a value of an inductor of the at least one inductor is selected to provide a pressure output adjustment in a frequency range of interest, and wherein the pressure output adjustment is produced by changing a plurality of voltage drive levels of a subset of transmit drivers of a subset of transducer elements of the plurality of transducer elements, wherein the subset of transducer elements comprises at least a first column of transducer elements.

9. The ultrasonic imaging system of claim 3, wherein a value of an inductor of the at least one inductor is chosen to be large enough to offset changes in phase introduced by at least one capacitance of the at least one transducer element.

10. The ultrasonic imaging system of claim 3, wherein a transmit driver of the plurality of transmit drivers is configured to drive the plurality of transducer elements along a column, wherein the transmit driver is driven by signals from a transmit channel, wherein the signals of the transmit channel are delayed electronically relative to delay applied to other transmit channels driving other transducer elements on different columns.

11. The ultrasonic imaging system of claim 3, wherein a transducer element of the plurality of transducer elements comprises a top section, a central section, and a bottom section, each of which comprise a number of rows and a number of columns for pulse transmission and reception of the reflected ultrasonic signal, wherein the pulse transmission and reception of the reflected ultrasonic signal from the top section, central section, and bottom section is used for focusing the reflected ultrasonic signal in an azimuth direction using a first beamformer, and wherein an elevation focus is achieved using a second beamformer.

12. The ultrasonic imaging system of claim 6, wherein the transducer is configured to provide electronic control of elevation focus in an elevation direction along the column.

13. The ultrasonic imaging system of claim 6, further comprising a control circuit configured to electrically control relative delays along a column to be a summation of a linear delay and an arbitrary fine delay, wherein the linear delay and arbitrary fine delays of the column are independent from other linear delay and arbitrary fine delays of other columns of the transducer, thereby allowing for arbitrary steering and focusing in three dimensions.

14. The ultrasonic imaging system of claim 7, wherein two adjacent transducer elements of the plurality of transducer elements on a row of the one or more rows are addressed together and wherein a transducer element of the plurality of transducer elements comprises a top section, a central section, and a bottom section, each of which comprise a first number of rows and a second number of columns for the ultrasonic pulse transmission and reception of the reflected ultrasonic signal, wherein the ultrasonic pulse transmission and reception of the reflected ultrasonic signal from the sections are used for focusing the reflected ultrasonic signal in an azimuth direction using a first beamformer, wherein elevation focus is achieved using a second beamformer, wherein, for imaging using a B mode, a receive channel is assigned to two transducer elements of the plurality of transducer elements on a same row, one of the two transducer elements from the top section and the other of the two elements from the bottom section, and another channel is assigned to two transducer elements of the central section, and wherein 2N receive channels are used to address N columns.

15. The ultrasonic imaging system of claim 8, wherein the voltage drive levels are changed using a multilevel transmit drive pulse and selecting a desired digital drive level.

16. The ultrasonic imaging system of claim 15, wherein the voltage drive levels are further controlled using pulse width modulation on a transmit pulsar waveform.

17. The ultrasonic imaging system of claim 15, wherein a transducer element of the first column of transducer elements is driven by a multilevel pulse, and wherein a delay of an onset of the multilevel pulse is electrically programmable.

18. The ultrasonic imaging system of claim 17, wherein the transducer element of the first column of transducer elements is driven by a sequence of multilevel pulses, and wherein pulse magnitude, width, shape, pulse frequency, and combinations thereof, of a multilevel pulse of the sequence of multilevel pulses are electrically programmable.

19. The ultrasonic imaging system of claim 17, wherein the delay for the transducer element of the first column of transducer elements, indexed by a row and a column, is calculated by summing a delay for the column with a delay for the row.

20. The ultrasonic imaging system of claim 17, wherein the delay may be a summation of a coarse delay and a fine delay.

21. The ultrasonic imaging system of claim 17, wherein the delay of pulse onset is programmable in an X direction and in a Y direction.

22. The ultrasonic imaging system of claim 10, wherein the plurality of transducer elements along the column operate with substantially identical delays.

23. The ultrasonic imaging system of claim 10, wherein the transmit channel and additional transmit channels are configured to electrically control relative delays between adjacent columns, and wherein the control circuit is configured to set relative delays for a first number of transducer elements on the columns such that the first number of transducer elements in a same row share substantially identical relative delays with a second number of transducer elements of a starting row.

24. The ultrasonic imaging system of claim 11, wherein a focal distance in an elevation direction is electronically programmed.

25. The ultrasonic imaging system of claim 11, wherein the pulse transmission and reception of the reflected signal of the top section and the bottom section are performed simultaneously.

26. The ultrasonic imaging system of claim 14, wherein all of the plurality of transducer elements selected electronically are operated on to generate pressure with elevation focus in a transmit operation, and wherein, in a receive operation, all of the plurality of transducer elements separately electronically selected are used to reconstruct an image with focusing in the azimuth direction and an elevation plane.

* * * * *